United States Patent
Liu et al.

(10) Patent No.: US 12,084,520 B2
(45) Date of Patent: Sep. 10, 2024

(54) ANTIBODIES BINDING BCMA AND CD3 AND USES THEREOF

(71) Applicant: BEIJING MABWORKS BIOTECH CO., LTD, Beijing (CN)

(72) Inventors: Fangjie Liu, Beijing (CN); Jiangmei Li, Beijing (CN); Wenqi Hu, Beijing (CN); Feng Li, Beijing (CN)

(73) Assignee: BEIJING MABWORKS BIOTECH CO., LTD, Beijing (CN)

( * ) Notice: Subject to any disclaimer, the term of this patent is extended or adjusted under 35 U.S.C. 154(b) by 0 days.

(21) Appl. No.: 18/307,299

(22) Filed: Apr. 26, 2023

(65) Prior Publication Data
US 2023/0348630 A1    Nov. 2, 2023

(30) Foreign Application Priority Data
Apr. 28, 2022    (CN) .......................... 202210460302.1

(51) Int. Cl.
*C07K 16/46*    (2006.01)
*A61P 35/00*    (2006.01)

(52) U.S. Cl.
CPC ............ *C07K 16/468* (2013.01); *A61P 35/00* (2018.01); *C07K 2317/31* (2013.01); *C07K 2317/565* (2013.01)

(58) Field of Classification Search
CPC ............ C07K 16/468; C07K 2317/31; C07K 2317/565; C07K 2317/33; C07K 2317/622; C07K 2317/92; C07K 16/2809; C07K 16/2878; A61P 35/00
See application file for complete search history.

(56) References Cited

FOREIGN PATENT DOCUMENTS

| WO | 2017031104 A1 | 2/2017 |
|----|---------------|--------|
| WO | 2018083204 A1 | 5/2018 |
| WO | 2020018820 A1 | 1/2020 |
| WO | 2021104371 A1 | 6/2021 |

OTHER PUBLICATIONS

Demel et al. (2021), Focus on monoclonal antibodies targeting B-cell maturation antigen (BCMA) in multiple myeloma: update 2021. Br. J. Haematol., 193: 705-722. (Year: 2021).*
Lancman et al. (2020) Bispecifics, trispecifics, and other novel immune treatments in myeloma. Hematology Am Soc Hematol Educ Program. 2020(1):264-271. (Year: 2020).*
Garfall et al. Updated phase 1 results of teclistamab, a B-cell maturation antigen (BCMA) x CD3 bispecific antibody, in relapsed and / or refractory multiple myeloma. Blood (2020) 136 (Supp 1): 27. (Year: 2020).*
WIPO, International Search Report and Written Opinion for counterpart international application PCT/CN2023/090744, Jul. 20, 2023.
Cesar Rodriguez et al., Initial results of a phase I study of TNB-383B, a BCMA X CD3 bispecific T-cell redirecting antibody, in relapsed/refractory multiple myeloma, Blood, Nov. 5, 2020, vol. 136, Supplement 1, pp. 43-44.

* cited by examiner

*Primary Examiner* — Julie Wu
*Assistant Examiner* — Amber K Faust
(74) *Attorney, Agent, or Firm* — Duane Morris LLP; Thomas J. Kowalski

(57) ABSTRACT

Disclosed is a monoclonal antibody that specifically binds BCMA, or an antigen binding fragment thereof, and its use in treating cancers such as multiple myeloma. Also disclosed is a monoclonal antibody that specifically binds CD3, or an antigen binding fragment thereof, and its use in treating or alleviating an inflammatory disease, an autoimmune disease, or transplantation rejection. Further disclosed is an anti-BCMA/CD3 bispecific antibody, and its use in treating diseases such as cancers.

20 Claims, 12 Drawing Sheets

Specification includes a Sequence Listing.

A

B

D

E

F

ANTIBODIES BINDING BCMA AND CD3 AND USES THEREOF

INCORPORATION BY REFERENCE

This application claims priority to Chinese Patent Application No. 202210460302.1 filed on Apr. 28, 2022.

The foregoing application, and all documents cited therein or during its prosecution ("appln cited documents") and all documents cited or referenced herein (including without limitation all literature documents, patents, published patent applications cited herein) ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference. Any Genbank sequences mentioned in this disclosure are incorporated by reference with the Genbank sequence to be that of the earliest effective filing date of this disclosure.

SEQUENCE STATEMENT

The instant application contains a Sequence Listing XML labeled "55556-00098SequenceListingXML" which was created on Apr. 17, 2023 and is 59 bytes. The entire content of the sequence listing is incorporated herein by reference in its entirety.

FIELD OF THE INVENTION

The present disclosure relates an antibody or an antigen binding fragment thereof that specifically binds human and monkey BCMA, and its use in treating or alleviating cancers such as multiple myeloma, as well as an antibody or an antigen binding fragment thereof that binds human CD3, particularly CD3δ/ε, and its use in treatment or alleviation of an inflammatory disease, an autoimmune disease, or transplantation rejection. The present disclosure also provides a bispecific molecule targeting BCMA and CD3 that comprises the anti-BCMA antibody or antigen binding fragment thereof of the disclosure and the anti-CD3 antibody or antigen binding fragment thereof of the disclosure, and its use in treating cancers.

BACKGROUND OF THE INVENTION

Multiple myeloma (MM) is a disease where the plasma cells in the bone marrow overgrow to crowd out normal blood-forming cells and produce abnormal proteins that cause organ or tissue damages. It, along with leukemia and lymphoma, is the most commonly seen systematic blood cancer, and the lifetime risk of getting such a disease is about 9 in 100,000 in the United States, and 1 in 100,000 in China. Generally, MM is common for ages 60 and older and more common in males, with bond injuries, hypercalcemia, anemia, and/or kidney damage occurring in most cases.

In recent years, in despite of the development of chemotherapies, protease inhibitors, immune modulators and anti-CD38 antibodies, a lot of MM patients were unresponsive or showed resistance after the initial treatment stage. Up till now, there is no treatments that can guarantee a cure from this disease. Therefore, new therapies or therapeutics are needed in the art.

B cell maturation antigen (BCMA) is a hot target for multiple myeloma treatment.

BCMA and BCMA-Targeted Therapy

B cell maturation antigen, also referred to as CD269 or TNFRSF17, is a type I transmembrane protein and a member of the tumor necrosis factor receptor (TNFR) superfamily. It along with BAFF-receptor (BAFFR) and TACI, the members of the same superfamily, plays an important role in regulating B cell proliferation and survival (Rickert R. C et al., (2011) *Immunological Reviews* 244(1):115-133).

BCMA is mainly expressed on mature B lymphocytes and plasma cells, with minimal expression in hematopoietic stem cells or nonhematopoietic tissues. Its ligands include BAFF and APRIL, of which APRIL has a higher BCMA binding affinity. When engaged with BAFF and/or APRIL, BCMA initiates NF-κB and MAPK8/JNK signaling pathways, promoting the survival of the bone marrow plasma cells and plasmablasts, especially the long-lived bone marrow plasma cells, and supporting humoral immunity. The membrane-bound BCMA molecules may shed from the cell surface with the γ-secretase and circulate in the body as soluble BCMAs (sBCMA), resulting in reduced BCMA activation on the cell surface (Laurent S A et al., (2015) *Nat Commun.* 6:7333).

BCMA overexpression has been found on the surface of the malignant plasma cells in the bone marrow of MM patients. BCMA enables survival of malignant plasma cells in the bone marrow, and the APRIL-BCMA signaling in these cells supports cell proliferation, evasion from apoptosis, and production of potent immune-inhibitory molecules such as IL-10, PD-L1 and TGF-β (Tai Y-T et al., (2016) *Blood.* 127(25):3225-3236). Studies have shown that BCMA overexpression and activation are associated with MM progress in multiple animal models and human patients, and the soluble BCMA molecules may inhibit BAFF activity through complex formation, causing MM-associated immunodeficiency (Tai Y-T et al., (2016) Supra; Sanchez E et al., (2016)*Clin Cancer Res.* 22:3383-3397).

Compared to the CD138 molecules which are uniquely expressed by the plasma cells but disappear rapidly from the cell surfaces, the membrane BCMA is evidently a better biomarker for malignant plasma cells. As it can be readily detected in frozen samples, the membrane BCMA can be used for the diagnosis, disease progress monitoring, treatment efficacy monitoring, and prognosis of MM. The soluble BCMA is also a good MM biomarker, for monitoring patients' responses to the therapies, and a high soluble BCMA level indicates a poor prognosis (Shah N et al., (2020), *Leukemia* 34(4): 985-1005).

Due to BCMA's selective expression and distribution pattern, i.e., widely expressed on the MM cells but with very low to no expression on normal cells, and its long serum half-life, it has become a hot therapeutic target for MM and other hematological malignancies.

The current BCMA-targeting therapies mainly involve bispecific antibodies, antibody-drug conjugates (ADC) and chimeric antigen receptor (CAR)-T cells.

One type of the bispecific antibody is the bispecific T-cell engager (BiTE) which specifically binds the target cells and the T cells, redirecting the T cells to the target cells.

T Cells and CD3

The CD3 molecule is a biomarker for the T cells. It forms a TCR-CD3 complex with a T cell receptor (TCR), to play key roles in antigen recognition and signal transduction. A TCR molecule consists of an alpha (α) chain and a beta (β) chain, or a gamma (γ) chain and a delta (δ) chain. Each chain contains an extracellular variable region responsible for binding the antigenic peptide, an extracellular constant region proximal to the cell membrane, and a short cytoplasmic tail. Due to the short cytoplasmic tail, the TCR requires CD3 to mediate signal transduction. A CD3 molecule is composed of a gamma (γ) chain, a delta (δ) chain, two epsilon (ε) chains, and two zeta (ζ) chains, forming three dimers εγ, εδ and ζζ in the TCR/CD3 complex. The intracellular tails of CD3γ, CD3δ, CD3ε and CD3ζ chains contain 10 immunoreceptor tyrosine-based activation motifs (ITAM) in total, the phosphorylation of which enables the CD3 chains bind to ZAP70, a kinase important in T cell signaling cascade.

An anti-CD3 antibody may form a bispecific molecule with a functional moiety targeting a disease associated antigen such as a tumor associated antigen. The bispecific molecule physically links T cells with the disease associated antigens, resulting in activation of T cells around the disease associated cells and later T cell-mediated target cell death. For instance, a bispecific molecule specific to both the CD3 molecule and a tumor associated antigen may pull T cells closer to the tumor cells, such that the T cells are activated to release supramolecular attack particles (SMAP) containing more than 280 proteins, including granzymes and perforins, where the perforins form pores on the plasma membrane of target cells that mediate entry of granzymes into the target cell cytoplasm (Š. Bálint et al., (2020) Science 368 (6493): 897-901).

The anti-CD3 antibodies may cluster around the T cells to simulate TCR-MHC-antigen peptide interaction so as to trigger TCR signaling, secreting cytokines such as IL-2, IFN-γ and TNF-α, which promote T cell proliferation and differentiation. T cell proliferation and differentiation, on one side, provides more T cells to kill tumor cells, and on the other side, causes severe toxicities, i.e., cytokine release syndrome (CRS), in subjects receiving anti-CD3 therapy. Clinical signs and symptoms of CRS include fever, nausea, headache, rash, rapid heartbeat, low blood pressure, and trouble breathing, mild or life threatening. For example, CRS was observed in the clinical trial of OKT3, a monospecific anti-CD3 antibody, and the CRS was believed to be related to cross-linking of antibodies through binding to Fc receptors (FcRs) (Herold K C et al., (2003) *J Clin Invest.* 111(3):409-418). Therefore, in subsequent antibody development, the Fc regions of anti-CD3 antibodies such as Teplizumab were engineered to have weak FcR binding capability.

Similarly, severe CRS and neurological toxicities occurred frequently in the clinical trials of Blincyto® blinatumomab, a bispecific T cell engager antibody against CD19 and CD3. Obviously, the modification to the Fc regions is not applicable to the bispecific anti-CD3 antibodies, as the binding of the non-CD3 binding domain to a target cell renders antibody cross-linking, inducing abundant cytokine release by T cells.

Bispecific Antibody Targeting BCMA and CD3

The bispecific antibody targeting BCMA and CD3 may, on one hand, bind to the BCMAs on cancer cells, and on the other hand bind to the CD3s on T cells, resulting in T cell recruitment to the cancer sites and thus causing cancer cell death.

However, as described above, the anti-CD3 bispecific antibodies are quite cytotoxic. Several clinical trials involving anti-BCMA/CD3 antibodies, including AMG701 and Elranatamab, discontinued in the first half of Year 2021 due to severe side effects.

Therefore, there is an urgent need for anti-BCMA/CD3 bispecific antibodies with potent anti-tumor efficacy and little to no cytotoxicity. The construction of such antibodies needs both an anti-CD3 antibody that causes less cytokine release problem and a good molecule design that optimizes the effects as produced by the anti-CD3 antibody and the anti-BCMA antibody, such that a wider therapeutic window may be found.

Citation or identification of any document in this application is not an admission that such document is available as prior art to the present invention.

SUMMARY OF THE INVENTION

The inventors of the application, with efforts, have found an antibody or an antigen binding fragment thereof that specifically binds human and monkey BCMAs, which, as compared to the prior art antibodies such as the BCMA binding portion of EM801, has comparable, if not higher, human/monkey BCMA binding affinity/activity, even in the presence of free BCMA molecules.

The inventors of the application further found an anti-CD3 antibody or an antigen binding fragment thereof, that binds CD3δ/ε but not CD3δ or CDε alone. T cell activation is only stimulated when several copies of such anti-CD3 antibodies or antigen binding fragments thereof of the disclosure are cross-linked, and bispecific antibodies containing the anti-CD3 antibody or antigen binding fragment thereof of the disclosure have potent targeted killing activity with lower adverse side effects as compared to the prior art antibodies such as the CD3 binding portion of EM801.

Thus, in a first aspect, the disclosure provides an isolated monoclonal antibody (e.g., a human antibody) or an antigen binding fragment thereof, that binds BCMA, which may comprise (i) a heavy chain variable region comprising a VH CDR1, a VH CDR2 and a VH CDR3 that may comprise amino acid sequences having at least 85%, 86%, 87%, 88%, 89%, 90%, 91%, 92%, 93%, 94%, 95%, 96%, 97%, 98%, 99% or 100% sequence identity to SEQ ID NOs: 1, 2 and 3, respectively, and/or (ii) a light chain variable region comprising a VL CDR1, a VL CDR2 and a VL CDR3 that may comprise amino acid sequences having at least 85%, 86%, 87%, 88%, 89%, 90%, 91%, 92%, 93%, 94%, 95%, 96%, 97%, 98%, 99% or 100% sequence identity to SEQ ID NOs: 4, 5 and 6, respectively.

The heavy chain variable region may comprise an amino acid sequence having at least 85%, 86%, 87%, 88%, 89%, 90%, 91%, 92%, 93%, 94%, 95%, 96%, 97%, 98%, 99% or 100% sequence identity to SEQ ID NO: 7.

The light chain variable region may comprise an amino acid sequence having at least 85%, 86%, 87%, 88%, 89%, 90%, 91%, 92%, 93%, 94%, 95%, 96%, 97%, 98%, 99% or 100% sequence identity to SEQ ID NO: 8 or 40.

In certain embodiments, the antibody or antigen binding fragment thereof may comprise a heavy chain variable region and a light chain variable region that may comprise amino acid sequences having at least 85%, 86%, 87%, 88%, 89%, 90%, 91%, 92%, 93%, 94%, 95%, 96%, 97%, 98%, 99% or 100% sequence identity to (1) SEQ ID NOs: 7 and 8, respectively, or (2) SEQ ID NOs: 7 and 40, respectively.

The antibody or the antigen binding fragment thereof of the disclosure may comprise a heavy chain constant region and/or a light chain constant region. The heavy chain constant region may be with FcR binding affinity, such as IgG1 heavy chain constant region, e.g., human IgG1 heavy chain constant region comprising the amino acid sequence of SEQ ID NO: 17 (X1=L, X2=L, X3=N, X4=T, X5=L, X6=Y). The light chain constant region may be κ or λ light chain constant region, such as human κ light chain constant region comprising the amino acid sequence of SEQ ID NO: 18.

The antibody or the antigen binding fragment thereof of the disclosure, in certain embodiments, may be of IgG1, IgG2, IgG3 or IgG4 isotype. In certain embodiments, the antibody or the antigen binding fragment thereof of the disclosure may be a single chain variable fragment (scFv) antibody, or antibody fragments, such as Fab or F(ab')$_2$ fragments. The antibody or the antigen binding fragment thereof of the disclosure may be human or humanized.

The disclosure also provides an immunoconjugate that may comprise the anti-BCMA antibody or antigen binding fragment thereof of the disclosure linked to a therapeutic agent such as a cytotoxin or an anti-cancer agent. The disclosure further provides a bispecific molecule that may comprise the anti-BCMA antibody, or the antigen binding fragment thereof, of the disclosure, linked to a second functional moiety (e.g., a second antibody) having a different binding specificity than said antibody, or antigen binding fragment thereof. In another aspect, the antibody or the antigen binding portion thereof of the present disclosure may be made into part of a chimeric antigen receptor (CAR) or an engineered T cell receptor (TCR). Also provided is an immune cell that may comprise the CAR and/or the TCR, such as a T cell and a NK cell. The antibody or the antigen binding portion thereof of the disclosure can also be encoded by or used in conjunction with an oncolytic virus.

In a second aspect, the disclosure provides an isolated monoclonal antibody (e.g., a human antibody) or an antigen binding fragment thereof, that binds CD3 especially CD3δ&ε, which may comprise (i) a heavy chain variable region comprising a VH CDR1, a VH CDR2 and a VH CDR3 that may comprise amino acid sequences having at least 85%, 86%, 87%, 88%, 89%, 90%, 91%, 92%, 93%, 94%, 95%, 96%, 97%, 98%, 99% or 100% sequence identity to 1) SEQ ID NOs: 9, 10 and 11, respectively; 2) SEQ ID NOs: 26, 27 (X1=T, X2=T, J=I) and 28 (X1=N, X2=F), respectively; 3) SEQ ID NOs: 41, 27 X1=s, X2=S, J=L) and 28 (X1=R, X2=Y), respectively; or 4) SEQ ID NOs: 42, 27 (X1=H, X2=H, J=I) and 28 (X1=N, X2=Y), respectively, and/or (ii) a light chain variable region comprising a VL CDR1, a VL CDR2 and a VL CDR3 that may comprise amino acid sequences having at least 85%, 86%, 87%, 88%, 89%, 90%, 91%, 92%, 93%, 94%, 95%, 96%, 97%, 98%, 99% or 100% sequence identity to 1) SEQ ID NOs: 12, 13 and 14, respectively; 2) SEQ ID NOs: 29 (X1=Q, X2=R, X3=V), 30 (X1=R, X2=Q) and 31 (X1=S, X2=I, X3=Q), respectively; 3) SEQ ID NOs: 29 (X1=R, X2=L, X3=V), 30 (X1=K, X2=Y) and 31 (X1=Q, X2=I, X3=T), respectively; or 4) SEQ ID NOs: 29 (X1=R, X2=R, X3=L), 30 (X1=K, X2=P) and 31 (X1=H, X2=T, X3=R), respectively.

The anti-CD3 antibody or antigen binding fragment thereof of the disclosure may comprise a heavy chain variable region and a light chain variable region, wherein the VH CDR1, VH CDR2, VH CDR3, VL CDR1, VL CDR2 and VL CDR3 may comprise amino acid sequences having at least 85%, 86%, 87%, 88%, 89%, 90%, 91%, 92%, 93%, 94%, 95%, 96%, 97%, 98%, 99% or 100% sequence identity to 1) SEQ ID NOs: 9, 10, 11, 12, 13 and 14, respectively; 2) SEQ ID NOs: 26, 27 (X1=T, X2=T, J=I), 28 (X1=N, X2=F), 29 (X1=Q, X2=R, X3=V), 30 (X1=R, X2=Q), and 31 (X1=s, X2=I, X3=Q), respectively; 3) SEQ ID NOs: 41, 27 (X1=S, X2=S, J=L), 28 (X1=R, X2=Y), 29 (X1=R, X2=L, X3=V), 30 (X1=K, X2=Y) and 31 (X1=Q, X2=I, X3=T), respectively; or 4) SEQ ID NOs: 42, 27 (X1=H, X2=H, J=I), 28 (X1=N, X2=Y), 29 (X1=R, X2=R, X3=L), 30 (X1=K, X2=P) and (X1=H, X2=T, X3=R), respectively.

The heavy chain variable region may comprise an amino acid sequence having at least 85%, 86%, 87%, 88%, 89%, 90%, 91%, 92%, 93%, 94%, 95%, 96%, 97%, 98%, 99% or 100% sequence identity to SEQ ID NOs: 15 or 32 (X1=S, X2=D, X3=T, X4=T, X5=T, J=I, X6=N, X7=F; X1=D, X2=S, X3=S, X4=S, X5=S, J=L, X6=R, X7=Y; or X1=G, X2=D, X3=A, X4=H, X5=H, J=I, X6=N, X7=Y).

The light chain variable region may comprise an amino acid sequence having at least 85%, 86%, 87%, 88%, 89%, 90%, 91%, 92%, 93%, 94%, 95%, 96%, 97%, 98%, 99% or 100% sequence identity to SEQ ID NO: 16 or 33 (X1=Q, X2=R, X3=V, X4=R, X5=Q, X6=S, X7=I, X8=Q; X1=R, X2=L, X3=V, X4=K, X5=Y, X6=Q, X7=I, X8=T; or X1=R, X2=R, X3=L, X4=K, X5=P, X6=H, X7=T, X8=R).

In certain embodiments, the antibody or antigen binding fragment thereof may comprise a heavy chain variable region and a light chain variable region that may comprise amino acid sequences having at least 85%, 86%, 87%, 88%, 89%, 90%, 91%, 92%, 93%, 94%, 95%, 96%, 97%, 98%, 99% or 100% sequence identity to 1) SEQ ID NOs: 15 and 16, respectively; 2) SEQ ID NOs: 32 (X1=S, X2=D, X3=T, X4=T, X5=T, J=I, X6=N, X7=F), 33 (X1=Q, X2=R, X3=V, X4=R, X5=Q, X6=S, X7=I, X8=Q), respectively; 3) SEQ ID NOs: 32 (X1=D, X2=S, X3=S, X4=S, X5=S, J=L, X6=R, X7=Y) and 33 (X1=R, X2=L, X3=V, X4=K, X5=Y, X6=Q, X7=I, X8=T), respectively; or 4) SEQ ID NOs: 32 (X1=G, X2=D, X3=A, X4=H, X5=H, J=I, X6=N, X7=Y) and 33 (X1=R, X2=R, X3=L, X4=K, X5=P, X6=H, X7=T, X8=R), respectively.

The anti-CD3 antibody or the antigen binding fragment thereof of the disclosure may comprise a heavy chain constant region and/or a light chain constant region. In certain embodiments, the anti-CD3 antibody or the antigen binding fragment thereof of the disclosure may comprise a heavy chain constant region with reduced or weak FcR binding affinity and/or a light chain constant region. In certain embodiments, the anti-CD3 antibody or the antigen binding fragment thereof of the disclosure may comprise a heavy chain constant region with no FcR binding affinity and/or a light chain constant region. The heavy chain constant region with weak or no FcR binding affinity may be the heavy chain constant region of human IgG1 (N297A), human IgG1 (L234A+L235A), human IgG1 (L234A+L235A+P329G), human IgG1 (L234A+L235A+N297A) (such as SEQ ID NO: 17 (X1=A, X2=A, X3=A, X4=T, X5=L, X6=Y), human IgG1 (L234A+L235A+N297A+P329G), human IgG2 (V234A+V237A), human IgG1 (L234A+V235E), or a functional fragment thereof. The light chain constant region may be κ or λ light chain constant region, such as human κ or λ light chain constant region, such as human κ constant region comprising the amino acid sequence of SEQ ID NO: 18.

In certain embodiments, the antibody or the antigen binding fragment thereof of the disclosure may be a single chain variable fragment (scFv) antibody, or antibody fragments, such as Fab or F(ab')$_2$ fragments. The antibody or the antigen binding fragment thereof of the disclosure may be human or humanized.

The disclosure also provides a bispecific molecule that may comprise the anti-CD3 antibody, or the antigen binding fragment thereof, of the disclosure, linked to a second functional moiety (e.g., a second antibody) having a different binding specificity than said antibody, or antigen binding fragment thereof, e.g., a second functional moiety against a disease associated antigen.

In certain embodiments, the bispecific molecule may target CDR and a disease associated antigen. In certain embodiments, the disease associated antigen is a tumor associated antigen, such as CD20, CD19, CD22, CD4, CD24, CD38, CD123, CD228, CD138, BCMA, GPC3, CEA, CD276, gp100, 5T4, GD2, EGFR, MUC-1, PSMA, EpCAM, MCSP, SM5-1, MICA, MICB, ULBP and HER-2. In certain embodiments, the disease associated antigen is an infectious disease associated antigen such as CD4, BHsAg, LMP-1 and LMP2. In certain embodiments, the disease associated antigen is an inflammatory disease associated antigen such as IL17R and CD6. In certain embodiments, the disease associated antigen is BCMA.

In a third aspect, the disclosure provides a bispecific molecule targeting BCMA and CD3, comprising a BCMA binding domain, and a CD3 binding domain, wherein the BCMA binding domain may comprise the anti-BCMA antibody or antigen binding fragment thereof of the disclosure, the CD3 binding domain may comprise the anti-CD3 antibody or antigen binding fragment thereof of the disclosure.

The bispecific molecule, in certain embodiments, may be a recombinant protein containing two antigen binding domains linked via a linker. In certain embodiments, the two binding domains may be linked with or without a linker in e.g., scFv-scFv, Fab-Fab, Fv-Fv or scFv-Fab (Fv) formats.

The bispecific molecule of the disclosure may contain one CD3 binding domain, and one to four BCMA binding domains. In one embodiment, the bispecific molecule may contain one CD3 binding domain, and two BCMA binding domains. In one embodiment, the BCMA binding domain is an anti-BCMA antibody or an antigen binding fragment thereof, e.g., an Fv and/or a scFv, of the disclosure. In one embodiment, the CD3 binding domain may be an anti-CD3 antigen or an antigen binding fragment thereof, e.g., an Fv or Fab, of the disclosure. The two BCMA binding domains may bind to the same or different antigen epitopes, may contain the same or different domain sequences, and/or may be in the same or different antigen-binding domain formats.

The bispecific molecule of the disclosure targeting CD3 and BCMA may be an IgG like antibody.

In one embodiment, the bispecific molecule may comprise:
i) a first polypeptide, containing an anti-BCMA heavy chain variable region and a heavy chain constant region,
ii) a second polypeptide, containing an anti-BCMA light chain variable region,
iii) a third polypeptide, containing an anti-BCMA heavy chain variable region, an anti-BCMA light chain variable region, an anti-CD3 heavy chain variable region, and a heavy chain constant region, and
iv) a fourth polypeptide, containing an anti-CD3 light chain variable region,
wherein the anti-BCMA heavy chain variable region in the first polypeptide and the anti-BCMA light chain variable region in the second polypeptide may associate to form a BCMA binding domain, the anti-BCMA heavy chain variable region and the anti-BCMA light chain variable region in the third polypeptide may associate to form a BCAM binding domain, the anti-CD3 heavy chain variable region in the third polypeptide and the anti-CD3 light chain variable region in the fourth polypeptide may associate to form a CD3 binding domain, and the heavy chain constant region in the first polypeptide and the heavy chain constant region in the third polypeptide are associated together via e.g., the knobs-into-holes approach, the covalent bond(s) and/or the disulfide bond(s).

The heavy chain constant region in the first polypeptide may be a hole variant, such as human IgG1 heavy chain constant region or a functional fragment thereof with T366S/L368A/Y407V mutation. The heavy chain constant region in the first polypeptide may be a hole variant with weak or no FcR binding affinity, such as human IgG1 heavy chain constant region comprising the amino acid sequence of SEQ ID NO: 17 (X1=A, X2=A, X3=A, X4=S, X5=A, X6=V). The heavy chain constant region in the third polypeptide may be a knob variant, such as human IgG1 heavy chain constant region or a functional fragment thereof with T366W mutation. The heavy chain constant region in the third polypeptide may be a knob variant with weak or no FcR binding affinity, such as human IgG1 heavy chain constant region comprising the amino acid sequence of SEQ ID NO: 17 (X1=A, X2=A, X3=A, X4=W, X5=L, X6=Y).

Alternatively, the heavy chain constant region in the first polypeptide may be a knob variant, such as human IgG1 heavy chain constant region or a functional fragment thereof with T366W mutation. The heavy chain constant region in the first polypeptide may be a knob variant with weak or no FcR binding affinity, such as human IgG1 heavy chain constant region comprising the amino acid sequence of SEQ ID NO: 17 (X1=A, X2=A, X3=A, X4=W, X5=L, X6=Y). The heavy chain constant region in the third polypeptide may be a hole variant, such as human IgG1 heavy chain constant region or a functional fragment thereof with T366S/L368A/Y407V mutations. The heavy chain constant region in the third polypeptide may be a hole variant with weak or no FcR binding affinity, such as human IgG1 heavy chain constant region comprising the amino acid sequence of SEQ ID NO: 17 (X1=A, X2=A, X3=A, X4=S, X5=A, X6=V).

The anti-BCMA heavy chain variable region and the anti-BCMA light chain variable region in the third polypeptide may be linked with a linker to form a scFv format. In one embodiment, the anti-BCMA scFv may be modified in the framework regions of the light chain variable region to enhance the conformational stability. In one embodiment, anti-BCMA scFv may contain VL comprising the amino acid sequence of SEQ ID NO: 40. In one embodiment, the linker may be a peptide of about 5 to 30 amino acid residues. In one embodiment, the linker may be a peptide of about 10 to 30 amino acid residues. In one embodiment, the linker may be a peptide of about 10 to 20 amino acid residues. In one embodiment, the linker may be a GS linker comprising the amino acid sequence of e.g., SEQ ID NO: 19.

The anti-BCMA heavy chain variable region or the anti-BCMA light chain variable region in the third polypeptide may be linked via a linker to the anti-CD3 heavy chain variable region. In one embodiment, the linker may be a peptide of about 5 to 30 amino acid residues. In one embodiment, the linker may be a peptide of about 10 to 30 amino acid residues. In one embodiment, the linker may be a peptide of about 10 to 15 amino acid residues. In one embodiment, the linker may be a GS linker having the amino acid sequence of e.g., SEQ ID NO: 20.

In one embodiment, the first polypeptide comprises, from N terminus to C terminus, the anti-BCMA heavy chain variable region and the heavy chain constant region. The heavy chain constant region in the first polypeptide may be a hole variant. The third polypeptide comprises, from N terminus to C terminus, the anti-BCMA heavy chain variable region, the anti-BCMA light chain variable region, the anti-CD3 heavy chain variable region, and the heavy chain constant region; or alternatively the anti-BCMA light chain variable region, the anti-BCMA heavy chain variable region, the anti-CD3 heavy chain variable region, and the heavy chain constant region. The heavy chain constant region in the third polypeptide may be a knob variant.

The second polypeptide may comprise a light chain constant region at the C terminus, such as human κ constant region comprising the amino acid sequence of SEQ ID NO: 18.

The fourth polypeptide may comprise a light chain constant region at the C terminus, such as human κ constant region comprising the amino acid sequence of SEQ ID NO: 18.

The first, second, third and fourth polypeptides, in certain embodiments, may comprise amino acid sequences having at least at least 85%, 86%, 87%, 88%, 89%, 90%, 91%, 92%, 93%, 94%, 95%, 96%, 97%, 98%, 99% or 100% sequence identity to 1) SEQ ID NOs: 38, 39, 34 and 35, respectively; 2) SEQ ID NOs: 38, 39, 36 (X1=S, X2=D, X3=T, X4=T, X5=T, J=I, X6=N, X7=F), and 37 (X1=Q, X2-R, X3=V, X4=R, X5=Q, X6=S, X7=I, X8=Q), respectively; 3) SEQ ID NOs: 38, 39, 36 (X1=D), X2=S, X3=S, X4=S, X5=S, J=L, X6=R, X7=Y) and 37 (X1=R, X2=L, X3=V, X4=K, X5=Y, X6=Q, X7=I, X8=T), respectively; or 4) SEQ ID NOs: 38, 39, 36 (X1=G, X2=D, X3=A, X4=H, X5=H, J=I, X6=N, X7=Y) and 37 (X1=R, X2=R, X3=L, X4=K, X5=P, X6=H, X7=T, X8=R).

In another embodiment, the bispecific molecule may comprise:
  i) a first polypeptide, containing an anti-BCMA heavy chain variable region and a heavy chain constant region,
  ii) a second polypeptide, containing an anti-BCMA light chain variable region,
  iii) a third polypeptide, containing an anti-CD3 heavy chain variable region, and a heavy chain constant region, and
  iv) a fourth polypeptide, containing an anti-BCMA heavy chain variable region, an anti-BCMA light chain variable region, and an anti-CD3 light chain variable region,
  wherein the anti-BCMA heavy chain variable region in the first polypeptide and the anti-BCMA light chain variable region in the second polypeptide may associate to form a BCMA binding domain, the anti-CD3 heavy chain variable region in the third polypeptide and the anti-CD3 light chain variable region in the fourth polypeptide may associate to form a CD3 binding domain, the anti-BCMA heavy chain variable region and the anti-BCMA light chain variable region in the fourth polypeptide may associate to form a BCMA binding domain, and the heavy chain constant region in the first polypeptide and the heavy chain constant region in the third polypeptide are associated together via e.g., the knobs-into-holes approach, the covalent bond(s) and/or the disulfide bond(s).

In one embodiment, the first polypeptide comprises, from N terminus to C terminus, the anti-BCMA heavy chain variable region and the heavy chain constant region. In one embodiment, the third polypeptide comprises, from N terminus to C terminus, the anti-CD3 heavy chain variable region, and the heavy chain constant region. In one embodiment, the fourth polypeptide comprises, from N terminus to C terminus, the anti-BCMA heavy chain variable region, the anti-BCMA light chain variable region and the anti-CD3 light chain variable region; the anti-BCMA light chain variable region, the anti-BCMA heavy chain variable region, and the anti-CD3 light chain variable region; the anti-CD3 light chain variable region, the anti-BCMA light chain variable region, and the anti-BCMA heavy chain variable region; or alternatively the anti-CD3 light chain variable region, the anti-BCMA heavy chain variable region, and the anti-BCMA light chain variable region.

With respect to the heavy chain constant regions in the first and third polypeptides, one is a knob variant, such as human IgG1 heavy chain constant region or a functional fragment thereof with T366W mutation, e.g., human IgG1 heavy chain constant region with knob mutation(s) and weak or no FcR binding affinity comprising the amino acid sequence of SEQ ID NO: 17 (X1=A, X2=A, X3=A, X4=W, X5=L, X6=Y), and the other is a hole variant, such as human IgG1 heavy chain constant region or a functional fragment thereof with T366S/L368A/Y407V mutations, e.g., human IgG1 heavy chain constant region with hole mutation(s) and weak or no FcR binding affinity comprising the amino acid sequence of SEQ ID NO: 17 (X1=A, X2=A, X3=A, X4=S, X5=A, X6=V).

The anti-BCMA heavy chain variable region and the anti-BCMA light chain variable region in the fourth polypeptide may be linked via a linker. The anti-BCMA heavy chain variable region or the anti-BCMA light chain variable region in the fourth polypeptide may be linked via a linker to the anti-CD3 light chain variable region. In one embodiment, the linker may be a peptide of about 5 to 30 amino acid residues. In one embodiment, the linker may be a peptide of about 10 to 30 amino acid residues. In one embodiment, the linker may be a peptide of about 10 to 15 amino acid residues. In one embodiment, the linker between the anti-BCMA heavy chain variable region and the anti-BCMA light chain variable region may be a GS linker comprising e.g., the amino acid sequence of SEQ ID NO: 19. In one embodiment, the linker between the anti-BCMA heavy or light chain variable region and the anti-CD3 light chain variable region may be a GS linker comprising e.g., the amino acid sequence of SEQ ID NO: 20.

The bispecific antibody may contain a light chain constant region at the C terminus of the anti-BCMA light chain variable region and/or the anti-CD3 light chain variable region. The light chain constant region at the C terminus of the anti-BCMA light chain variable region may be human κ light chain constant region comprising e.g., the amino acid sequence of SEQ ID NO: 18. The light chain constant region at the C terminus of the anti-CD3 light chain variable region may be human κ light chain constant region comprising e.g., the amino acid sequence of SEQ ID NO: 18.

The disclosure further provides the first, second, third and fourth polypeptides, and the half-antibodies formed by these polypeptides.

The anti-BCAM/CD3 bispecific antibody of the disclosure has higher CD3 binding activity and comparable target cell killing activity, but causes cytokine release at a lower level, as compared to prior art antibodies such as EM801.

Nucleic acid molecules encoding the anti-BCMA antibody or the antigen binding fragment thereof, the immunoconjugate, CAR or TCR comprising the anti-BCMA antibody or antigen binding fragment thereof, the anti-CD3 antibody or the antigen binding fragment thereof, the bispecific antibody comprising the anti-BCMA antibody or antigen binding fragment thereof and/or the anti-CD3 antibody or antigen binding fragment thereof, of the disclosure, are also encompassed by the disclosure, as well as expression vectors that may comprise such nucleic acids and host cells that may comprise such expression vectors or have the nucleic acid molecules integrated into the genome. A method for preparing the molecules mentioned above, including the antibodies or antigen binding fragments thereof, using the host cell is also provided, that may comprise steps of (i) expressing the molecules in the host cell and (ii) isolating the molecules from the host cell or its cell culture.

Compositions, e.g., pharmaceutical compositions, that may comprise the anti-BCMA antibody or the antigen binding fragment thereof, the immunoconjugate, or the cell bearing CAR or TCR comprising the anti-BCMA antibody or the antigen binding fragment thereof, the anti-CD3 antibody or the antigen binding fragment thereof, the bispecific molecule comprising the anti-BCMA and/or anti-CD3 antibody or antigen binding fragment thereof, the nucleic acid molecule, the expression vector, or the host cell, and optionally a pharmaceutically acceptable carrier, are also provided.

In a fourth aspect, the present disclosure provides a method for treating or alleviating a BCMA associated disease in a subject in need thereof, comprising administering to the subject a therapeutically effective amount of the pharmaceutical composition comprising the anti-BCMA antibody or antigen binding fragment thereof, the immunoconjugate, or the cell bearing CAR or TCR comprising the anti-BCMA antibody or the antigen binding fragment thereof, the nucleic acid molecule, the expression vector, or the host cell, of the disclosure. The BCMA associated disease includes, but not limited to, multiple myeloma, and other hematological malignancies such as plasmacytoma, plasma cell leukemia, macroglobulinemia, solitary plasmacytoma, and extramedullary plasmacytoma.

The disclosure also provides a method for treating or alleviating an inflammatory disease, an autoimmune disease, or transplantation rejection in a subject in need thereof, comprising administering to the subject a therapeutically effective amount of the pharmaceutical composition comprising the anti-CD3 antibody or antigen binding fragment thereof of the disclosure. In certain embodiments, the inflammatory disease is multiple sclerosis (MS), or inflammatory bowel disease (IBD) (such as Crohn's disease). In certain embodiments, the autoimmune disease is type I diabetes. In certain embodiments, the anti-CD3 antibody or antigen binding fragment thereof of the disclosure may be orally administered to the subject.

The disclosure further provides the use of the anti-CD3 antibody or antigen binding fragment thereof in the preparation of a bispecific antibody targeting CD3 and a disease associated antigen. The disease associated antigen may be a tumor associated antigen, such as BCMA, CD19, CD22, CD4, CD24, CD38, CD123, CD228, CD138, BCMA, GPC3, CEA, CD276, gp100, 5T4, GD2, EGFR, MUC-1, PSMA, EpCAM, MCSP, SM5-1, MICA, MICB, ULBP, and HER-2. In certain embodiments, the disease associated antigen may be an infectious disease associated antigen, such as CD4, HBsAg, LMP-1 and LMP2. In certain embodiments, the disease associated antigen may be an inflammatory disease associated antigen, such as IL17R and CD6.

The disclosure further provides a method for treating or alleviating a disease in a subject in need thereof using the bispecific molecule of the disclosure targeting CD3 and a disease associated antigen, comprising administering to the subject a therapeutically effective amount of the pharmaceutical composition of the disclosure comprising the bispecific molecule of the disclosure. The disease may be a tumor, an infectious disease, or an inflammatory disease, depending on the disease associated antigen to which the bispecific molecule binds.

In a fifth aspect, the disclosure provides a method for treating or alleviating a BCMA associated disease in a subject in need thereof, comprising administering to the subject a therapeutically effective amount of the pharmaceutical composition of the disclosure comprising the anti-BCMA/CD3 bispecific molecule. The BCMA associated disease includes, but not limited to, multiple myeloma, and other hematological malignancies such as plasmacytoma, plasma cell leukemia, macroglobulinemia, solitary plasmacytoma, and extramedullary plasmacytoma.

Other features and advantages of the instant disclosure will be apparent from the following detailed description and examples, which should not be construed as limiting. The contents of all references, Genbank entries, patents and published patent applications cited throughout this application are expressly incorporated herein by reference.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

BRIEF DESCRIPTION OF THE DRAWINGS

The following detailed description, given by way of example, but not intended to limit the invention solely to the specific embodiments as described, may best be understood in conjunction with the accompanying drawings.

Figure 5:
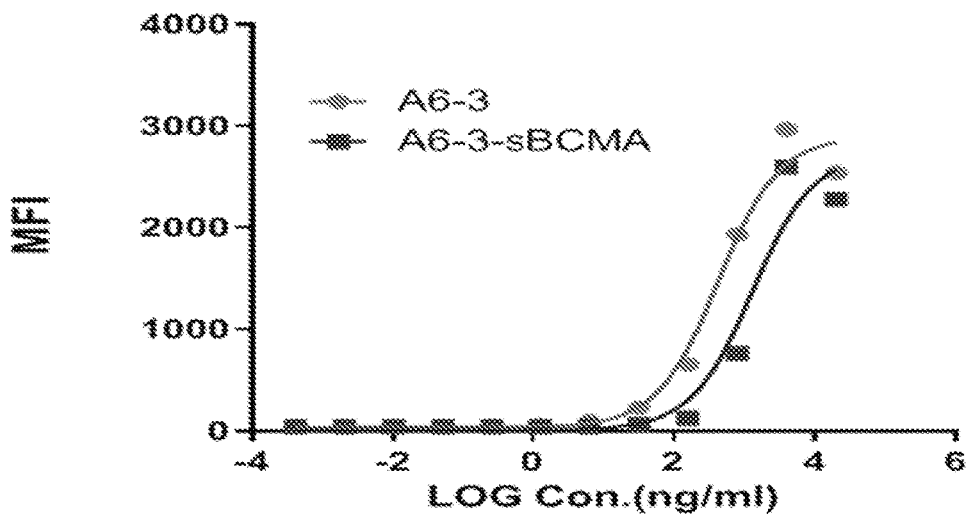

FIG. 5 shows the effect of the free BCMA molecules (sBCMA) on the anti-BCMA antibody-membrane BCMA interaction.

Figure 6:
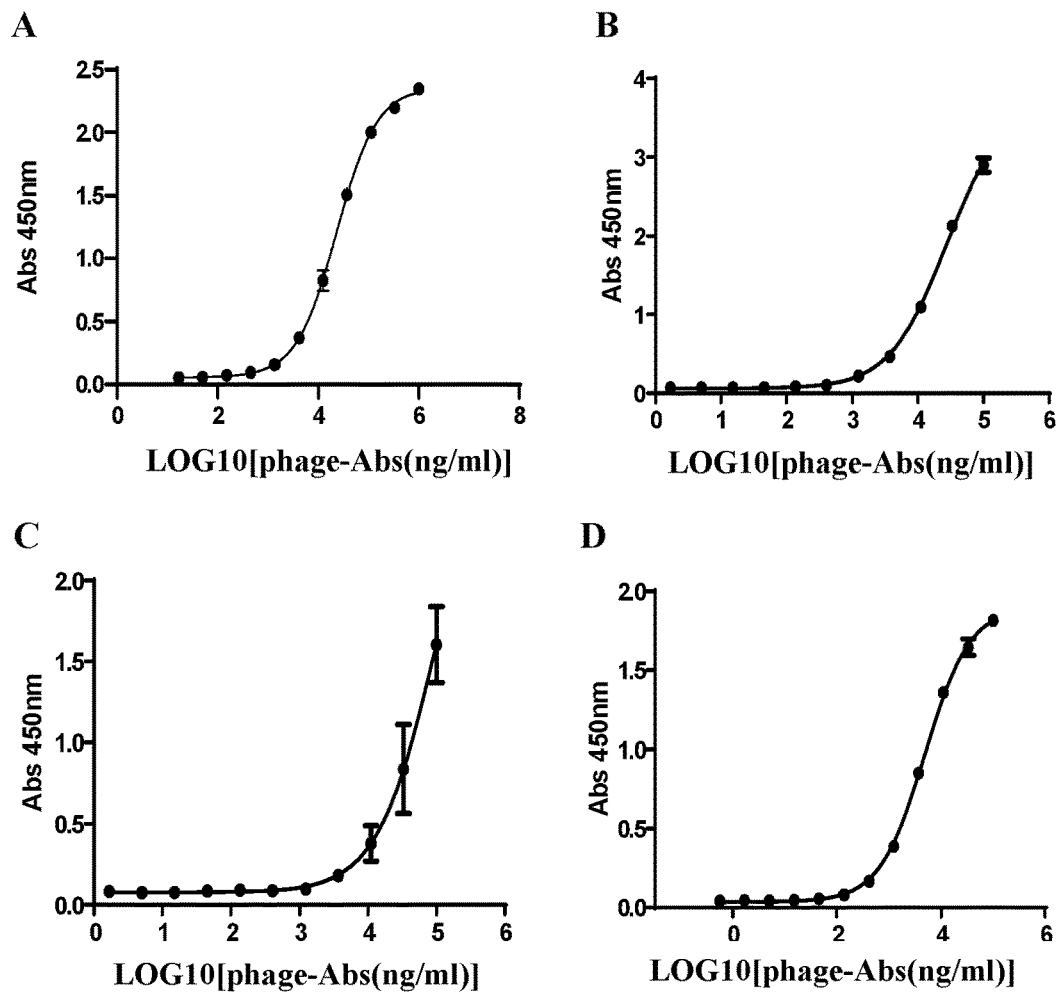

FIG. 6 shows the binding activity of the anti-CD3 antibodies D1E9 (A), D8E5 (B), D12A4 (C) and 7-1A12 (D) displayed on phages to the CD3D&E complex.

Figure 7:
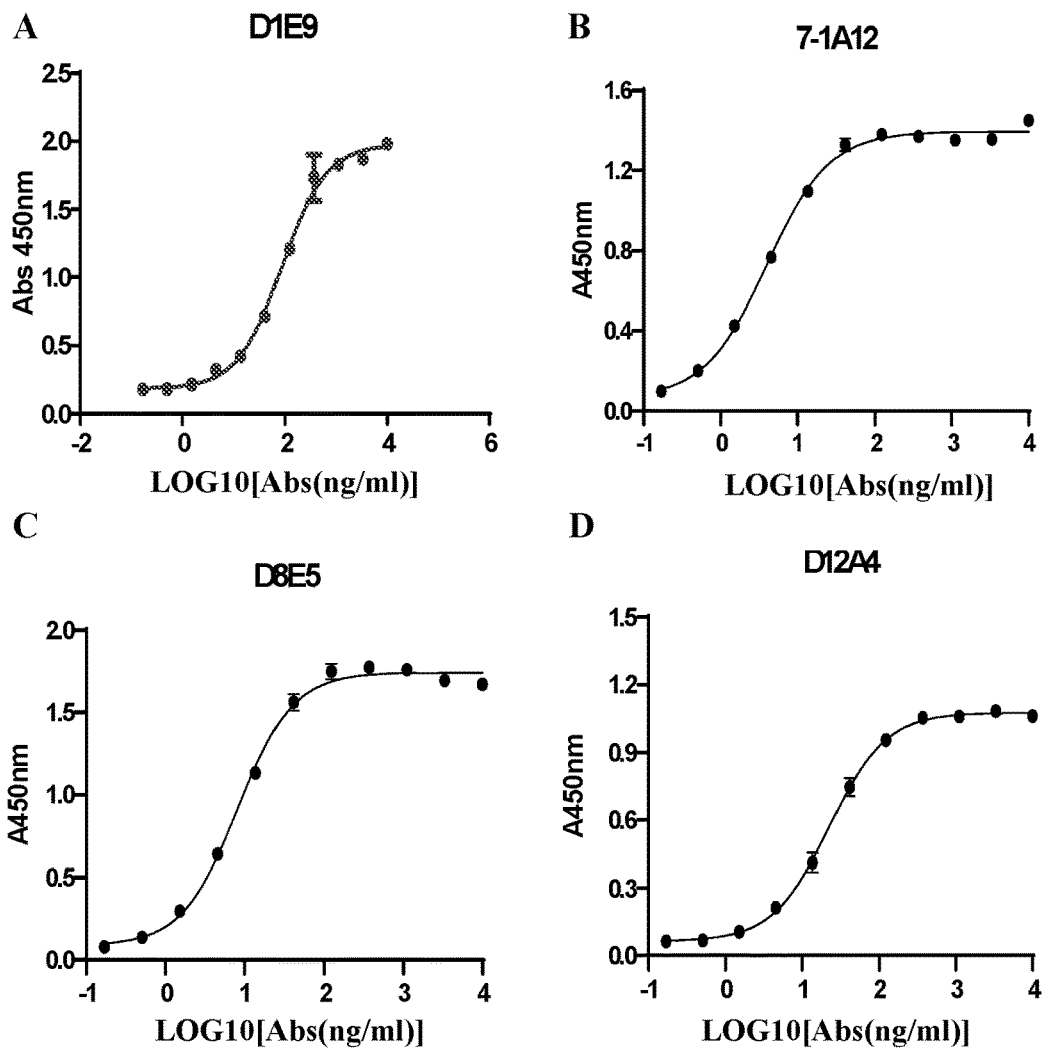

FIG. 7 shows the binding activity of the anti-CD3 antibodies D1E9 (A), 7-1A12 (B), D8E5 (C), and D12A4 (D) to the CD3D&E complex.

Figure 8:
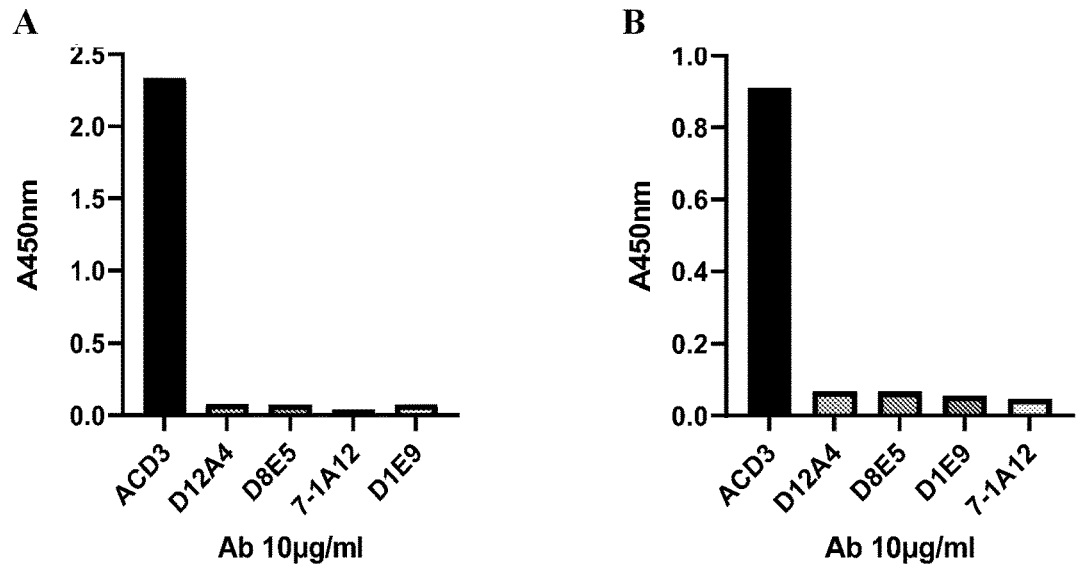

FIG. 8 shows the binding activity of the anti-CD3 antibodies to CD3E (A) and CD3D (B).

Figure 9:
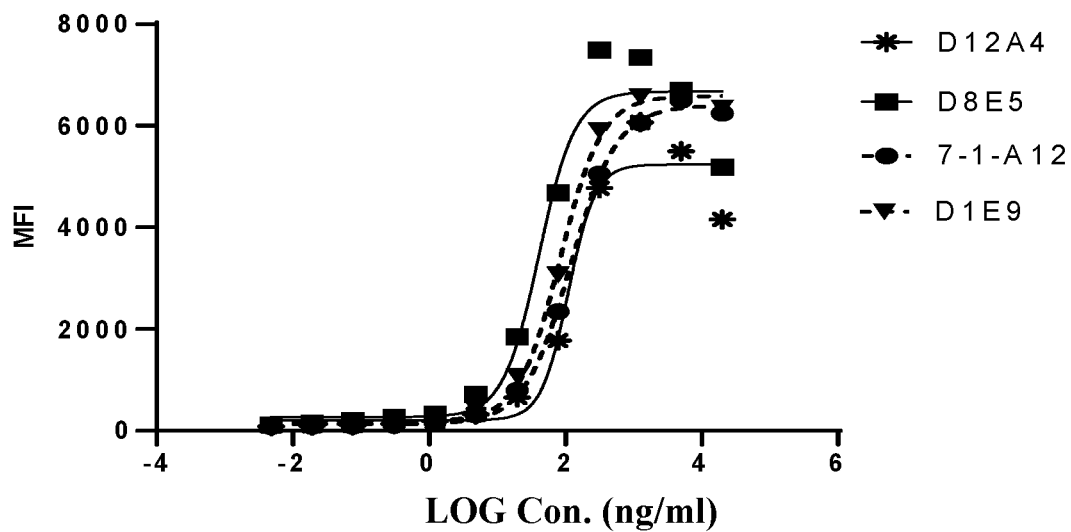

FIG. 9 shows the binding activity of the anti-CD3 antibodies to Jurkat cells.

Figure 10:
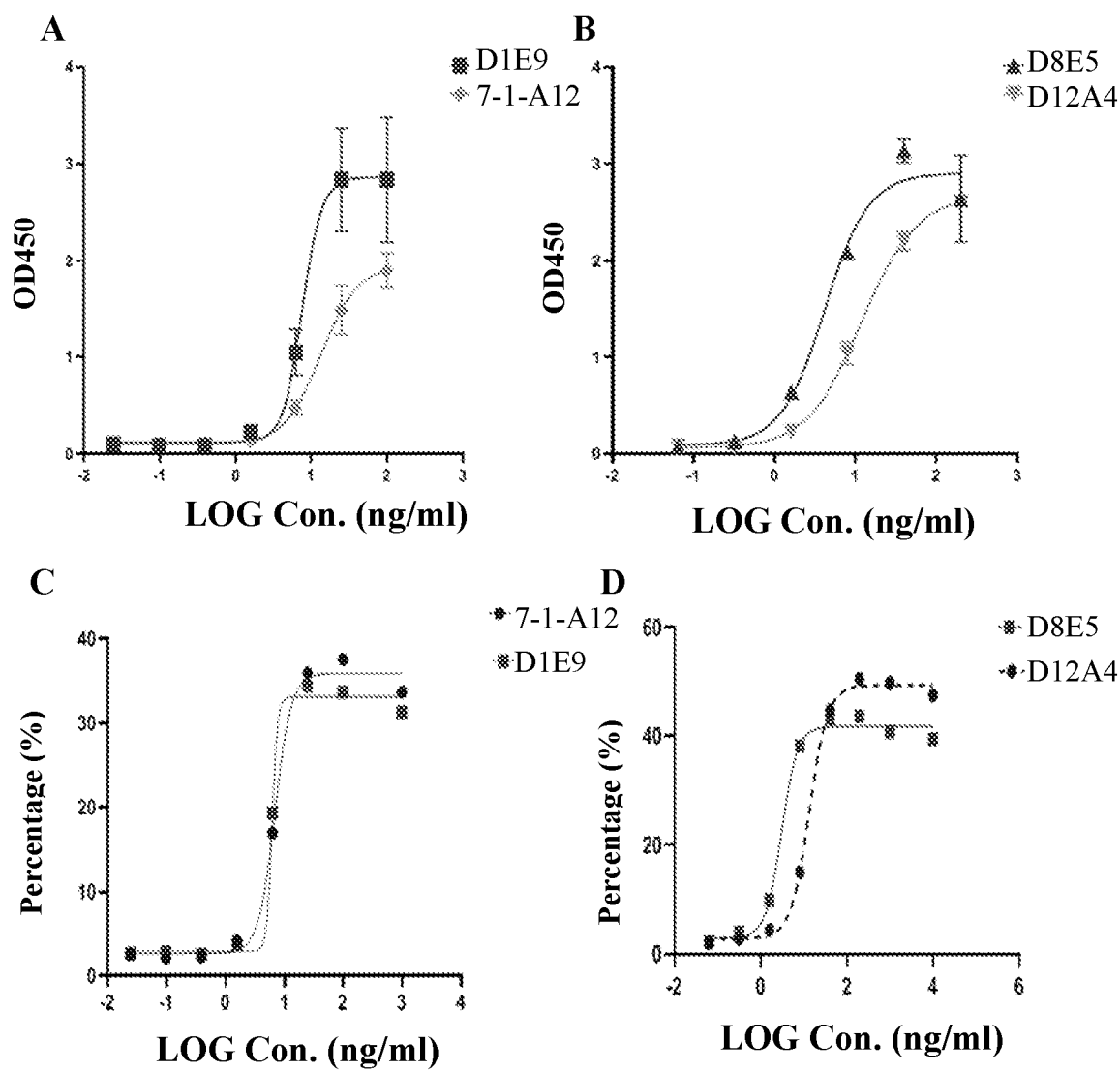

FIG. 10 shows the ability of the cross-linked anti-CD3 antibodies to activate primary human T cells as measured by the interferon γ secretion level (A, B) and CD69 expression level (C, D).

Figure 11:
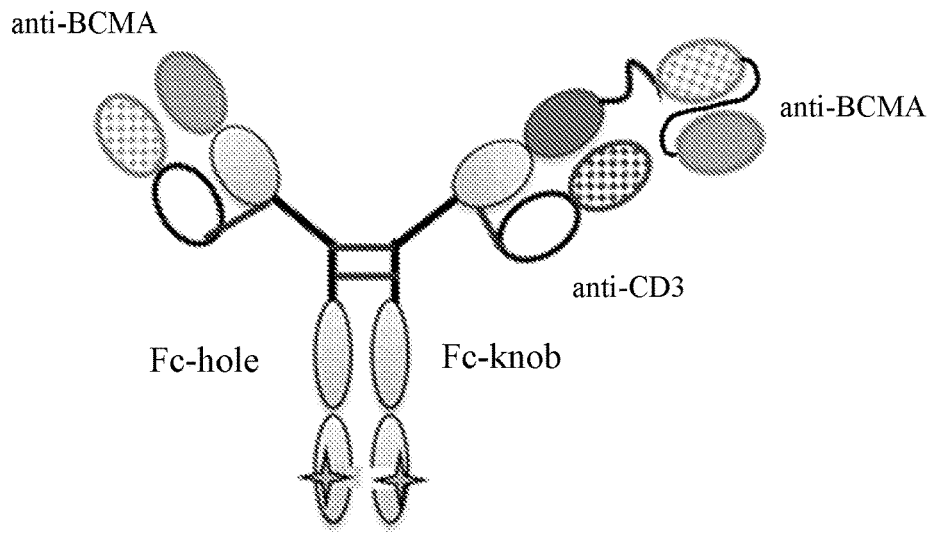

FIG. 11 is the schematic drawing of the exemplary anti-CD3/BCMA bispecific antibody.

Figure 12:
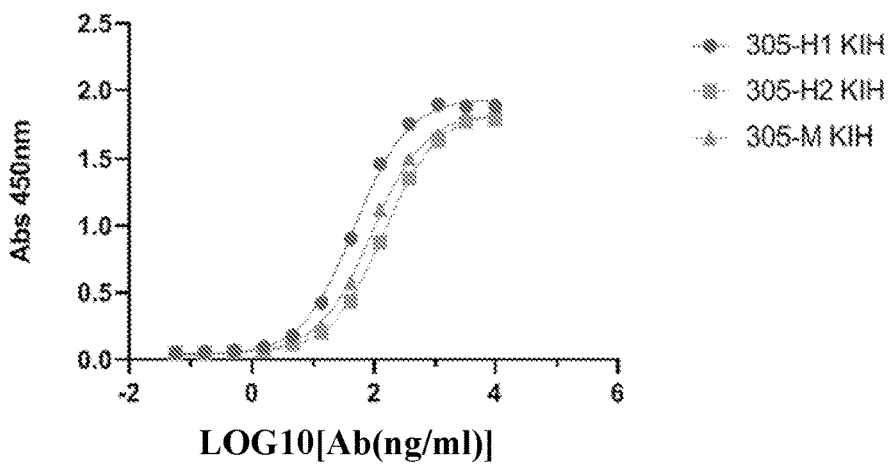
Figure 12:
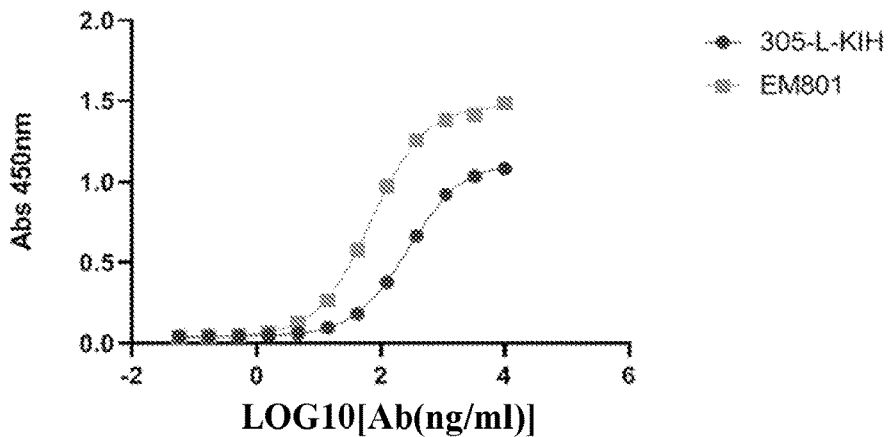

FIG. 12 shows the binding activity of the anti-CD3/BCMA bispecific antibodies 305-H1 KIH, 305-H2 KIH, 305-M KIH (A) and 305-L-KIH (B) to CD3D&E.

Figure 13:
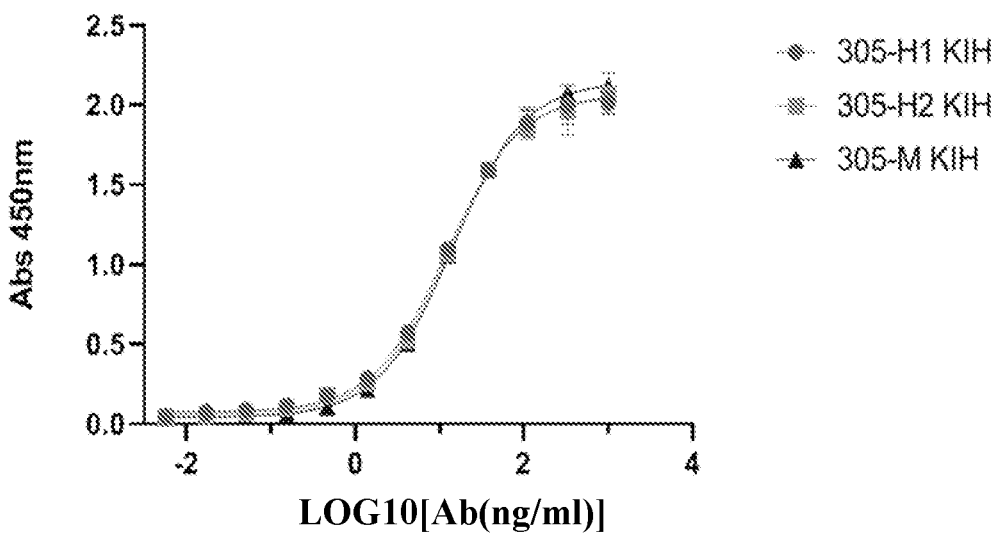
Figure 13:
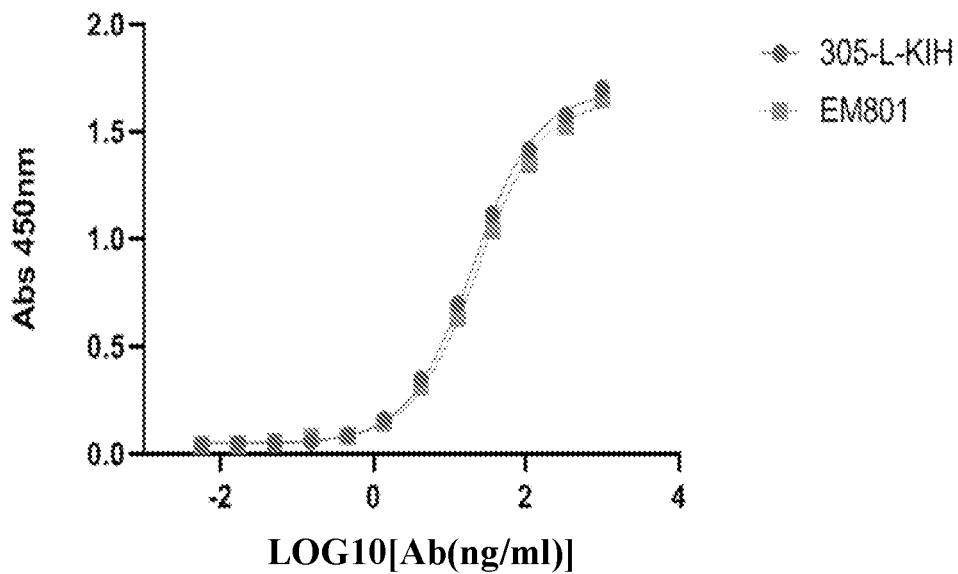

FIG. 13 shows the binding activity of the anti-CD3/BCMA bispecific antibodies 305-H1 KIH, 305-H2 KIH, 305-M KIH (A) and 305-L-KIH (B) to human BCMA.

Figure 14:
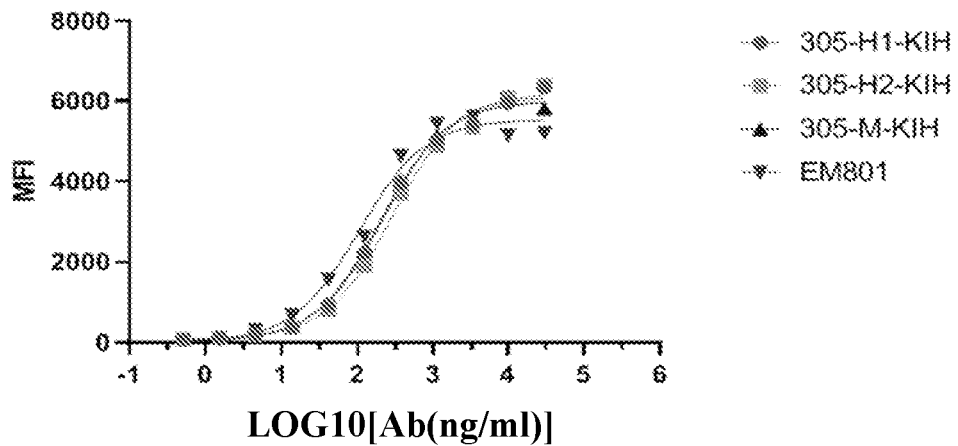
Figure 14:
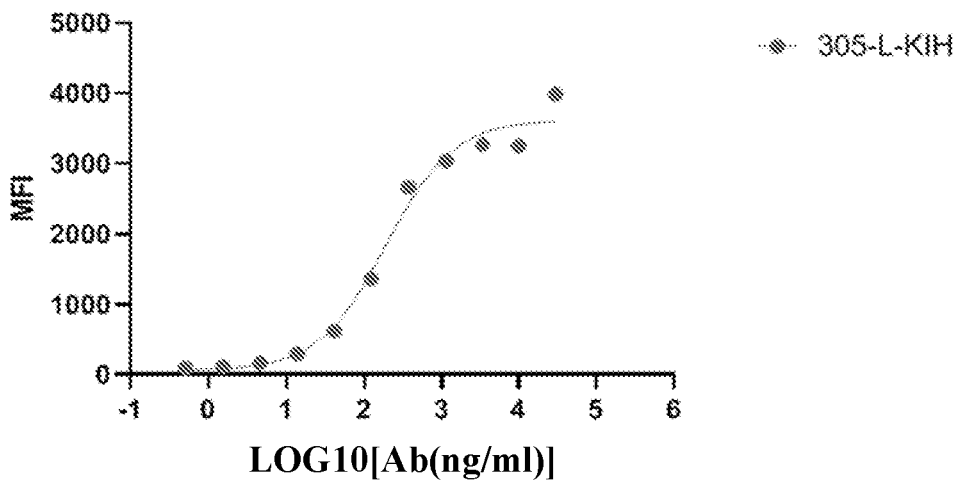
Figure 14:
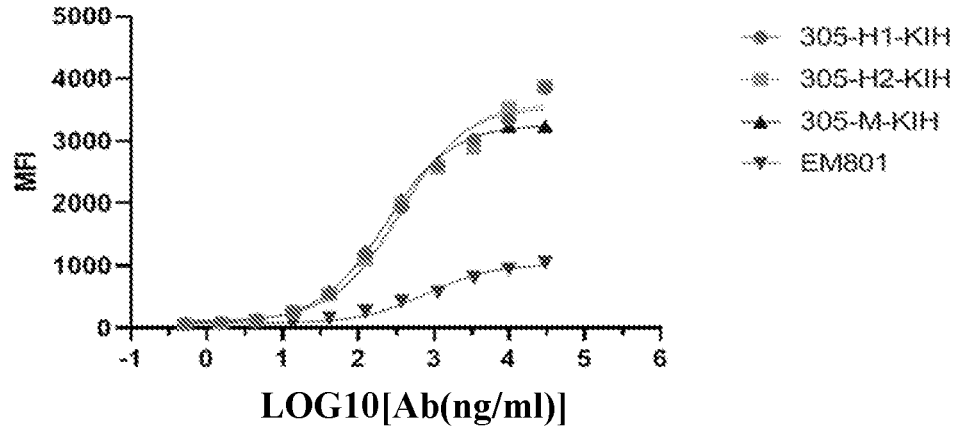
Figure 14:
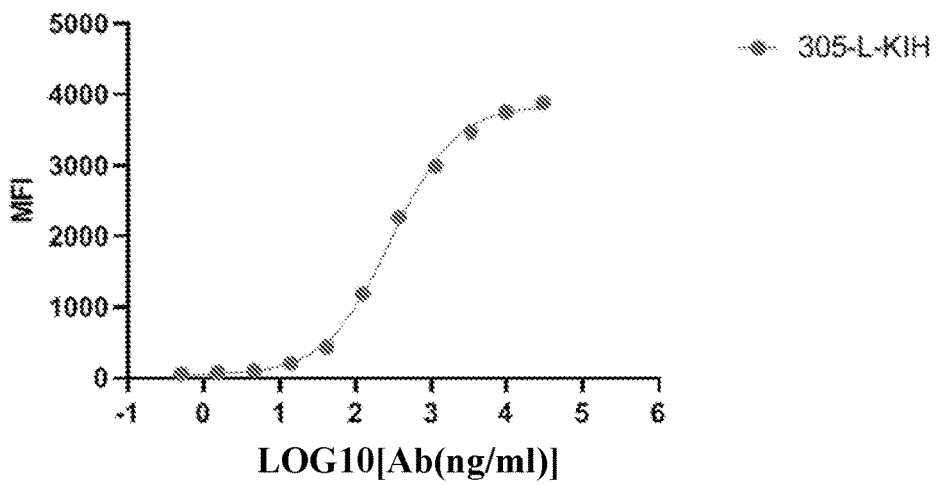
Figure 14:
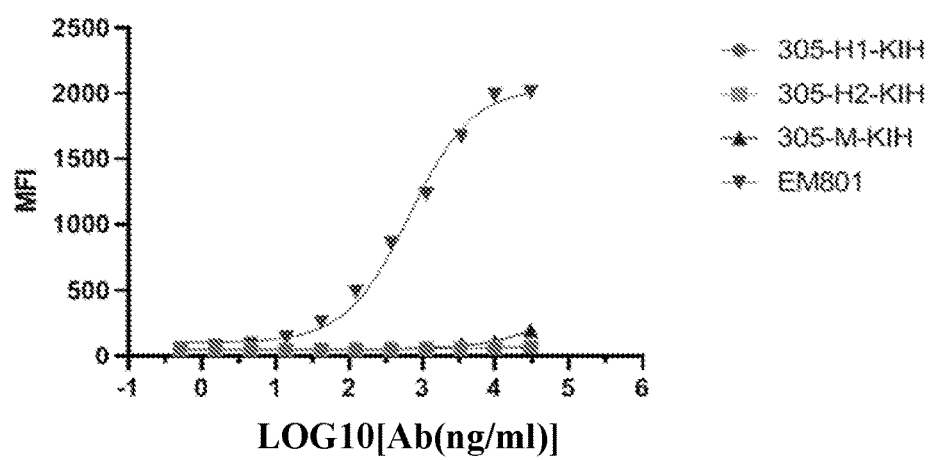
Figure 14:
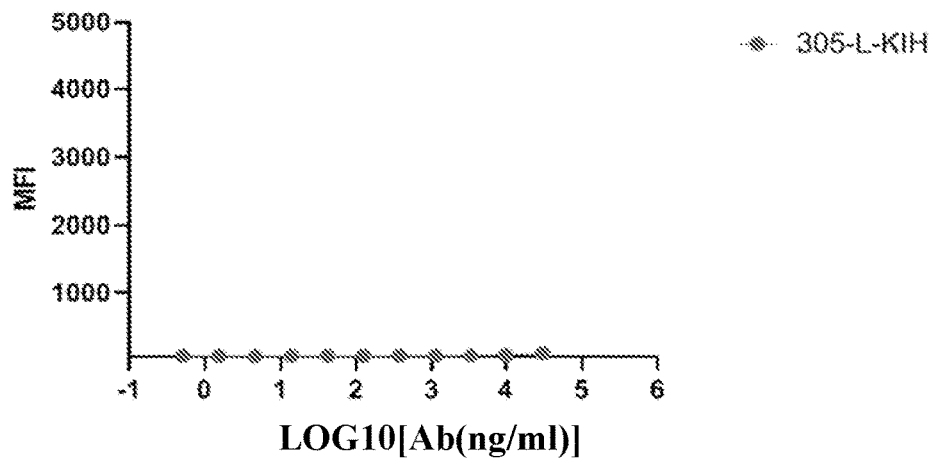

FIG. 14 shows the binding activity of the anti-CD3/BCMA bispecific antibodies to HEK293A/human BCMA cells (A, B), HEK293A/monkey BCMA cells (C, D) and HEK293A/mouse BCMA cells (E, F).

Figure 15:
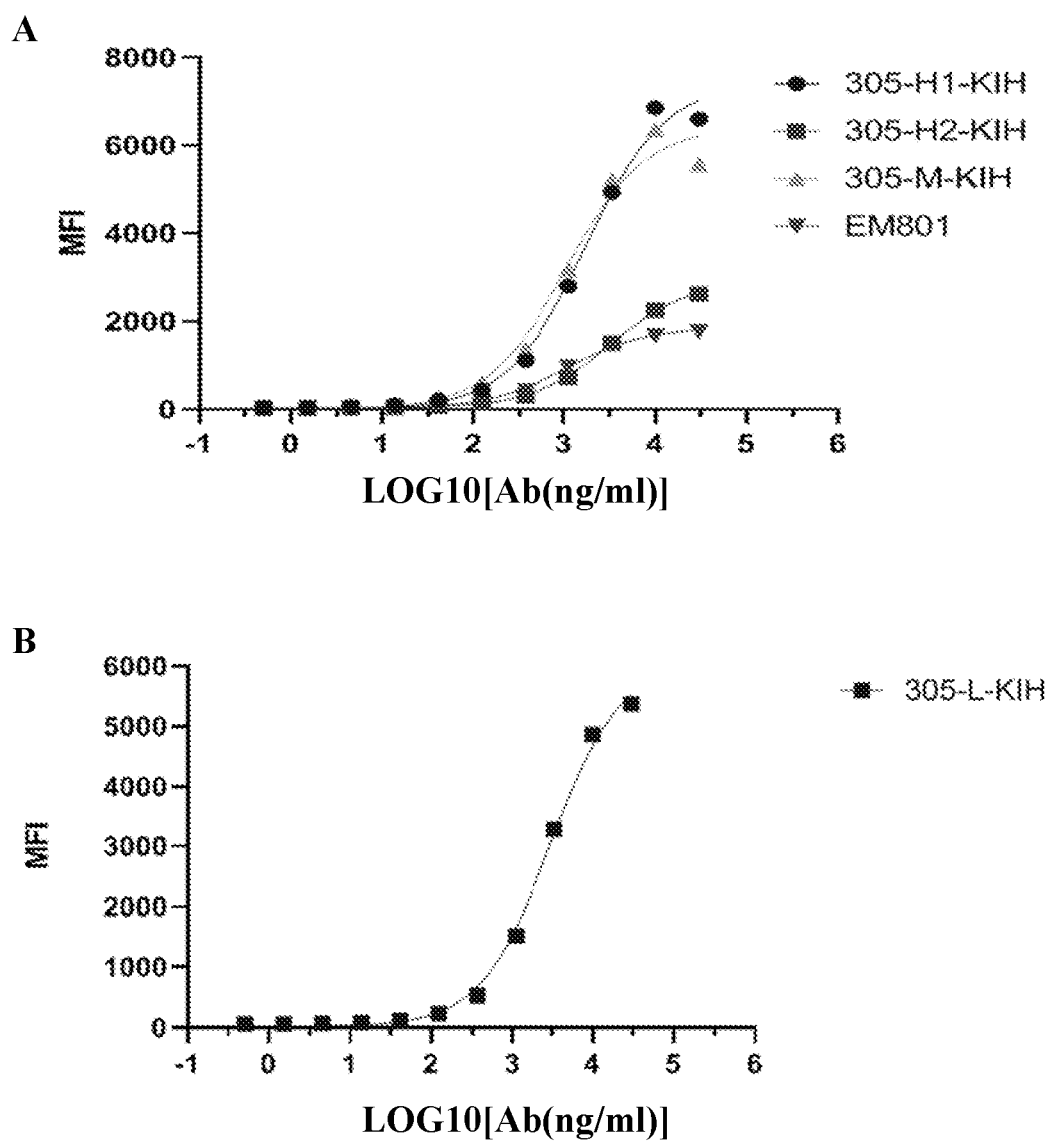

FIG. 15 shows the binding activity of the anti-CD3/BCMA bispecific antibodies 305-H1 KIH, 305-H2 KIH, 305-M KIH (A) and 305-L-KIH (B) to Jurkat cells.

Figure 16:
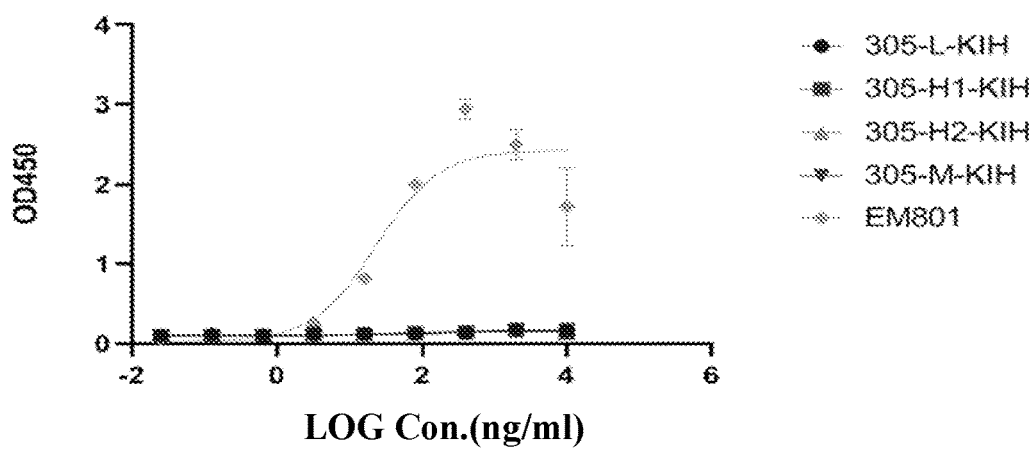
Figure 16:
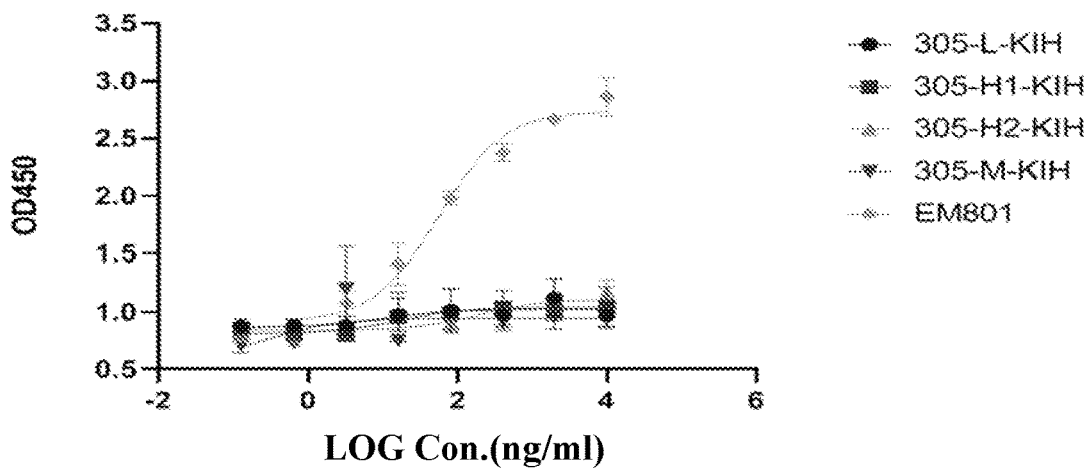
Figure 16:
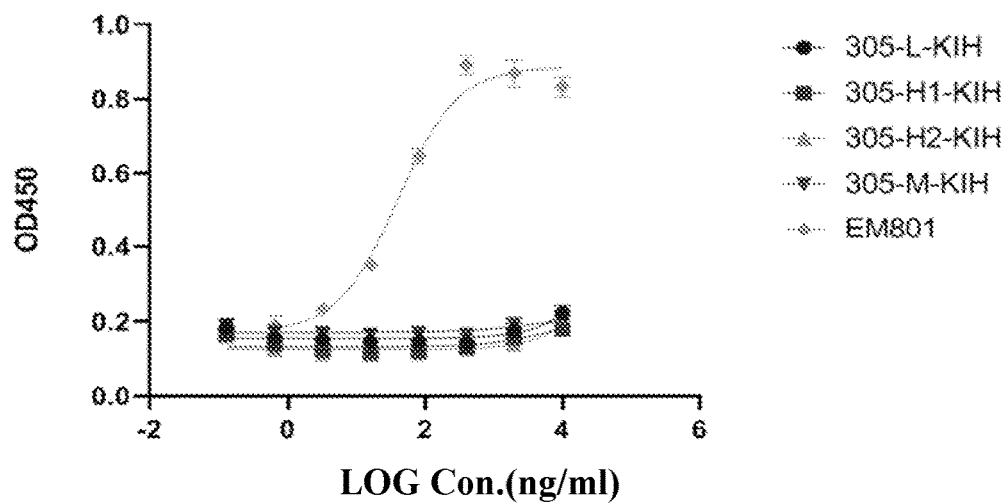

FIG. 16 shows the effect of the anti-CD3/BCMA bispecific antibodies on T cell activation, as measured by the secretion levels of IFN-γ (A), IL-6 (B) and TNF-α (C).

Figure 17:
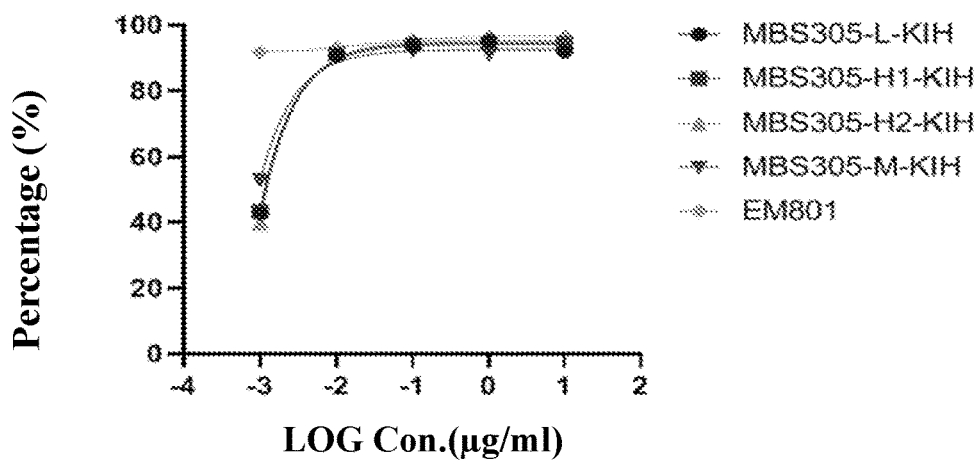
Figure 17:
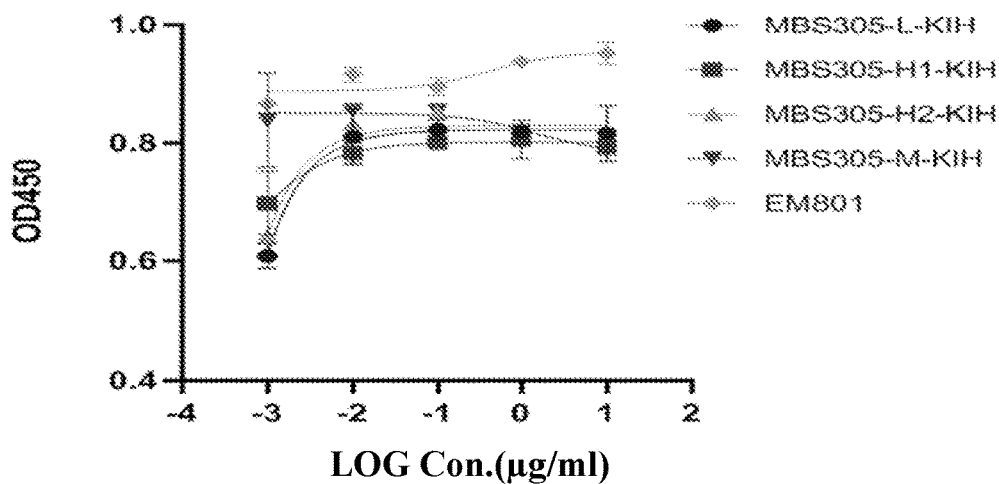
Figure 17:
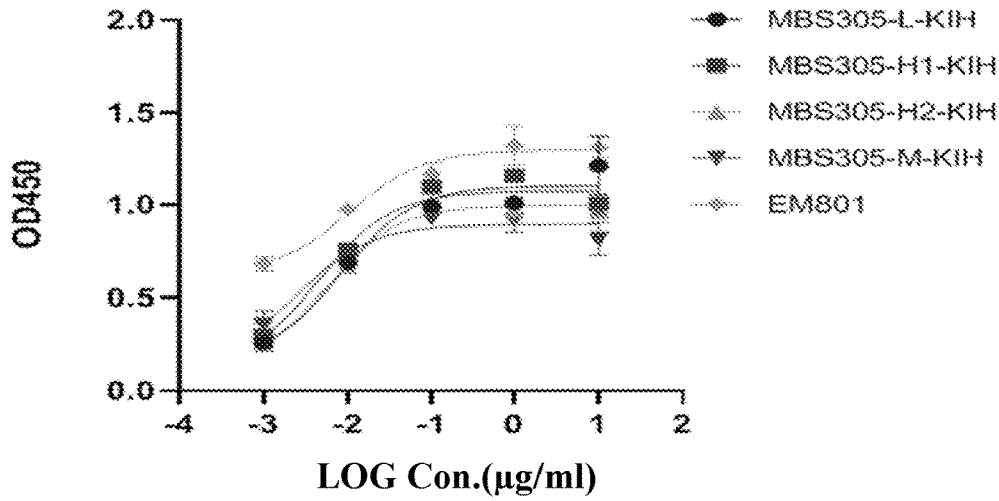

FIG. 17 shows the ability of the anti-CD3/BCMA bispecific antibodies to trigger PBMC-mediated BCMA+ tumor cell death (A) and to activate secretion of IL-6 (B) and TNF-α (C) by T cells.

DETAILED DESCRIPTION OF THE INVENTION

To ensure that the present disclosure may be more readily understood, certain terms are first defined. Additional definitions are set forth throughout the detailed description.

The term "CD3" refers to cluster of differentiation 3, comprising the γ, δ, ε and ζ chains. The term "CD3ε" or "CD3E" refers to the ε chain of the CD3 molecule. The term "CD3δ" or "CD3D" refers to the δ chain of the CD3 molecule. The term "CD3D&E" or "CD3δ&ε" refers to the complex formed by the δ chain and the ε chain. These terms may comprise variants, isoforms, homologs, orthologs and paralogs.

The term "BCMA" refers to B cell maturation antigen, over-expressed by malignant plasma cells. The term "human BCMA" refers to the BCMA protein having the amino acid sequence from human beings, such as the amino acid sequence of SEQ ID NO: 21. The term "monkey BCMA" refers to the BCMA protein having the amino acid sequence from monkeys, such as the amino acid sequence of SEQ ID NO: 22. The term "mouse BCMA" refers to the BCMA protein having the amino acid sequence from mice, such as the amino acid sequence of SEQ ID NO: 23.

The term "antibody" as referred to herein includes IgG, IgA, IgD, IgE and IgM whole antibodies and any antigen binding fragment (i.e., "antigen-binding portion") or single chains thereof. Whole antibodies are glycoproteins comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system. The monospecific anti-BCMA antibody of the disclosure may comprise a heavy chain constant region having binding affinity to immune cells and the protein of the complement system, and the functional fragment thereof refers to the part of the constant region that retains the ability of binding immune cells and the complement system protein(s). The monospecific and bispecific anti-CD3 antibodies of the disclosure, including the anti-CD3/BCMA antibody, may comprise the heavy chain constant region with weak or no binding affinity to the immune cells and the complement system protein(s), and the functional fragment thereof refers to the part of the constant region that retains weak or no binding affinity to the immune cells and the complement system protein(s). The term "IgG like antibody" refers to a molecule prepared by modifying an IgG antibody, e.g., attaching a polypeptide or polypeptides to the N or C terminus of the heavy and/or light chain of an IgG antibody.

The term "half antibody" or "half-antibody" refers to one half of an antibody which comprises e.g., a heavy chain and a light chain.

The "knob variant" of a heavy chain constant region, or a heavy chain constant region with "knob mutation(s)" refers to a heavy chain constant region used in the knobs-into-holes technology whose CH3 domains are engineered to create a "knob". Similarly, the "hole variant" of a heavy chain constant region, or a heavy chain constant region with "hole mutation(s)" refers to a heavy chain constant region used in the knobs-into-holes technology whose CH3 domains are engineered to create a "hole".

The term "antigen-binding portion" of an antibody (or simply "antibody portion"), as used herein, refers to one or more fragments of an antibody that retain the ability to specifically bind to an antigen (e.g., a CD3 protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$ $V_H$, $C_L$ and $C_{H1}$ domains; (ii) a F(ab')₂ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; (vi) an isolated complementarity determining region (CDR); and (viii) a nanobody, a heavy chain variable region containing a single variable domain and two constant domains. Furthermore, although the two domains of the Fv fragment, $V_L$ and $V_H$, are coded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The term "FcR" or "Fc receptor" refers to a protein expressed on the surface of certain immune cells such as B lymphocytes, natural killer cells, and macrophages, which recognizes the Fc fragment of antibodies that are attached to cells or pathogens, and stimulates phagocytic or cytotoxic cells to destroy pathogens or target cells by e.g., antibody-mediated phagocytosis or antibody-dependent cell-mediated cytotoxicity. The FcR includes, FcαR, FcεR and FcγR, and the FcγR belongs to the immunoglobulin superfamily and is the most important Fc receptor for inducing phagocytosis of microbes, including FcγRI (CD64), FcγRIIA (CD32A), FcγRIIB (CD32B), and FcγRIIIA (CD16A).

A "bispecific" molecule, as used herein, specifically binds two target molecules, or two different epitopes in a same target molecule. The bispecific antibody of the disclosure specifically binding CD3 and a disease associated antigen (e.g., BCMA) is a kind of bispecific molecule. In contrast, a "monospecific" molecule specifically binds a certain target molecule, especially a certain epitope in the target molecule.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species have been grafted onto human framework sequences.

The term "humanized antibody", as used herein, refers to an antibody from non-human species whose protein sequences have been modified to increase similarity to antibody variants produced naturally in humans.

As used herein, an antibody that "specifically binds human CD3 or BCMA" is intended to refer to an antibody that binds to human CD3 protein (and possibly a CD3 protein from one or more non-human species) or human BCMA protein (and possibly a BCMA protein from one or more non-human species) but does not substantially bind to non-CD3 or non-BCMA proteins.

The term "EC50", also known as half maximal effective concentration, refers to the concentration of a molecule such as an antibody which induces a response halfway between the baseline and maximum after a specified exposure time.

The term "IC50", also known as half maximal inhibitory concentration, refers to the concentration of a molecule such as an antibody which inhibits a specific biological or biochemical function by 50% relative to the absence of the molecule.

The term "cross-link" or "cross-linking" refers to aggregation of antibodies through binding of the antibodies' Fc regions to FcRs on immune cells, or through binding of the antibodies to the disease associated antigens on target cells (by e.g., the moiety in a bispecific molecule targeting the disease associated antigens). In in vitro tests, antibody cross-linking occurs when antibodies bind to the secondary antibodies coupled to e.g., ELISA plates. The anti-CD3 antibody or antigen-binding portion thereof of the disclosure may activate T cells when antibody cross-linking occurs. In contrast, "free" antibodies or antigen-binding portions thereof of the disclosure, that do not interact among each other or to other molecules to form antibody dimers or polymers, are not capable of activating T cells.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

The term "therapeutically effective amount" means an amount of the antibody or the antigen binding portion of the present disclosure sufficient to prevent or ameliorate the symptoms associated with a disease or condition (such as a chronic inflammation) and/or lessen the severity of the disease or condition. A therapeutically effective amount is understood to be in context to the condition being treated, where the actual effective amount is readily discerned by those of skill in the art.

The percent "sequence identity" as used herein in the context of two or more nucleic acids or polypeptides, refers to two or more sequences or subsequences that are the same or have a specified percentage of nucleotides or amino acid residues that are the same, when compared and aligned (introducing gaps, if necessary) for maximum correspondence, considering or not considering conservative amino acid substitutions as part of the sequence identity. The percent identity can be measured using sequence comparison software or algorithms or by visual inspection. Various algorithms and software that can be used to obtain alignments of amino acid or nucleotide sequences are well-known in the art. These include, but are not limited to, BLAST, ALIGN, Megalign, BestFit, GCG Wisconsin Package, and variants thereof. In some embodiments, two nucleic acids or polypeptides of the disclosure are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection.

Various aspects of the disclosure are described in further detail in the following subsections.

Anti-BCMA Antibodies

The anti-BCMA antibody, or the antigen-binding portion thereof, of the disclosure specifically binds to human and monkey BCMA with comparable, if not higher, binding capability, as compared to the anti-BCMA part in EM801, and the binding is barely affected by the free BCMA molecules in the assays.

The heavy chain variable region CDRs and light chain variable region CDRs of the anti-BCMA antibody or antigen binding fragment thereof of the disclosure have been defined by the Kabat numbering system. However, as is well known in the art, CDRs can also be determined by other systems such as Chothia, and IMGT, AbM, or Contact numbering system/method, based on heavy chain/light chain variable region sequences.

Anti-CD3 Antibodies

The anti-CD3 antibody, or the antigen-binding portion thereof, of the disclosure specifically binds to human CD3, especially human CD3δ&ε.

The heavy chain variable region CDRs and light chain variable region CDRs of the anti-CD3 antibody or antigen binding fragment thereof of the disclosure have been defined by the Kabat numbering system. However, as is well known in the art, CDRs can also be determined by other systems such as Chothia, and IMGT, AbM, or Contact numbering system/method, based on heavy chain/light chain variable region sequences.

The "free" antibody or antigen-binding portion thereof of the disclosure can bind CD3 but does not activate T cells, while when antibody cross-linking occurs, antibody or antigen-binding portion thereof of the disclosure can bind CD3 and activate T cells. Thus, the antibody or antigen-binding portion thereof of the disclosure prepared with weak or no FcR binding affinity can be "free" or substantially "free" within bodies and can be used to treat inflammatory diseases and auto-immune diseases by inducing tolerance.

In another aspect, the anti-CD3 antibody or antigen-binding portion thereof of the disclosure may be prepared as part of a non-FcR binding bispecific antibody against CD3 and another target such as a tumor associated antigen or an antigen associated with e.g., an infectious disease or an inflammatory disease, upon cross-linking through binding to the non-CD3 targets, the bispecific antibody may activate T cells and kills target cells by e.g., releasing SMAPs. For example, the antibody or antigen-binding portion thereof may be prepared as part of a bispecific non-FcR binding antibody against CD3 and a tumor associated antigen, whose cross-linking occurs only when it binds to the tumor associated antigens at the lesion site. The bispecific antibody activates T cells to kill tumor cells when antibody cross-linking occurs. More importantly, compared to the prior art anti-CD3 antibodies, the bispecific antibody of the disclosure, upon cross-linking, causes less cytokine release, resulting in reduced toxicity.

Bispecific Antibodies

The present disclosure features a bispecific molecule which may comprise an antibody or an antigen binding fragment thereof of the disclosure linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities. The bispecific molecules may be in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called Bs(scFv)$_2$ construct. Intermediate-sized bispecific molecules include two different F(ab) fragments linked by a peptidyl linker, and one F(ab) fragment linked to a scFv via a peptidyl linker. Bispecific molecules of these and other formats can be prepared by genetic engineering, somatic hybridization, or chemical methods. See, e.g., Kufer et al, cited supra; Cao and Suresh, *Bioconjugate Chemistry*, 9 (6), 635-644 (1998); and van Spriel et al., *Immunology Today*, 21 (8), 391-397 (2000), and the references cited therein.

The bispecific molecule has, in addition to CD3 binding specificity, a second specificity to a disease associated antigen. In certain embodiments, the bispecific molecule may bind CD3 and a disease associated antigen. Preferably, the disease associated antigen is uniquely expressed on lesion cells, or alternatively expressed on lesion cells at high levels but at low levels on normal counterparts.

In certain embodiments, the disease associated antigen is a tumor associated antigen, such as CD20, CD19, CD22, CD4, CD24, CD38, CD123, CD228, CD138, BCMA, GPC3, CEA, CD276, gp100, 5T4, GD2, EGFR, MUC-1, PSMA, EpCAM, MCSP, SM5-1, MICA, MICB, ULBP and HER-2.

In certain embodiments, the disease associated antigen is an infectious disease associated antigen such as a marker protein on pathogens or infected cells. The infectious disease associated antigen may be CD4, BHsAg, LMP-1 and LMP2, wherein CD4 is the target for AIDS treatment.

In certain embodiments, the disease associated antigen is an inflammatory disease associated antigen such as a marker protein expressed on active immune cells that cause inflammations, including, but not limited to, IL17R and CD6.

The bispecific molecules of the disclosure direct the T cells to the target cells. Cross-linking occurs to bispecific molecules when the bispecific molecules bind to the disease associated antigens, which may activate T cells to kill target cells accordingly.

Anti-CD3/BCMA Molecules

In certain embodiments, the disease associated antigen is BCMA, which is a marker that is selectively and highly expressed on malignant plasma cells and a good target for diagnosis and/or treatment of multiple myeloma or other hematological malignancies.

The anti-CD3/BCMA bispecific molecule of the disclosure may contain one CD3 binding domain, and one to four BCMA binding domains. In one embodiment, the bispecific molecule may contain one CD3 binding domain and two BCMA binding domains. In one embodiment, the BCMA binding domain is an anti-BCMA antibody or an antigen-binding portion thereof, e.g., an Fv and/or a scFv, of the disclosure. In one embodiment, the CD3 binding domain may be an anti-CD3 antigen or an antigen-binding portion thereof, e.g., an Fv, of the disclosure. The two BCMA binding domains may bind to the same or different antigen epitopes, may contain the same or different antigen binding domain sequences, and/or may be present in the same or different antigen-binding domain formats.

In one embodiment, the bispecific molecule contains one anti-CD3 Fv, one anti-BCMA Fv, and one anti-BCMA scFv. In one embodiment, the anti-BCMA Fv and the anti-BCMA scFv comprise the same heavy chain variable region and light chain variable region.

The anti-CD3/BCMA bispecific molecule may be an IgG like antibody. In one embodiment, the bispecific antibody contains an anti-CD3 half antibody, an anti-BCMA half antibody, and an anti-BCMA scFv linked to the N terminus of the heavy or light chain variable region of the anti-CD3 half antibody.

In one embodiment, the bispecific antibody may contain:
i) a first polypeptide, containing an anti-BCMA heavy chain variable region and a heavy chain constant region,
ii) a second polypeptide, containing an anti-BCMA light chain variable region,
iii) a third polypeptide, containing an anti-BCMA heavy chain variable region, an anti-BCMA light chain variable region, an anti-CD3 heavy chain variable region, and a heavy chain constant region, and
iv) a fourth polypeptide, containing an anti-CD3 light chain variable region, wherein the anti-BCMA heavy chain variable region in the first polypeptide and the anti-BCMA light chain variable region in the second polypeptide may associate to form a BCMA binding domain, the anti-BCMA heavy chain variable region and the anti-BCMA light chain variable region in the third polypeptide may associate to form a BCMA binding domain, the anti-CD3 heavy chain variable region in the third polypeptide and the anti-CD3 light chain variable region in the fourth polypeptide may associate to form a CD3 binding domain, and the heavy chain constant region in the first polypeptide and the heavy chain constant region in the third polypeptide may be associated together via e.g., the knobs-into-holes approach, the covalent bond(s) and/or the disulfide bond(s).

In one embodiment, the first polypeptide comprises, from N terminus to C terminus, the anti-BCMA heavy chain variable region and the heavy chain constant region. The heavy chain constant region in the first polypeptide may be a hole variant. The third polypeptide comprises, from N terminus to C terminus, the anti-BCMA heavy chain variable region, the anti-BCMA light chain variable region, the anti-CD3 heavy chain variable region, and the heavy chain constant region; or alternatively the anti-BCMA light chain variable region, the anti-BCMA heavy chain variable region, the anti-CD3 heavy chain variable region, and the heavy chain constant region. The heavy chain constant region in the third polypeptide may be a knob variant.

In another embodiments, the bispecific antibody may contain:
i) a first polypeptide, containing an anti-BCMA heavy chain variable region and a heavy chain constant region,
ii) a second polypeptide, containing an anti-BCMA light chain variable region,
iii) a third polypeptide, containing an anti-CD3 heavy chain variable region, and a heavy chain constant region, and
iv) a fourth polypeptide, containing an anti-BCMA heavy chain variable region, an anti-BCMA light chain variable region, and an anti-CD3 light chain variable region, wherein the anti-BCMA heavy chain variable region in the first polypeptide and the anti-BCMA light chain variable region in the second polypeptide may associate to form a BCMA binding domain, the anti-CD3 heavy chain variable region in the third polypeptide and the anti-CD3 light chain variable region in the fourth polypeptide may associate to form a CD3 binding domain, the anti-BCMA heavy chain variable region and the anti-BCMA light chain variable region in the fourth polypeptide may associate to form a BCMA binding domain, and the heavy chain constant region in the first polypeptide and the heavy chain constant region in the third polypeptide may be associated together via e.g., the knobs-into-holes approach, the covalent bond(s) or the disulfide bond(s).

In one embodiment, the first polypeptide comprises, from N terminus to C terminus, the anti-BCMA heavy chain variable region and the heavy chain constant region. In one embodiment, the third polypeptide comprises, from N terminus to C terminus, the anti-CD3 heavy chain variable region, and the heavy chain constant region. In one embodiment, the fourth polypeptide comprises, from N terminus to C terminus, the anti-BCMA heavy chain variable region, the anti-BCMA light chain variable region and the anti-CD3 light chain variable region; the anti-BCMA light chain variable region, the anti-BCMA heavy chain variable region, and the anti-CD3 light chain variable region; the anti-CD3 light chain variable region, the anti-BCMA light chain variable region, and the anti-BCMA heavy chain variable region; or alternatively the anti-CD3 light chain variable region, the anti-BCMA heavy chain variable region, and the anti-BCMA light chain variable region.

In the bispecific antibody, the anti-BCMA heavy chain variable region may be linked via a linker to the anti-BCMA light chain variable region, to form a scFv. The anti-BCMA heavy chain variable region or the anti-BCMA light chain variable region may be linked via a linker to the anti-CD3 antibody or antigen-binding portion thereof.

The linker may be made up of amino acids linked together by peptide bonds, preferably from 5 to 30 amino acids linked by peptide bonds, wherein the amino acids are selected from the 20 naturally occurring amino acids. One or more of these amino acids may be glycosylated, as is understood by those of skill in the art. In one embodiment, the 5 to 30 amino acids may be selected from glycine, alanine, proline, asparagine, glutamine, serine and lysine. In one embodiment, a linker is made up of a majority of amino acids that are sterically unhindered, such as glycine and alanine. Exemplary linkers are polyglycines, particularly poly(Gly-Ala), and polyalanines. One exemplary linker used in the scFv comprise e.g., the amino acid sequence of SEQ ID NO: 19. One exemplary linker between the anti-BCMA antibody fragment and the anti-CD3 antibody fragment comprises e.g., the amino acid sequence of SEQ ID NO: 20.

The linker may also be a non-peptide linker. For example, alkyl linkers such as —NH—, —(CH$_2$)s-C(O)—, wherein s=2-20 can be used. These alkyl linkers may further be substituted by any non-sterically hindering group such as lower alkyl (e.g., C$_{1-4}$) lower acyl, halogen (e.g., Cl, Br), CN, NH$_2$, phenyl, etc.

Conservative Modification

In another embodiment, the antibody of the disclosure, including the anti-CD3 antibody, the anti-BCMA antibody, and the anti-CD3/BCMA bispecific antibody, may comprise a heavy and/or light chain variable region sequences or CDR1, CDR2 and CDR3 sequences with one or more conservative modifications. It is understood in the art that certain conservative sequence modification can be made which do not remove antigen binding. See, e.g., Brummell et al., (1993) *Biochem* 32:1180-8; de Wildt et al., (1997) *Prot. Eng.* 10:835-41; Komissarov et al., (1997) *J. Biol. Chem.* 272:26864-26870; Hall et al., (1992) *J. Immunol.* 149:1605-12; Kelley and O'Connell (1993) *Biochem.*

32:6862-35; Adib-Conquy et al., (1998) *Int. Immunol.* 10:341-6 and Beers et al., (2000) *Clin. Can. Res.* 6:2835-43.

As used herein, the term "conservative sequence modification" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the disclosure by standard techniques known in the art, such as site-directed mutagenesis and PCR-mediated mutagenesis. Conservative amino acid substitutions are ones in which the amino acid residue is replaced with an amino acid residue having a similar side chain Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the disclosure can be replaced with other amino acid residues from the same side chain family and the altered antibody can be tested for retained function (i.e., the functions set forth above) using the functional assays described herein.

Engineered Antibodies

The antibody of the disclosure, including the anti-CD3 antibody, the anti-BCAM antibody, and the anti-CD3/BCMA bispecific antibody, can be prepared using an antibody having one or more of the $V_H/V_L$ sequences of the antibody of the present disclosure, as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al., (1998) *Nature* 332:323-327; Jones et al., (1986) *Nature* 321:522-525; Queen et al., (1989) *Proc. Natl. Acad*. See also U.S.A. 86:10029-10033; U.S. Pat. Nos. 5,225,539; 5,530,101; 5,585,089; 5,693,762 and 6,180,370).

Accordingly, another embodiment of the disclosure pertains to an isolated monoclonal antibody, or antigen binding portion thereof, and/or an bispecific antibody, which may comprise a heavy chain variable region that may comprise CDR1, CDR2, and CDR3 sequences which may comprise the sequences of the present disclosure, as described above, and/or a light chain variable region which may comprise CDR1, CDR2, and CDR3 sequences which may comprise the sequences of the present disclosure, as described above. While these antibodies contain the $V_H$ and $V_L$ CDR sequences of the monoclonal antibody of the present disclosure, they can contain different framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al., (1991), cited supra; Tomlinson et al., (1992) *J. Mol. Biol.* 227:776-798; and Cox et al., (1994) *Eur. J. Immunol.* 24:827-836; the contents of each of which are expressly incorporated herein by reference. As another example, the germline DNA sequences for human heavy and light chain variable region genes can be found in the Genbank database.

Antibody protein sequences are compared against a compiled protein sequence database using one of the sequence similarity searching methods called the Gapped BLAST (Altschul et al., (1997), supra), which is well known to those skilled in the art.

Preferred framework sequences for use in the antibodies of the disclosure are those that are structurally similar to the framework sequences used by antibodies of the disclosure. The $V_H$ CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or five residues within a CDR region are altered.

Engineered antibodies of the disclosure include those in which modifications have been made to framework residues within $V_H$ and/or $V_L$, e.g. to improve the properties of the antibody. The framework modification may involve mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043. In addition, or as an alternative to modifications made within the framework or CDR regions, antibodies of the disclosure can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the disclosure can be chemically modified (e.g., one or more chemical moieties can be attached to the antibody) or be modified to alter its glycosylation, again to alter one or more functional properties of the antibody.

In one embodiment, the hinge region of $C_{H1}$ is modified in such that the number of cysteine residues in the hinge region is altered, e.g., increased or decreased. This approach is described further in U.S. Pat. No. 5,677,425. The number of cysteine residues in the hinge region of $C_{H1}$ is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the $C_{H2}$-$C_{H3}$ domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In still another embodiment, the glycosylation of an antibody is modified. For example, a glycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase or reduce the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, the cell lines Ms704, Ms705, and Ms709 lack the fucosyltransferase gene, FUT8 ($\alpha$(1, 6)-fucosyltransferase), such that antibodies expressed in the Ms704, Ms705, and Ms709 cell lines lack fucose on their carbohydrates. The Ms704, Ms705, and Ms709 FUT8-/- cell lines were created by the targeted disruption of the FUT8 gene in CHO/DG44 cells using two replacement vectors (see U.S. Patent Publication No. 20040110704 and Yamane-Ohnuki et al., (2004) Biotechnol Bioeng 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the $\alpha$-1, 6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662).

Another modification of the antibodies herein that is contemplated by this disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See, e.g., EP 0 154 316 and EP 0 401 384.

Generation of Antibodies

The monospecific anti-CD3 antibody and the monospecific anti-BCMA antibody of the disclosure can be produced using the well-known somatic cell hybridization (hybridoma) technique of Kohler and Milstein (1975) Nature 256: 495, viral or oncogenic transformation of B lymphocytes and phage display techniques. In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The bispecific antibody of the disclosure, including the one against CD3 and BCMA, may be produced by i) inserting the nucleotide sequences encoding polypeptides of the bispecific antibody into one or more expression vectors which are operatively linked to regulatory sequences that control transcription or translation; (ii) transducing or transfecting host cells with expression vectors; and (iii) expressing polypeptides to form the bispecific antibody of the disclosure.

The term "regulatory sequence" is intended to include promoters, enhancers and other expression control elements (e.g., polyadenylation signals) that control the transcription or translation of the antibody genes. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyomavirus enhancer. Alternatively, non-viral regulatory sequences can be used, such as the ubiquitin promoter or $\beta$-globin promoter. Still further, regulatory elements composed of sequences from different sources, such as the SR$\alpha$ promoter system, which contains sequences from the SV40 early promoter and the long terminal repeat of human T cell leukemia virus type 1 (Takebe et al., (1988) Mol. Cell. Biol. 8:466-472). The expression vector and expression control sequences are chosen to be compatible with the expression host cell used.

The expression vector can encode a signal peptide that facilitates secretion of the polypeptide from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the polypeptide genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the heavy and/or light chains of the anti-CD3 antibody, the anti-BCMA antibody, or the polypeptides of the bispecific antibody of the disclosure, the expression vector(s) is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

The expression vectors that can be used in the present application include but are not limited to plasmids, viral vectors, yeast artificial chromosomes (YACs), bacterial artificial chromosomes (BACs), transformation-competent artificial chromosomes (TACs), mammalian artificial chromosomes (MACs) and human artificial episomal chromosomes (HAECs).

Immunoconjugate

The disclosure also provides an immunoconjugate, such as an antibody-drug conjugate (ADC), that may comprise the anti-BCMA antibody, or antigen-binding portion thereof, of the disclosure, linked to a therapeutic agent. Suitable therapeutic agents include cytotoxins, alkylating agents, DNA minor groove binders, DNA intercalators, DNA cross-linkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker.

Chimeric Antigen Receptor

Also provided herein is a chimeric antigen receptor (CAR) containing an anti-BCMA scFv, wherein the anti-BCMA scFv may comprise the CDRs and heavy/light chain variable regions described herein.

The CAR may comprise (a) an extracellular antigen binding domain comprising an anti-BCMA scFv; (b) a transmembrane domain; and (c) an intracellular signaling domain.

Oncolytic Virus

Also provided herein is an oncolytic virus that preferentially infects and kills cancer cells. The anti-BCMA antibody or the anti-CD3/BCMA antibody of the present disclosure can be used in conjunction with oncolytic viruses. Alternatively, oncolytic viruses encoding the antibodies of the present disclosure can be introduced into human body.

Nucleic Acid Molecules

In another aspect, the disclosure provides a nucleic acid molecule that encodes the anti-CD3 antibody, the anti-BCMA antibody, or the antigen-binding portion thereof (the heavy and/or light chain variable regions, or CDRs), the bispecific antibody or the fragment thereof (e.g., the anti-BCMA heavy chain variable region-linker-anti-BCMA light chain variable region-linker-anti-CD3 heavy chain variable region, anti-BCMA light chain variable region-linker-anti-BCMA heavy chain variable region-linker-anti-CD3 heavy chain variable region), the immunoconjugate, or the CAR or TCR of the disclosure. The nucleic acid molecule can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the disclosure can be, e.g., DNA or RNA and may or may not contain intronic sequences. In a preferred embodiment, the nucleic acid is a cDNA molecule.

The nucleic acid molecule of the disclosure can be obtained using standard molecular biology techniques. For antibodies obtained from an immunoglobulin gene library (e.g., using phage display techniques), a nucleic acid encoding such antibodies can be recovered from the gene library.

Preferred nucleic acids molecules of the disclosure include those encoding the $V_H$ and/or $V_L$ sequences or the CDRs of the anti-CD3 or anti-BCMA monoclonal antibody. Once DNA fragments encoding $V_H$ and/or $V_L$ segments are obtained, these DNA fragments can be further manipulated by standard recombinant DNA techniques, for example to convert the variable region genes to full-length antibody chain genes, to Fab fragment genes or to scFv genes. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly4-Ser)$_3$, such that the $V_H$ and $V_L$ sequences can be expressed as a contiguous single-chain protein, with the $V_L$ and $V_H$ regions joined by the flexible linker.

For the bispecific antibody of the disclosure, nucleotide sequences encoding the anti-CD3 antibodies' CDRs, VH and VL, the anti-BCMA antibodies' VH and VL, and linkers are firstly synthesized, and then combined according to the structures of required bispecific antibodies.

Pharmaceutical Compositions

In another aspect, the present disclosure provides a pharmaceutical composition which may comprise the anti-BCMA antibody or antigen binding fragment thereof, the immunoconjugate, CAR or TCR-bearing cells comprising the anti-BCMA antibody or antigen binding fragment thereof, the anti-CD3 antibody or antigen binding fragment thereof, the bispecific anti-CD3/BCMA antibody or fragment thereof, the nucleic acid molecule, the expression vector, or the host cell, of the disclosure, formulated together with a pharmaceutically acceptable carrier. The pharmaceutical composition may optionally contain one or more additional pharmaceutically active ingredients, such as an anti-tumor antibody, an anti-infection antibody, an antibody for immune enhancement, or an antibody for an autoimmune disease, or alternatively a non-antibody anti-tumor agent, a non-antibody anti-infection agent, a non-antibody immune enhancement agent, or a non-antibody anti-inflammation agent. The pharmaceutical composition of the disclosure may be used in combination with an additional anti-tumor agent, an additional anti-infection agent, an additional immune enhancement agent, or an additional autoimmune disease-treating agent.

The pharmaceutical composition may comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients are taught in Gennaro, ed., Remington: *The Science and Practice of Pharmacy*, 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion. Alternatively, an antibody of the disclosure can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a micro-emulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about 99% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. Alternatively, antibody can be administered as a sustained release formulation, in which case less frequent administration is required.

The anti-CD3 antibody of the disclosure may be administered with reference to OKT3 dose approved by FDA, and should be finally determined by physicians depending on a subject's e.g., sex, age, medical history and etc. The dose of the bispecific antibodies of the disclosure against BCMA and CD3 may be determined by physicians depending on a subject's e.g., sex, age, medical history and etc.

A "therapeutically effective dosage" of the anti-CD3 antibody or antigen-binding portion thereof, the anti-BCMA antibody or antigen-binding portion thereof, or the anti-CD3/BCMA bispecific antibody of the disclosure, may result in a decrease in severity of disease symptoms, or an increase in frequency and duration of disease symptom-free periods. For example, for the treatment of tumor-bearing subjects, a "therapeutically effective dosage" preferably reduces tumor size by at least about 20%, more preferably by at least about 40%, even more preferably by at least about 60%, and still more preferably by at least about 80%, or even eliminate tumors, relative to untreated subjects.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Pharmaceutical compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the antibodies of the disclosure can be formulated to ensure proper distribution in vivo. For example, to ensure that the therapeutic antibody or antigen-binding portion thereof of the disclosure cross the blood-brain barrier, they can be formulated in liposomes, which may additionally comprise targeting moieties to enhance selective transport to specific cells or organs.

Uses and Methods

The pharmaceutical composition of the disclosure has multiple in vitro and in vivo applications. For example, the composition containing the monospecific anti-CD3 antibody may be used to treat or alleviate an inflammatory disease, an autoimmune disease, or implantation rejection. The anti-BCMA antibody of the disclosure may be used for e.g., in vitro BCMA detection, the diagnosis, disease progress monitoring, efficacy monitoring, and prognosis of multiple myeloma and other hematological malignancies.

In one aspect, the pharmaceutical composition of the disclosure containing the anti-CD3 antibody or antigen binding fragment thereof may be used for treatment and alleviation of an inflammatory disease, an autoimmune disease, or implantation rejection. The anti-CD3 antibody or antigen binding fragment thereof may comprise a heavy chain constant region with weak or no FcR binding affinity. In certain embodiments, the inflammatory disease is multiple sclerosis (MS), and inflammatory bowel disease (IBD) (such as Crohn's disease). In certain embodiments, the autoimmune disease is type I diabetes.

In another aspect, the pharmaceutical composition of the disclosure comprising the anti-BCMA antibody or antigen binding fragment thereof may be used to treat or alleviate multiple myeloma, and other hematological malignancies, including, but not limited to, plasmacytoma, plasma cell leukemia, macroglobulinemia, amyloidosis, Waldenstrom macroglobulinemia, extramedullary plasmacytoma, heavy chain disease, monoclonal gammopathy of undetermined significance, and smoldering myeloma.

In another aspect, the pharmaceutical composition comprising the bispecific molecule of the disclosure may be used to treat certain diseases by targeting CD3 and a disease associated antigen, wherein the bispecific molecule may contain no Fc region, or contain a Fc region with weak to no FcR binding affinity. Depending on the disease associated antigen, the pharmaceutical composition may treat various tumors, such as colon adenocarcinoma, breast cancer, renal cell cancer, melanoma, pancreatic cancer, non-small-cell lung cancer, glioblastoma, and gastric cancer, original or metastatic, infectious diseases such as AIDS, and various inflammatory diseases or autoimmune diseases.

In one embodiment, the pharmaceutical composition comprising the bispecific antibody of the disclosure against BCMA and CD3, and/or the nucleic acid molecule, the expression vector or the host cell encoding the same, may be used to treat or alleviate BCMA associated diseases, including, but not limited to multiple myeloma, plasmacytoma, plasma cell leukemia, macroglobulinemia, amyloidosis, Waldenstrom macroglobulinemia, extramedullary plasmacytoma, heavy chain disease, monoclonal gammopathy of undetermined significance, and smoldering myeloma.

The disclosure provides methods of combination therapy in which the pharmaceutical composition of the present disclosure is co-administered with one or more additional antibodies or non-antibody agents, for treatment or alleviation of certain diseases.

The combination of therapeutic agents discussed herein can be administered concurrently as a single composition in a pharmaceutically acceptable carrier, or concurrently as separate compositions with each agent in a pharmaceutically acceptable carrier. In another embodiment, the combination of therapeutic agents can be administered sequentially.

Furthermore, if more than one dose of the combination therapy is administered sequentially, the order of the sequential administration can be reversed or kept in the same order at each time point of administration, sequential administrations can be combined with concurrent administrations, or any combination thereof.

Although the present invention and its advantages have been described in detail, it should be understood that various changes, substitutions and alterations can be made herein without departing from the spirit and scope of the invention as defined in the appended claims.

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1. Construction of HEK293A Cell Lines Stably Expressing BCMA, BAFFR or TACI Cell lines stably expressing human BCMA, monkey BCMA, mouse BCMA, human BAFFR, and human TACI respectively were constructed using HEK293A cells. Briefly, sequences encoding human BCMA, monkey BCMA, mouse BCMA, human BAFFR, and human TACI (amino acid sequences set forth in SEQ ID NOs: 21-25) were synthesized, and then subcloned into pLV-EGFP(2A)-Puro vectors (Beijing Inovogen, China) between the restriction sites EcoRI and BamHI. Lentiviruses were generated in HEK293T cells (Cobioer, NJ, China) by cotransfection of the resultant expression vectors (i.e., pLV-EGFP(2A)-Puro-human BCMA, pLV-EGFP(2A)-Puro-monkey BCMA, pLV-EGFP(2A)-Puro-mouse BCMA, pLV-EGFP(2A)-Puro-BAFFR, and pLV-EGFP(2A)-Puro-TACI), psPAX and pMD2.G plasmids, according to the instruction in Lipofectamine 3000 kit (Thermo Fisher Scientific, USA). Three days post cotransfection, the lentiviruses were harvested from the HEK293T cell culture supernatants, and then used to infect HEK293A cells (Cobioer, NJ, China) to generate the required cell lines, which were referred to as HEK293A/human BCMA, HEK293A/monkey BCMA, HEK293A/mouse BCMA, HEK293A/human BAFFR, and HEK293A/human TACI. These HEK293A cells were cultured in DMEM (Cat #: SH30022.01, Gibco, USA) containing 10% FBS (Cat #: FND500, Excell, China) and 0.2 µg/ml puromycin (Cat #: A11138-03, Gibco) for 7 days. The expression of human and monkey BCMAs was confirmed by FACS using commercially available anti-BCMA antibody (PE anti-human BCMA Antibody, Cat #: 357503, Biolegend, US). Similarly, the expression of mouse BCMA, human BAFFR and human TACI was measured by FACS using the anti-mouse BCMA antibody (Cat #: 088472, Novus, US), PE-anti-human BAFFR antibody (Cat #: 316905, Biolegend, US), and PE-anti-human TACI antibody (Cat #: 133403, Biolegend, US).

Example 2. Generation of Anti-BCMA Monoclonal Antibody

Tubes were added and coated with 500 μL 10 μg/mL BCMA-his proteins (Cat #: BCA-H522y, ACRO) in sterile PBS overnight at 4° C., with the negative control tube coated with PBS. The tubes and an in house prepared phage display library were blocked with PBST containing 4% skimmed milk at 37° C. for 1 h, then the tubes were added with the phage display library having about $3 \times 10^{12}$ cfu phages and incubated at 37° C. for 1 h. The unbound phages were washed away by PBS(T), and then 0.1 M Glycine-HCl was used to elute phages bound to the antigens. Eluted phages were neutralized using 1.5 M Tris-HCl (pH8.8).

The above neutralized phages in 550 μl volume were used to infect 10 ml TG1 bacteria at the log phase, at 37° C. for 30 min. The bacteria cultures were determined for CFU, plated on 2YTAG plates, and cultured at 37° C. overnight. The bacterial colonies were removed from the plates, and re-suspended in 50 mL 2YTGA culture medium. After cultured to the log phase, the bacteria were added with 2 mL helper phage M13 (pfu=$1 \times 10^{13}$), and cultured with shaking at 30° C. overnight. The supernatants were harvested and precipitated with PEG, the resultant phage library was subjected to the next round of screening. Three rounds of such biopanning were carried out in total, after which single bacterial colonies were cultured in 1 mL 2YTAG medium containing 100 μg/ml ampicillin and 2% glucose overnight at 37° C. with 220 rpm shaking. The bacterial cultures were moved to the deep-well plates and cultured until the log phase. The plates were added with about $10^{10}$ M13 per well. After 30 min at 37° C., the plates were centrifuged at 4° C. at 4000 rpm for 15 min. The supernatants were removed, and the bacteria were re-suspended in 2YTAG medium containing 100 μg/ml ampicillin and 70 μg/ml kanamycin, and cultured at 28° C. with shaking at 220 rpm. The culture supernatants were subjected to ELISA to pick out positive clones. One antibody was obtained, termed as A6-3, and sequenced, with its VH-CDR1, VH-CDR2, VH-CDR3, VL-CDR1, VL-CDR2, VL-CDR3, VH and VL's amino acid sequences set forth in SEQ ID NOs: 1-7 and 8, respectively.

The antibody A6-3 was subjected to phage display and precipitation, such that highly purified scFvs displayed on phages were obtained. The scFvs were tested in ELISA for their binding capability to the BCMA protein. In particular, serially diluted phage-displayed antibodies, 3-fold dilution starting at 0.1 mg/ml, were incubated with the BCMA protein (Cat #: BCA-H522y, ACRO), and the HRP-mouse anti-M13 antibody (Cat #: 11973-MMO5T-H, Sino Biological) was used to test the binding of the phage-displayed antibodies to the BCMA protein. The results were shown in FIG. 1.

Figure 1:
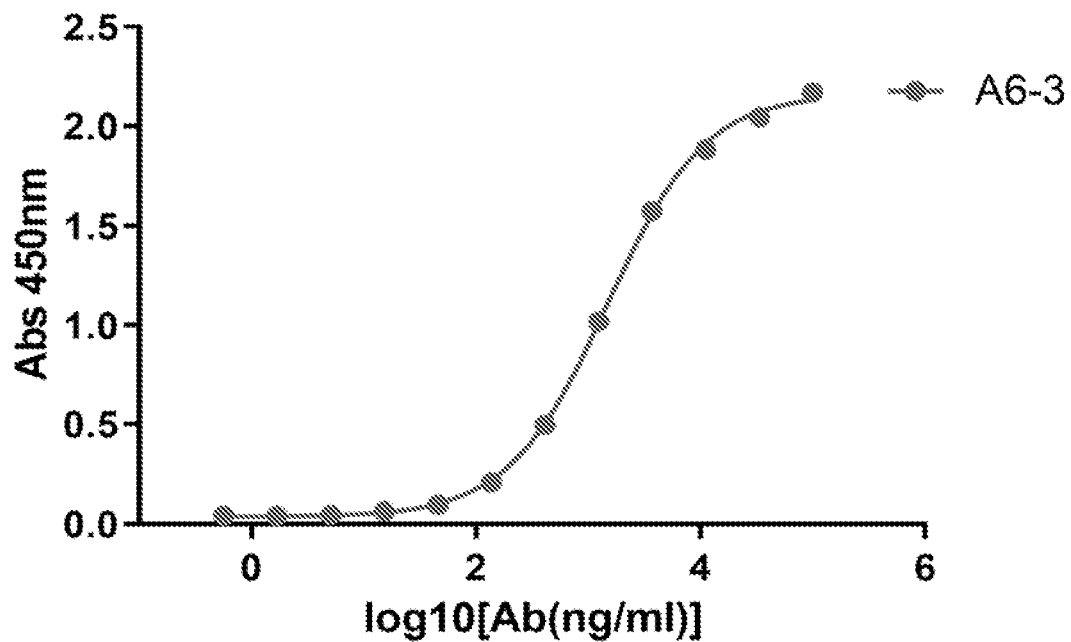
FIG. 1 shows the binding capability of the anti-BCMA antibody A6-3 displayed on phages to the BCMA protein.

It can be seen from FIG. 1 that the phage-displayed antibody A6-3 specifically bound to the BCMA protein in a concentration dependent manner.

Example 3. Expression and Purification of Full-Length Anti-BCMA Antibody

The A6-3 scFv antibody was expressed in HEK293F cells (Cobioer, China) as a full-length antibody for further characterization. Briefly, the expression vectors were constructed by cloning the nucleotides encoding the heavy/light chain variable region plus human IgG1/kappa constant region (amino acid sequences set forth in SEQ ID NOs.: 17 (X1=L, X2=L, X3=N, X4=T, X5=L, X6=Y) and 18, respectively) into pCDNA3.1 (Invitrogen, Carlsbad, US) between EcoRI and BamHI, wherein the C terminus of the heavy chain variable region was linked to the N terminus of the heavy chain constant region, and the C terminus of the light chain variable region was linked to the N terminus of the light chain constant region.

The pCDNA3.1-A6-3 plasmids were extracted using Tiangen® EndoFree Maxi Plasmid Kit (Cat #: DP117, Tiangen), and suspended in 5 mL FreeStyle F17 cell culture medium, which were then added with PEI at a volume 3 times that of the plasmids. Briefly, the PEI was slowly added to and mixed with the plasmids, the resultant mixtures were kept still at room temperature for 15 min and added to 100 ml 293F cells (cell density at $1 \times 10^6$/mL). The cells were cultured at 37° C. for 6-7 days in a shaker, and centrifuged at 300 rpm for 15 min to collect the supernatants. The supernatants were flowed through Protein-A affinity columns (Cat #: 17040501, GE, USA), and the columns were washed with PBS for three to four times and eluted with 0.2 M Glycine-HCl (pH 2.4). The elution was neutralized to pH 7.4 using 1.5 M Tris-HCl (pH 9.1), and then subjected to buffer exchange and antibody concentration in 30K ultrafilter tubes. The obtained antibodies were kept in PBS (pH 7.4) and the concentration was determined using the NanoDrop spectrophotometer.

Example 4. Binding Activity of Anti-BCMA Antibody to BCMA

Briefly, an ELISA plate was coated with 100 μl 1 μg/ml BCMA protein (Cat #: BCA-H522y, ACRO) in PBS overnight at 4° C. Then, the plate was blocked with 250 μl PBST with 4% skimmed milk at room temperature for 1 h. The plate was washed with PBST for three times, added with 100 μl serially diluted A6-3 antibodies in PBST (3-fold dilution starting at 10 μg/ml), and incubated at 37° C. for 1 h. The negative control well was added with PBST instead of the antibody. The plate was washed with PBST for three times, added with 100 μl HRP conjugated goat anti-human IgG (1:7000, Cat #: 31413, thermofisher), and incubated at room temperature for 1 h. The plate was washed again with PBST for four times, added with 100 μl freshly prepared TMB (Cat #: 555214, BD, USA), and left still for color development, which was terminated with 50 μl 10% $H_2SO_4$. The absorbance was read at 450 nm, and the data was processed and analyzed using GraphPad. The results can be found in FIG. 2.

Figure 2:
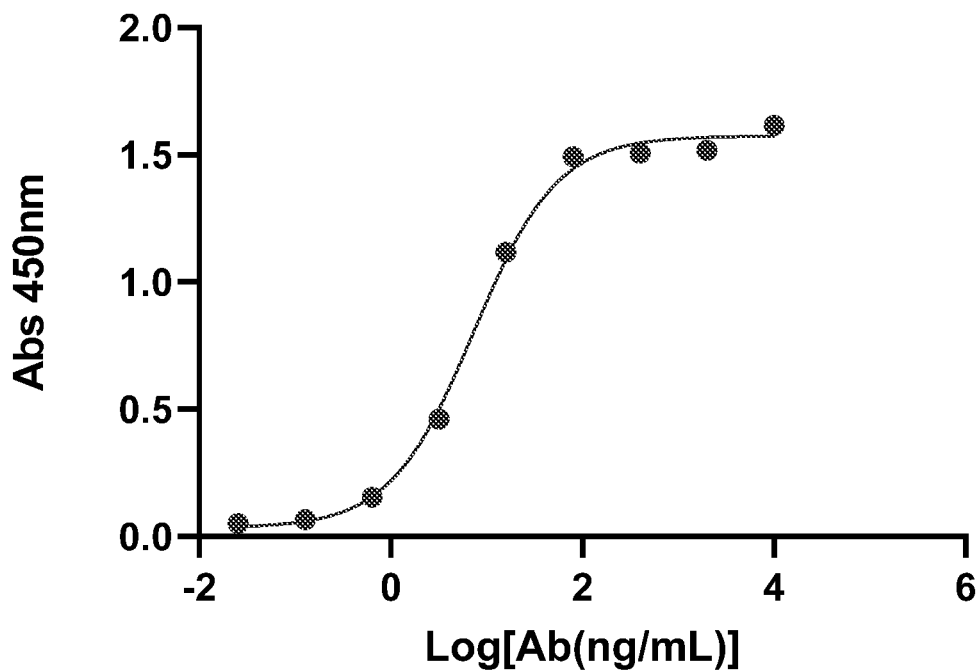
FIG. 2 shows the binding capability of the anti-BCMA antibody to the BCMA protein.

As shown in FIG. 2, the antibody A6-3 had high binding activity to the BCMA protein in a concentration dependent manner. The binding $EC_{50}$ was determined to be 7.332 ng/ml.

Example 5. Binding Affinity Determination of Anti-BCMA Antibody

The binding affinity of A6-3 to the BCMA protein was measured by BIAcore™ 8K (GE Life Sciences, USA).

Briefly, the mouse anti-human Fc antibody (Cat #: BR100839, cytiva) was coupled to CM5 biosensor chip. The antibody A6-3 diluted with the HBS-EP buffer (Cat #: BR-1006-69, GE Life Sciences) at the concentration of 1 μg/ml was flowed through the chip, where about 100 RU (response unit) of the antibody was captured by the mouse anti-human Fc antibody. Serially diluted BCMA proteins (Cat #: BCA-H522y, ACRO) in the HBS-EP buffer at the concentration of 0.5, 0.25, 0.125, 0.0625, 0.03125, 0.015625, 0.0078125 and 0.003900625 μg/ml were respectively flowed through the chip. Chip regeneration was performed with 3 M $MgCl_2$. The assay was run with the Wizard template, the $K_D$ value was determined and shown in Table 1, and the binding curve was shown in FIG. 3.

TABLE 1

Binding affinity of anti-BCMA antibody to human BCMA

|  | Ka | Kd | $K_D$ (M) |
|---|---|---|---|
| A6-3 | 1.37E+06 | 1.82E−04 | 1.32E−10 |

Figure 3:
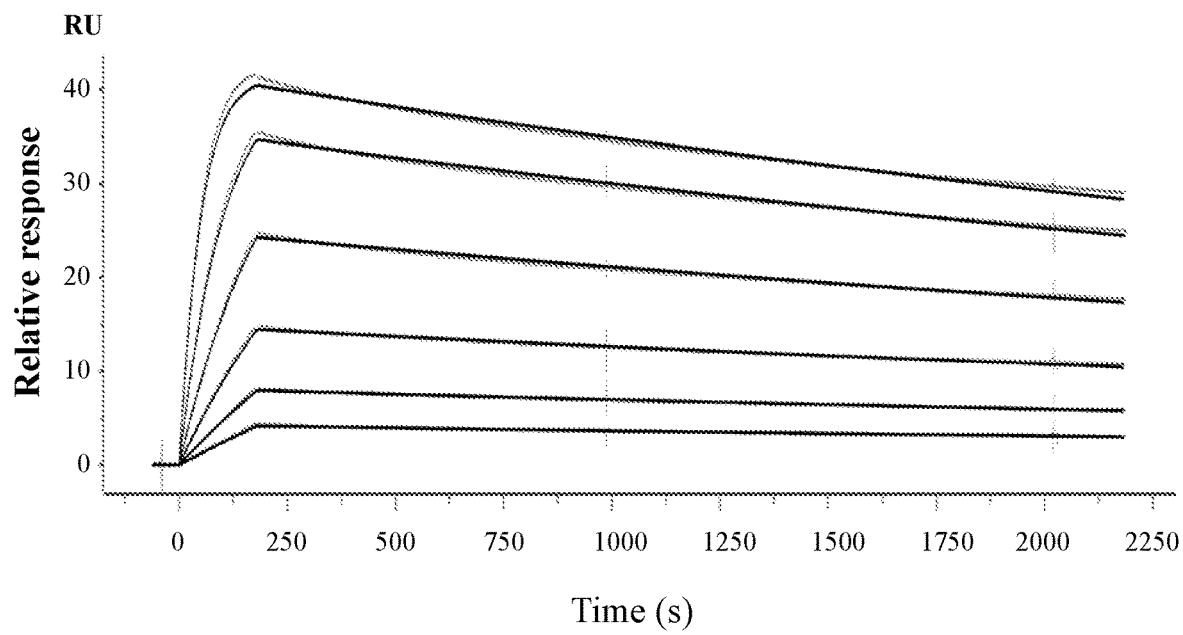
FIG. 3 shows the binding affinity of the anti-BCMA antibody to the BCMA protein.

It can be seen from Table 1 and FIG. 3 that the antibody A6-3 bound the BCMA protein with a high binding affinity.

Example 6. Binding Activity and Specificity of Anti-BCMA Antibody to Cell Surface BCMAs The anti-BCMA antibody's binding capability to cell surface BCMAs was tested by FACS. Briefly, HEK293A/human BCMA cells, HEK293A/monkey BCMA cells and HEK293A/mouse BCMA cells, as generated in Example 1, were collected, digested with trypsin, and subjected to centrifugation at 300 g for 5 min. The cells were suspended in PBS, and subjected to centrifugation again. The cells were re-suspended in PBS with 2% FBS at the cell density at $4\times10^6$/ml, and 50 μl cells were seeded onto a U-bottom plate. The plate was added with 50 μl serially diluted A6-3 antibodies (5-fold dilution, starting at 20 μg/ml, for the HEK293A/human BCMA cells and HEK293A/mouse BCMA cells, or starting at 40 μg/ml for the HEK293A/monkey BCMA cells), and incubated at room temperature for 1 h. The plate was washed with 2% FBS-PBS for three times, added with 50 μl PE-labeled goat-anti-human IgG (H+L) (1:500), and incubated at room temperature for 45 min. The plate was washed with 2% FBS-PBS again for three times, and added with 150 μl 2% FBS-PBS to suspend the cells. The plate was measured for cell fluorescence using a cytometry, and the data was processed with FlowJo and analyzed with GraphPad.

The antibody A6-3 was also tested for its binding activity to BAFFR and TACI, following the protocol above, except that the antibody was tested with two concentrations only, i.e., 100 μg/ml and 10 μg/ml.

Figure 4:
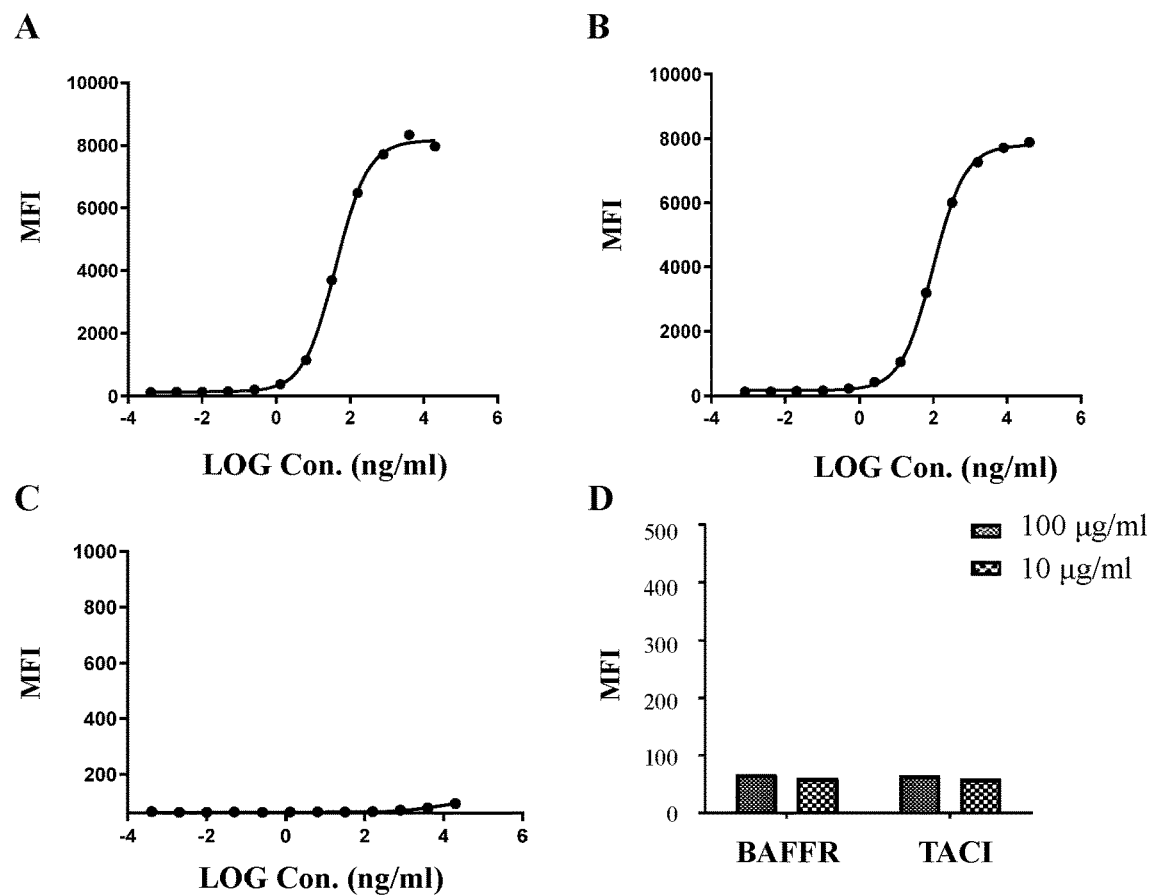
FIG. 4 shows the binding activity of the anti-BCMA antibody to HEK293A/human BCMA cells (A), HEK293A/ monkey BCMA cells (B), HEK293A/mouse BCMA cells (C), HEK293A/human BAFFR cells and HEK293A/human TACI cells (D).

According to FIG. 4 (A, B, C), the antibody A6-3 showed high binding capability to the HEK293A/human BCMA cells and HEK293A/monkey BCMA cells in a concentration dependent manner, but did not bind the HEK293A/mouse BCMA cells. The $EC_{50}$ values for binding HEK293A/human BCMA cells and HEK293A/monkey BCMA cells were respectively 41.52 ng/ml and 98.57 ng/ml.

Further, it can be seen from FIG. 4 (D) that A6-3 did not bind BAFFR or TACI, suggesting its binding specificity to BCMA.

Example 7. Effect of Free BCMA Molecules on Antibody-BCMA Binding

The effect of the free BCMA molecules (sBCMAs) on A6-3-BCMA$^+$ cell binding was determined using the HEK293A/human BCMA cells as generated in Example 1.

Briefly, $10^5$ HEK293A/human BCMA cells in 100 μl culture medium were seeded on a 96-well plate, and the plate was further added with 50 μl serially diluted antibody or PBS followed by the human BCMA-his proteins (Cat #: 10620-H08H, Sino Biological) at the final concentration of 1 μg/ml. After 1-h incubation at 4° C., the plate was washed with PBS for three times, added with APC-goat-anti-mouse IgG (1:500 dilution, Cat #: 405308, BioLegend, US), inducted at 4° C. for 1 h, washed with PBS for three times, and measured for cell fluorescence using a FACS analyzer (BD).

The results were shown in FIG. 5, which showed that the free BCMA molecules slightly reduced A6-3's binding activity to the HEK293A/human BCMA cells. In other words, the free BCMA molecules did not significantly affect the antibody's binding capability to BCMA$^+$ cells.

Example 8. Generation of Anti-CD3 Monoclonal Antibodies

CD3D and CD3E refer to the δ and ε chain of the CD3 molecule, respectively.

Following the protocol of Example 2, monoclonal anti-CD3D&E antibodies were screened out, 4 of which were referred to as D1E9, 7-1A12, D8E5 and D12A4 with the SEQ ID NOs. of the variable region sequences set forth in Table 2.

TABLE 2

| SEQ ID NO. of variable region sequences of anti-CD3D&E antibodies | | |
|---|---|---|
| | Heavy chain variable region | Light chain variable region |
| D1E9 | VH-CDR1 (SEQ ID NO: 9) | VL-CDR1 (SEQ ID NO: 12) |
| | VH-CDR2 (SEQ ID NO: 10) | VL-CDR2 (SEQ ID NO: 13) |
| | VH-CDR3 (SEQ ID NO: 11) | VL-CDR3 (SEQ ID NO: 14) |
| | VH (SEQ ID NO: 15) | VL (SEQ ID NO: 16) |
| 7-1A12 | VH-CDR1 (SEQ ID NO: 26) | VL-CDR1 (SEQ ID NO: 29, X1 = Q, X2 = R, |
| | VH-CDR2 (SEQ ID NO: 27, X1 = T, X2 = T, | X3 = V) |
| | J = I) | VL-CDR2 (SEQ ID NO: 30, X1 = R, X2 = Q) |
| | VH-CDR3 (SEQ ID NO: 28, X1 = N, X2 = F) | VL-CDR3 (SEQ ID NO: 31, X1 = S, X2 = I, |
| | VH (SEQ ID NO: 32, X1 = S, X2 = D, X3 = T, | X3 = Q) |
| | X4 = T, X5 = T, J = I, X6 = N, X7 = F) | VL (SEQ ID NO: 33, X1 = Q, X2 = R, X3 = V, |
| | | X4 = R, X5 = Q, X6 = S, X7 = I, X8 = Q) |

TABLE 2-continued

SEQ ID NO. of variable region sequences of anti-CD3D&E antibodies

| | Heavy chain variable region | Light chain variable region |
|---|---|---|
| D8E5 | VH-CDR1 (SEQ ID NO: 41)<br>VH-CDR2 (SEQ ID NO: 27, X1 = S, X2 = S, J = L)<br>VH-CDR3 (SEQ ID NO: 28, X1 = R, X2 = Y)<br>VH (SEQ ID NO: 32, X1 = D, X2 = S, X3 = S, X4 = S, X5 = S, J = L, X6 = R, X7 = Y) | VL-CDR1 (SEQ ID NO: 29, X1 = R, X2 = L, X3 = V)<br>VL-CDR2 (SEQ ID NO: 30, X1 = K, X2 = Y)<br>VL-CDR3 (SEQ ID NO: 31, X1 = Q, X2 = I, X3 = T)<br>VL (SEQ ID NO: 33, X1 = R, X2 = L, X3 = V, X4 = K, X5 = Y, X6 = Q, X7 = I, X8 = T) |
| D12A4 | VH-CDR1 (SEQ ID NO: 42)<br>VH-CDR2 (SEQ ID NO: 27, X1 = H, X2 = H, J = I)<br>VH-CDR3 (SEQ ID NO: 28, X1 = N, X2 = Y)<br>VH (SEQ ID NO: 32, X1 = G, X2 = D, X3 = A, X4 = H, X5 = H, J = I, X6 = N, X7 = Y) | VL-CDR1 (SEQ ID NO: 29, X1 = R, X2 = R, X3 = L)<br>VL-CDR2 (SEQ ID NO: 30, X1 = K, X2 = P)<br>VL-CDR3 (SEQ ID NO: 31, X1 = H, X2 = T, X3 = R)<br>VL (SEQ ID NO: 33, X1 = R, X2 = R, X3 = L, X4 = K, X5 = P, X6 = H, X7 = T, X8 = R) |

The four antibodies were subjected to phage display and precipitation, such that highly purified scFvs displayed on phages were obtained, which were tested for their binding capability to CD3D&E by ELISA. Briefly, the antibodies were 3-fold diluted, starting at 0.1 mg/ml or 1 mg/ml, and then added with the CD3D&E protein (Cat #: CT038-H2508H, Sino Biological), followed by the HRP-mouse anti-M13 antibody (Cat #: 11973-MMO5T-H, Sino Biological). The test results were shown in FIG. 6.

According to FIG. 6, the four antibodies specifically bound CD3D&E in a concentration dependent manner.

Following the protocol in Example 3, the scFvs, i.e., D1E9, 7-1A12, D8E5 and D12A4, were expressed as full-length antibodies in HEK293 cells (Cobioer, CN), wherein the human IgG1 and κ constant region sequences were set forth in SEQ ID NO: 17 (X1=A, X2=A, X3=A, X4=T, X5=L, X6=Y) and 18, respectively. The full-length antibodies were purified using Protein-A columns.

Example 9. Binding Capability of Anti-CD3 Antibodies to CD3D&E

Following the protocol in Example 4, the full-length antibodies D1E9, 7-1A12, D8E5 and D12A4 were tested for their binding capability to CD3D&E (Cat #: CT038-H2508H, Sino Biological). The results were shown in FIG. 7.

TABLE 3

Binding capability of anti-CD3 antibodies to CD3D&E

| | D1E9 | 7-1A12 | D8E5 | D12A4 |
|---|---|---|---|---|
| $EC_{50}$ (ng/ml) | 87.92 | 4.02 | 8.16 | 22.58 |

According to FIG. 7, the four antibodies showed high binding capability to CD3D&E in a concentration dependent manner. The EC50s as determined by GraphPad were set forth in Table 3.

Following the protocol in Example 4 with minor modifications as described below, the antibodies were tested for their binding capability to CD3D (Cat #: 10981-H08H, Sino Biological) and CD3E (Cat #: 10977-H085, Sino Biological), respectively, with the antibody concentration set at 10 µg/ml. The antibody ACD3 was used as a positive control, whose heavy and light chain variable region sequences were set forth in SEQ ID NOs: 7 and 8 in WO2022056455A1, and the human IgG1 heavy chain constant region and the κ light chain constant region with the amino acid sequences of SEQ ID NOs: 17 (X1=A, X2=A, X3=A, X4=T, X5=L, X6=Y) and 18 were used as the constant regions. The results were shown in FIG. 8.

It can be seen that none of the four antibodies bound CD3E (FIG. 8 (A)) or CD3D (FIG. 8 (B)).

Example 10. Binding Affinity Determination of Anti-CD3 Antibodies

The binding affinity of D1E9, 7-1A12, D8E5 and D12A4 to CD3D&E, CD3E and CD3D was measured by BIAcore™ 8K.

Briefly, the mouse anti-human Fc antibodies were coupled to a CM5 biosensor chip. The anti-CD3 antibodies of the disclosure in the HBS-EP buffer (Cat #: BR-1006-69, GE Life Sciences) at the concentration of 1 µg/ml was flowed through the chip, where about 100 RU of the antibodies were captured by the mouse anti-human Fc antibodies. Serially diluted CD3D&E molecules (Cat #: CT038-H2508H, Sino Biological) in the HBS-EP buffer (Cat #: BR-1006-69, GE Life Sciences) (2-fold dilution starting at 20 µg/ml) were respectively flowed through the chip. Chip regeneration was performed with 3 M $MgCl_2$. The assay was run with the Wizard template, the $K_D$ values were determined and shown in Table 4.

It can be seen from Table 4 that the anti-CD3 antibodies of the disclosure bound the CD3D&E complex with the binding affinity in the range of 357-6.54 nM.

TABLE 4

Binding affinity of D1E9, 7-1A12, D8E5 and D12A4 to human CD3D&E complex

| | Ka | Kd | $K_D$ (M) |
|---|---|---|---|
| D1E9 | 4.98E+04 | 5.97E−03 | 1.20E−07 |
| 7-1A12 | 7.18E+04 | 4.7E−04 | 6.54E−09 |
| D8E5 | 5.17E+04 | 1.55E−03 | 3.00E−08 |
| D12A4 | 3.49E+04 | 1.25E−02 | 3.57E−07 |

For the test regarding binding affinity to CD3D, the mouse anti-his antibodies were coupled to a CM5 biosensor chip. The CD3D-his proteins (Cat #: 10981-H08H, Sino Biological) diluted with the HBS-EP buffer (Cat #: BR-1006-69, GE Life Sciences) at the concentration of 2 µg/ml was flowed through the chip, where about 50 RU of the proteins were captured by the mouse anti-his antibodies. The anti-CD3 antibodies of the disclosure diluted with the HBS-EP buffer (Cat #: BR-1006-69, GE Life Sciences) at 120 µg/ml were respectively flowed through the chip. Chip regeneration was performed with 3 M MgCl$_2$. The assay was run with the Wizard template, and the results indicated that none of the antibodies bound the CD3D protein.

For the test regarding binding affinity to CD3E (Cat #: 10977-H08S, Sino Biological), the CD3E molecules were coupled to a CM5 biosensor chip, where about 200 RU of the molecules bound to the chip. The anti-CD3 antibodies of the disclosure diluted with the HBS-EP buffer (Cat #: BR-1006-69, GE Life Sciences) at 120 µg/ml were respectively flowed through the chip. Chip regeneration was performed with pH1.5 Gly-HCl. The assay was run with the Wizard template, and the results indicated that none of the antibodies bound the CD3E protein.

The results above suggested that the anti-CD3 antibodies of the disclosure recognized the CD3D&E complex.

Example 11. Binding Capability of Anti-CD3 Antibodies to Jurkat Cells

Jurkat cells were collected, centrifuged at 300 g for 5 min, and suspended in PBS. After another centrifugation, the cells were suspended in 2% FBS-PBS at the cell density of 3×10$^6$/ml, and 50 of the cells were plated onto a U-bottom plate. The plate was added with 50 µl serially diluted anti-CD3 antibodies of the disclosure in 2% FBS-PBS (4-fold dilution, starting at 20 µg/ml), and incubated at room temperature for 1 h. The plate was washed with 2% FBS-PBS for three times, added with 50 µl PE-labeled goat-anti-human IgG (H+L) (1:500), and incubated at room temperature for 45 min. The plate was washed with 2% FBS-PBS again for three times, and added with 150 µl 2% FBS-PBS to suspend the cells. The plate was measured for cell fluorescence using a cytometry, and the data was processed with FlowJo and analyzed with GraphPad. The results were shown in FIG. 9.

It can be seen from FIG. 9 that these antibodies bound to Jurkat cells with high capability in a concentration dependent manner. The binding EC$_{50}$ values were set forth in Table 5.

TABLE 5

Binding activity of anti-CD3 antibodies to Jurkat cells

|  | D1E9 | 7-1A12 | D8E5 | D12A4 |
| --- | --- | --- | --- | --- |
| EC$_{50}$ (ng/ml) | 83.67 | 119.1 | 41.08 | 110.0 |

Example 12. Anti-CD3 Antibodies' Regulatory Effects on T Cell Activity

The anti-CD3 antibodies of the disclosure were tested for their effects on CD3/TCR signaling when antibody cross-linking occurred, using primary human T cells.

Briefly, a 96-well cell culture plate was coated with 100 µl 5 µg/ml F(ab')$^2$-Goat anti-Human IgG Fc gamma Secondary Antibody (Cat #: 31163, Invitrogen, USA) at 4 C overnight. The plate was washed with PBS twice, added and incubated with 100 µl anti-CD3 antibodies of the disclosure at different concentrations at 37° C. for 2 h. Meanwhile, PBMCs from a healthy human donor's blood sample were collected by density gradient centrifugation, and CD4$^+$ T cells were isolated from the PBMCs using Invitrogen Dyna-beads Untouched Human CD4$^+$ T cell isolation kit (Cat #: 11346D, Thermal Fisher Scientific, USA) according to the manufacturer's instruction. The CD4$^+$ T cells were suspended at a cell density of 2.5×10$^5$/ml, and 200 µl of the T cell suspensions were added to the anti-CD3 coated plate, and incubated at 37° C. with 5% CO$_2$ for 24 h. After the incubation, 50 µl of the cell culture supernatant from each well was subjected to IFN-γ level measurement, using the kit (Cat #: SIF50, R&D, US) following the manual. The cells were incubated for another 48 h, collected, washed with PBS for three times, added with 2 µl PE-mouse anti-human CD69 antibody (Cat #: 555531, BD, US), incubated at room temperature for 30 min, centrifuged, and washed with PBS for three times. The ratio of CD69$^+$CD4$^+$ T cells to CD4$^+$ T cells was determined by FACS, which may be used to evaluate the effect of the cross-linked antibodies on T cell activation.

According to FIG. 10, all the anti-CD3 antibodies of the disclosure significantly activated T cells with increased IFN-γ secretion (FIG. 10 (A, B)), and increased CD69 expression on T cells in a concentration dependent manner (FIG. 10 (C, D)).

Example 13. Construction and Expression of Anti-CD3/BCMA Bispecific Antibodies Bispecific antibodies were constructed in an asymmetrical format (anti-BCMA: anti-CD3=2:1), with the structure shown in FIG. 11. Five half-antibodies, i.e., MBS305-H1-knob, MBS305-H2-knob, MBS305-M-knob, MBS305-L-knob, and MBS305-hole, were constructed.

In particular, the half-antibody MBS305-H2-knob contained a long chain (anti-BCMA scFv-linker-D1E9's heavy chain variable region-heavy chain constant region) with amino acid sequence of SEQ ID NO: 34, and a short chain (D1E9's light chain variable region-light chain constant region) with the amino acid sequence of SEQ ID NO: 35. The half-antibody MBS305-H1-knob was similar to MBS305-H2-knob in structure but used 7-1-A12's variable regions, and its long chain and short chain contained the amino acid sequences of SEQ ID NOs: 36 (X1=S, X2=D, X3=T, X4=T, X5=T, J=I, X6=N, X7=F) and 37 (X1=Q, X2=R, X3=V, X4=R, X5=Q, X6=S, X7=I, X8=Q), respectively. The half-antibody MBS305-M-knob was similar to MBS305-H2-knob in structure but used D8E5's variable regions, and its long chain and short chain contained the amino acid sequences of SEQ ID NOs: 36 (X1=D, X2=S, X3=S, X4=S, X5=S, J=L, X6=R, X7=Y) and 37 (X1=R, X2=L, X3=V, X4=K, X5=Y, X6=Q, X7=I, X8=T), respectively. The half-antibody MBS305-L-knob was similar to MBS305-H2-knob in structure but used D12A4's variable regions, and its long chain and short chain contained the amino acid sequences of SEQ ID NOs: 36 (X1=G, X2=D, X3=A, X4=H, X5=H, J=I, X6=N, X7=Y) and 37 (X1=R, X2=R, X3=L, X4=K, X5=P, X6=H, X7=T, X8=R), respectively. The half-antibody MBS305-hole contained a long chain (anti-BCMA heavy chain variable region-heavy chain constant region) with amino acid sequence of SEQ ID NO: 38, and a short chain (anti-BCMA light chain variable region-light chain constant region) with amino acid sequence of SEQ ID NO: 39. The anti-BCMA scFv was modified in the framework regions of the light chain variable region to enhance the conformational stability. In particular, the anti-BCMA scFv contains VL with amino acid sequence of SEQ ID NO: 40.

DNA fragments encoding the anti-BCMA scFv-linker-anti-CD3 heavy chain variable region chain in the half-antibodies with the knob, and those encoding the anti-BCMA heavy chain variable region in the half-antibody MBS305-hole, were synthesized, digested with EcoRI and NheI, and then ligated into the vectors containing the heavy chain constant regions, respectively. DNA sequences encoding the anti-CD3 light chain variable region in the half-antibodies with the knob, and those encoding the anti-BCMA light chain variable region were synthesized, digested with ClaI and BsiWI, and then ligated into the vectors containing the light chain constant regions, respectively. The light chain coding sequences were digested with ClaI and HindIII, the heavy chain coding sequences were digested with EcoRI and XhoI, the pCMV-cofragment plasmids were digested with HindIII and EcoRI, and the GS-vectors were digested with ClaI and XhoI. The 5 DNA fragments were purified, ligated, and transformed into bacteria. Single bacterial colonies were picked up and sequenced, and expression vectors containing the correct sequences to encode the half-antibody fragments were obtained. HEK-293F cells (Cobioer, China) were transfected with the expression vectors obtained above using PEI, following the protocol of Example 3. The transfected HEK-293F cells were cultured in an incubator in 5% $CO_2$ at 37° C. with shaking at 120 RPM. After 10-12 days, cell culture supernatants were harvested, centrifuged at 3500 rpm for 5 min and then subjected to filtration using 0.22 μm film filters to remove cell debris.

The obtained half antibodies were purified using pre-equilibrated Protein-A affinity columns (Cat #: 17040501, GE, USA), eluted with the elution buffer (20 mM citric acid, pH 3.0-3.5), and kept in PBS buffer (pH 7.0). The antibody concentrations were determined using a NanoDrop analyzer.

Example 14. Assembly of Anti-CD3/BCMA Bispecific Antibodies

The purified half antibodies were assembled in vitro. Briefly, the half antibodies MBS305-H1-knob, MBS305-H2-knob, MBS305-M-knob and MBS305-L-knob were respectively mixed with the half-antibody MBS305-hole at 1:1 molar ratio. The mixtures were added with Tris base buffer till pH 8.0 followed by reducing agent glutathione (GSH), and allowed to react overnight at 25° C. with low-speed stirring. Then, the mixtures were added with 2 M acetic acid solution to adjust pH to 5.5. The reducing agent was removed by ultrafiltration, to terminate the reaction. The antibodies as assembled were moved to low-salt Tris buffer (pH 8.0) and filtered with 0.2 μm film filters. The antibodies were purified using anions exchange chromatography and cation exchange chromatography. Anion exchange columns were balanced with low-salt Tris buffer (pH 8.0), and loaded with the antibody samples. The components that had passed through the columns were collected, and rinsed by low-salt Tris buffer (pH 8.0) until UV280 trended to the baseline. The collected samples were adjusted to pH 5.5 using an acetic acid solution, concentrated to 1 ml using a 30 kDa ultrafilter tube, and filtered using 0.2 μm membrane. Cation exchange columns were balanced with a low-concentration acetate buffer (pH 5.5), and loaded with the antibody samples. The low-concentration acetate buffer (pH 5.5) was used to balance the columns again, and elution was done using 20 CV acetate solutions (concentration at 0-100%, pH 5.5).

The bispecific antibodies consisting of MBS305-hole with MBS305-H1-knob, MBS305-H2-knob, MBS305-M-knob, and MBS305-L-konb respectively were termed as MBS305-H1-KIH, MBS305-H2-KIH, MBS305-M-KIH and MBS305-L-KIH. The purified antibodies, each with a purity higher than 90% as measured by mass spectrum, were further characterized below.

Example 15. Binding Capability of Anti-CD3/BCMA Bispecific Antibodies to Human CD3 and human BCMA The purified bispecific antibodies were tested for their binding capability to recombinant human CD3 and human BCMA proteins by ELISA, following the protocols in Example 4 and Example 9. EM801, an anti-CD3/BCMA antibody, was prepared using SEQ ID NOs: 43, 44, 45 and 46 in WO2016020332A1 and used as a positive control.

As shown in FIG. 12, MBS305-H1-KIH, MBS305-H2-KIH, MBS305-M-KIH, MBS305-L-KIH and EM801 all showed high binding capability to CD3D&E in a concentration dependent manner With GraphPad, the $EC_{50}$ values were determined and summarized in Table 6.

As shown in FIG. 13, MBS305-H1-KIH, MBS305-H2-KIH, MBS305-M-KIH, MBS305-L-KIH and EM801 all showed high binding capability to human BCMA in a concentration dependent manner. The $EC_{50}$ values were determined using GraphPad, and summarized in Table 6.

TABLE 6

| Binding capability of bispecific antibodies to CD3D&E and BCMA | | | | | |
|---|---|---|---|---|---|
| | $EC_{50}$ (ng/ml) | | | | |
| | MBS305-H1-KIH | MBS305-H2-KIH | MBS305-M-KIH | MBS305-L-KIH | EM801 |
| CD3D&E | 46.81 | 140.8 | 88.98 | 267 | 67.55 |
| BCMA | 11.68 | 12.44 | 13.7 | 19.57 | 22.58 |

Following the protocols in Example 5 and Example 10, the bispecific antibodies of the disclosure were tested for their binding affinity to CD3D&E and human BCMA. The $K_D$ values were determined and summarized in Table 7 and Table 8.

TABLE 7

| Binding affinity of bispecific antibodies to human CD3D&E complex | | | |
|---|---|---|---|
| | Ka | Kd | $K_D$ |
| 305-H1-KIH | 4.74E+04 | 3.84E−04 | 8.09E−09 |
| 305-H2-KIH | 3.03E+04 | 7.76E−03 | 2.56E−07 |
| 305-M-KIH | 4.36E+04 | 1.65E−03 | 3.79E−08 |
| 305-L-KIH | 1.79E+04 | 1.03E−02 | 6.75E−07 |
| EM801 | 1.38E+05 | 6.82E−03 | 4.93E−08 |

According to Table 7, all the bispecific antibodies, including EM801, were able to bind the CD3D&E complex.

Further, it can be seen from Table 8 that all the bispecific antibodies, including EM801, bound human BCMA with high affinity, and the binding affinity of the bispecific antibodies of the disclosure was even higher than that of EM801.

TABLE 8

Binding affinity of bispecific antibodies to human BCMA

| | Ka | Kd | $K_D$ |
|---|---|---|---|
| 305-H1-KIH | 8.07E+05 | 1.36E−04 | 1.68E−10 |
| 305-H2-KIH | 7.14E+05 | 1.47E−04 | 2.06E−10 |
| 305-M-KIH | 9.40E+05 | 9.89E−05 | 1.05E−10 |
| 305-L-KIH | 8.77E+05 | 2.32E−04 | 2.32E−10 |
| EM801 | 1.36E+06 | 3.22E−03 | 2.37E−09 |

Example 16. Binding Capability of Anti-CD3/BCMA Bispecific Antibodies to HEK293A/BCMA cells and Jurkat Cells Following the protocol of Example 6, the bispecific antibodies of the disclosure were tested for their binding capability to the HEK293A/human BCMA cells, HEK293A/monkey BCMA cells, and HEK293A/mouse BCMA cells as generated in Example 1. The results were shown in FIG. 14.

FIG. 14 showed the bispecific antibodies of the disclosure and EM801 were able to bind the HEK293A/human BCMA cells (A, B) and HEK293A/monkey BCMA cells (C, D) with high capability in a concentration dependent manner Specifically, the bispecific antibodies of the disclosure had similar binding capability to the HEK293A/human BCMA cells to EM801, and higher binding capability to the HEK293A/monkey BCMA cells than EM801. The $EC_{50}$ values were determined using GraphPad and summarized in Table 9.

TABLE 9

Binding capability of bispecific antibodies to BCMA-expressing HEK293A cells

| | $EC_{50}$ (ng/ml) | | | | |
|---|---|---|---|---|---|
| | MBS305-H1-KIH | MBS305-H2-KIH | MBS305-M-KIH | MBS305-L-KIH | EM801 |
| Human BCMA | 220.6 | 285.2 | 198.8 | 187.4 | 105.2 |
| Monkey BCMA | 337.3 | 373.1 | 229.6 | 289.0 | 792.7 |
| Mouse BCMA | / | / | / | / | 658.4 |

Following the protocol of Example 11, the bispecific antibodies of the disclosure were tested for their binding capability to Jurkat cells. The results were shown in FIG. 15.

TABLE 10

Binding capability of bispecific antibodies to Jurkat cells

| | MBS305-H1-KIH | MBS305-H2-KIH | MBS305-M-KIH | MBS305-L-KIH | EM801 |
|---|---|---|---|---|---|
| $EC_{50}$ (ng/ml) | 1.730 | 3.281 | 1.057 | 3.013 | 1.077 |

According to FIG. 15, the bispecific antibodies of the disclosure and EM801 all showed high binding capability to Jurkat cells in a concentration dependent manner. The binding $EC_{50}$ values were determined by GraphPad and summarized in Table 10.

Example 17. Effects of Anti-CD3/BCMA Bispecific Antibodies on T Cell Activation

The effect of free anti-CD3/BCMA bispecific antibodies on CD3/TCR signaling initiation was tested using primary human PBMCs. Briefly, PBMCs from healthy human donor's blood samples were collected by density gradient centrifugation, and suspended in RPMI complete medium (RPMI1640+10% FBS) at the cell density of $2.5 \times 10^5$/ml. The cell suspensions were seeded onto a 96-well cell culture plate, 200 µl per well, and 50 µl of the bispecific antibodies of the disclosure at different concentrations were further added to the plate. The mixtures were incubated at 37° C. with 5% $CO_2$ for 48 h. The supernatants were collected for determination of IFN-γ, IL-6 and TNF-α levels using ELISA kits (Cat #: 430107, Biolegend, US; Cat #: 430504, Biolegend, US; Cat #: 430207, Biolegend, US). EM801 was used as the positive control.

The results were shown in FIG. 16. It can be seen EM801 induced secretion of IFN-γ (A), IL-6 (B) and TNF-α (C) by PBMCs, while none of these cytokines were detected in supernatants from the plate well with the bispecific antibodies of the disclosure, suggesting EM801 is more likely to cause cytokine storm in clinical application than the bispecific antibodies of the disclosure.

Example 18. Capability of Anti-CD3/BCMA Bispecific Antibodies to Induce PBMC-Mediated $BCMA^+$ Tumor Cell Death and to Trigger T Cell Activation The bispecific antibodies of the disclosure were further measured for their capability to induce PBMC-mediated $BCMA^+$ cell death, using the HEK293A/human BCMA cells generated in Example 1 that expressed green fluorescent proteins (GFPs).

Briefly, the HEK293A/human BCMA cells were suspended in RPMI complete medium (RPMI+10% FBS) at the cell density of 2.5×10⁵/ml. Human PBMCs were collected by density gradient centrifugation, and suspended in RPMI complete medium (RPMI1640+10% FBS) at the cell density of 2.5×10⁵/ml. Then, 100 μl HEK293 cell suspensions and 100 μl PBMC cell suspensions were seeded onto a 96-well cell culture plate, with an effector-target ratio at 2:1, and 100 μl of the bispecific antibodies of the disclosure at different concentrations were further added to the plate. The cell/antibody mixtures were incubated at 37° C. with 5% $CO_2$ for 48 h, and 50 μl supernatants were collected from each well for determination of IL-6 and TNF-α levels using two kits (Cat #: 430504, Biolegend, US; Cat #: 430207, Biolegend, US).

The antibody-mediated target cell death was determined with LIVE/DEAD™ Fixable Violet Dead Cell Stain Kit (Cat #: L34964, Thermo Fisher, US). The cells above were washed with PBS for three times, and then incubated with the stain from the kit at 37° C. for 30 min. The cells were washed with PBS for three times, and subjected to FACS. The death rate of the GFP-expressing cells, i.e., the HEK293A/human BCMA cells, was determined.

As shown in FIG. 17 (A), EM801, when used at a relatively low concentration (1 ng/ml), triggered more target cell death than the bispecific antibodies of the disclosure, while the anti-tumor effects were comparable when EM801 and the bispecific antibodies of the disclosure were used at a relatively high concentration (10 ng/ml). The bispecific antibodies of the disclosure induced less cytokine secretion, including IL-6 (FIG. 17 (B)) and TNF-α (FIG. 17 (C)), than EM801 at both the low and high concentrations.

To sum up, the bispecific antibodies of the disclosure, when used at 10 ng/ml, provided the comparable anti-tumor effect but with less cytokine levels as compared to EM801. In other words, the bispecific antibodies of the disclosure are as efficacious as EM801 but much safer.

Exemplary sequences in the present application are summarized below.

```
                        Description/sequences/SEQ ID NO

VH-CDR1 of anti-BCMA antibody A6-3
NHIIH (SEQ ID NO: 1)

VH-CDR2 of anti-BCMA antibody A6-3
YINPYPGYHGYNDKFSG (SEQ ID NO: 2)

VH-CDR3 of anti-BCMA antibody A6-3
DGYYRDQDVLDY (SEQ ID NO: 3)

VL-CDR1 of anti-BCMA antibody A6-3
KASQDISQYLN (SEQ ID NO: 4)

VL-CDR2 of anti-BCMA antibody A6-3
YTSGLHP (SEQ ID NO: 5)

VL-CDR3 of anti-BCMA antibody A6-3
QQGYALPWT (SEQ ID NO: 6)

VH of anti-BCMA antibody A6-3
QVQLVQSGAEVKKPGASVKVSCKASGYTFTNHIIHWVRQAPGQGLEWMGYINPYPGYHGYND
KFSGRATMTSDTSTSTVYMELSSLRSEDTAVYYCARDGYYRDQDVLDYWGQGTLVTVSS (SEQ
ID NO: 7)

VL of anti-BCMA antibody A6-3
DIQMTQSPSSLSASVGDRVTITCKASQDISQYLNWYQQKPGKAPKLLIYYTSGLHPGVPSRFSGSG
SGTDFTFTISSLEPEDIATYYCQQGYALPWTFGQGTKVEIK (SEQ ID NO: 8)
Mutant VL of anti-BCMA antibody A6-3
DIQMTQSPSSLSASVGDRVTITCKASQDISQYLNWYQQKPGKAPKLLIYYTSGLHPGVPSRFSGSG
SGTDFTFTISSLEPEDEATYYCQQGYALPWTFGQGTKLTAKR (SEQ ID NO: 40)

VH-CDR1 of anti-CD3D & E antibody D1E9
DFAMH (SEQ ID NO: 9)

VH-CDR2 of anti-CD3D & E antibody D1E9
GITWNSGSVGYADSVKG (SEQ ID NO: 10)

VH-CDR3 of anti-CD3D & E antibody D1E9
DRSGYGHYYYGMDV (SEQ ID NO: 11)

VL-CDR1 of anti-CD3D & E antibody D1E9
RASTSVSHNVA (SEQ ID NO: 12)

VL-CDR2 of anti-CD3D & E antibody D1E9
GASTKVT (SEQ ID NO: 13)

VL-CDR3 of anti-CD3D & E antibody D1E9
QHYINWPLT (SEQ ID NO: 14)
```

| Description/sequences/SEQ ID NO |
|---|
| VH of anti-CD3D & E antibody D1E9<br>EVQLVESGGGLVQPGRSLRLSCAASGFTFDDFAMHWVRQAPGKGLEWVSGITWNSGSVGYADS<br>VKGRFTISRDNAKKSLYLQMNSLRAEDTALYYCAKDRSGYGHYYYGMDVWGQGTTVTVAS<br>(SEQ ID NO: 15) |
| VL of anti-CD3D & E antibody D1E9<br>EIVMTQSPATLSVSPGERATLSCRASTSVSHNVAWYQQKPGQAPRLLIYGASTKVTGIPARFSGS<br>GSGTEFTLTISSLQSEDFAVYYCQHYINWPLTFGGGTKVEIK (SEQ ID NO: 16) |
| VH-CDR1 of anti-CD3D & E antibody 7-1-A12<br>DYTMH (SEQ ID NO: 26) |
| VH-CDR2 of anti-CD3D & E antibody 7-1-A12<br>GISWNX1GX2JGYADSVKG (SEQ ID NO: 27) X1 = T, X2 = T, J = I<br>GISWNTGTIGYADSVKG |
| VH-CDR3 of anti-CD3D & E antibody 7-1-A12<br>DX1SGYGHYYX2GMDV (SEQ ID NO: 28) X1 = N, X2 = F<br>DNSGYGHYYFGMDV |
| VL-CDR1 of anti-CD3D & E antibody 7-1-A12<br>RASX1SVSX2NX3A (SEQ ID NO: 29) X1 = Q, X2 = R, X3 = V<br>RASQSVSRNVA |
| VL-CDR2 of anti-CD3D & E antibody 7-1-A12<br>GASTX1X2T (SEQ ID NO: 30) X1 = R, X2 = Q<br>GASTRQT |
| VL-CDR3 of anti-CD3D & E antibody 7-1-A12<br>QX1YX2NWPLX3 (SEQ ID NO: 31) X1 = S, X2 = I, X3 = Q<br>QSYINWPLQ |
| VH of anti-CD3D & E antibody 7-1-A12<br>EVQLVESGGGLVQPGRSLRLSCAASGFTFX1X2YX3MHWVRQAPGKGLEWVSGISWNX4GX5J<br>GYADSVKGRFTISRDNAKKSLYLQMNSLRAEDTALYYCAKDX6SGYGHYYX7GMDVWGQGTT<br>VTVAS (SEQ ID NO: 32) X1 = S, X2 = D, X3 = T, X4 = T, X5 = T, J = I, X6 = N, X7 = F<br>EVQLVESGGGLVQPGRSLRLSCAASGFTFSDYTMHWVRQAPGKGLEWVSGISWNTGTIGYADS<br>VKGRFTISRDNAKKSLYLQMNSLRAEDTALYYCAKDNSGYGHYYFGMDVWGQGTTVTVAS |
| VL of anti-CD3D & E antibody 7-1-A12<br>EIVMTQSPATLSVSPGERATLSCRASX1SVSX2NX3AWYQQKPGQAPRLLIYGASTX4X5TGIPARF<br>SGSGSGTEFTLTISSLQSEDFAVYYCQX6YX7NWPLX8FGGGTKVEIK (SEQ ID NO: 33) X1 = Q,<br>X2 = R, X3 = V, X4 = R, X5 = Q, X6 = S, X7 = I, X8 = Q<br>EIVMTQSPATLSVSPGERATLSCRASQSVSRNVAWYQQKPGQAPRLLIYGASTRQTGIPARFSGSG<br>SGTEFTLTISSLQSEDFAVYYCQSYINWPLQFGGGTKVEIK |
| VH-CDR1 of anti-CD3D & E antibody D8E5<br>SYSMH (SEQ ID NO: 41) |
| VH-CDR2 of anti-CD3D & E antibody D8E5<br>SEQ ID NO: 27, X1 = S, X2 = S, J = L<br>GISWNSGSLGYADSVKG |
| VH-CDR3 of anti-CD3D & E antibody D8E5<br>SEQ ID NO: 28, X1 = R, X2 = Y<br>DRSGYGHYYYGMDV |
| VL-CDR1 of anti-CD3D & E antibody D8E5<br>SEQ ID NO: 29, X1 = R, X2 = L, X3 = V<br>RASRSVSLNVA |
| VL-CDR2 of anti-CD3D & E antibody D8E5<br>SEQ ID NO: 30, X1 = K, X2 = Y<br>GASTKYT |
| VL-CDR3 of anti-CD3D & E antibody D8E5<br>SEQ ID NO: 31, X1 = Q, X2 = I, X3 = T<br>QQYINWPLT |
| VH of anti-CD3D & E antibody D8E5<br>SEQ ID NO: 32, X1 = D, X2 = S, X3 = S, X4 = S, X5 = S, J = L, X6 = R, X7 = Y<br>EVQLVESGGGLVQPGRSLRLSCAASGFTFDSYSMHWVRQAPGKGLEWVSGISWNSGSLGYADS<br>VKGRFTISRDNAKKSLYLQMNSLRAEDTALYYCAKDRSGYGHYYYGMDVWGQGTTVTVAS |

| Description/sequences/SEQ ID NO |
|---|
| VL of anti-CD3D & E antibody D8E5<br>SEQ ID NO: 33, X1 = R, X2 = L, X3 = V, X4 = K, X5 = Y, X6 = Q, X7 = I, X8 = T<br>EIVMTQSPATLSVSPGERATLSCRASRSVSLNVAWYQQKPGQAPRLLIYGASTKYTGIPARFSGSG<br>SGTEFTLTISSLQSEDFAVYYCQQYINWPLTFGGGTKVEIK<br><br>VH-CDR1 of anti-CD3D & E antibody D12A4<br>DYAMH (SEQ ID NO: 42)<br><br>VH-CDR2 of anti-CD3D & E antibody D12A4<br>GISWNX1GX2X3GYADSVKG (SEQ ID NO: 27) X1 = H, X2 = H, J = I<br>GISWNHGHIGYADSVKG<br><br>VH-CDR3 of anti-CD3D & E antibody D12A4<br>SEQ ID NO: 28, X1 = N, X2 = Y<br>DNSGYGHYYYGMDV<br><br>VL-CDR1 of anti-CD3D & E antibody D12A4<br>SEQ ID NO: 29, X1 = R, X2 = R, X3 = L<br>RASRSVSRNLA<br><br>VL-CDR2 of anti-CD3D & E antibody D12A4<br>SEQ ID NO: 30, X1 = K, X2 = P<br>GASTKPT<br><br>VL-CDR3 of anti-CD3D & E antibody D12A4<br>SEQ ID NO: 31, X1 = H, X2 = T, X3 = R<br>QHYTNWPLR<br><br>VH of anti-CD3D & E antibody D12A4<br>SEQ ID NO: 32, X1 = G, X2 = D, X3 = A, X4 = H, X5 = H, J = I, X6 = N, X7 = Y<br>EVQLVESGGGLVQPGRSLRLSCAASGFTFGDYAMHWVRQAPGKGLEWVSGISWNHGHIGYAD<br>SVKGRFTISRDNAKKSLYLQMNSLRAEDTALYYCAKDNSGYGHYYYGMDVWGQGTTVTVAS<br><br>VL of anti-CD3D & E antibody D12A4<br>SEQ ID NO: 33, X1 = R, X2 = R, X3 = L, X4 = K, X5 = P, X6 = H, X7 = T, X8 = R<br>EIVMTQSPATLSVSPGERATLSCRASRSVSRNLAWYQQKPGQAPRLLIYGASTKPTGIPARFSGSG<br>SGTEFTLTISSLQSEDFAVYYCQHYTNWPLRFGGGTKVEIK<br><br>human IgG1 Fc-wildtype<br>ASTKGPSVFPLAPSSKSTSGGTAALGCLVKDYFPEPVTVSWNSGALTSGVHTFPAVLQSSGLYSLS<br>SVVTVPSSSLGTQTYICNVNHKPSNTKVDKKVEPKSCDKTHTCPPCPAPEX1X2GGPSVFLFPPKP<br>KDTLMISRTPEVTCVVVDVSHEDPEVKFNWYVDGVEVHNAKTKPREEQYX3STYRVVSVLTVLH<br>QDWLNGKEYKCKVSNKALPAPIEKTISKAKGQPREPQVYTLPPSREEMTKNQVSLX4CX5VKGF<br>YPSDIAVEWESNGQPENNYKTTPPVLDSDGSFFLX6SKLTVDKSRWQQGNVFSCSVMHEALHNH<br>YTQKSLSLSPGK (SEQ ID NO: 17) X1 = L, X2 = L, X3 = N, X4 = T, X5 = L, X6 = Y<br>ASTKGPSVFPLAPSSKSTSGGTAALGCLVKDYFPEPVTVSWNSGALTSGVHTFPAVLQSSGLYSLS<br>SVVTVPSSSLGTQTYICNVNHKPSNTKVDKKVEPKSCDKTHTCPPCPAPELLGGPSVFLFPPKPKD<br>TLMISRTPEVTCVVVDVSHEDPEVKFNWYVDGVEVHNAKTKPREEQYNSTYRVVSVLTVLHQD<br>WLNGKEYKCKVSNKALPAPIEKTISKAKGQPREPQVYTLPPSREEMTKNQVSLTCLVKGFYPSDI<br>AVEWESNGQPENNYKTTPPVLDSDGSFFLYSKLTVDKSRWQQGNVFSCSVMHEALHNHYTQKS<br>LSLSPGK<br><br>IgG1 Fc L234A/L235A/N297A<br>SEQ ID NO: 17, X1 = A, X2 = A, X3 = A, X4 = T, X5 = L, X6 = Y<br>ASTKGPSVFPLAPSSKSTSGGTAALGCLVKDYFPEPVTVSWNSGALTSGVHTFPAVLQSSGLYSLS<br>SVVTVPSSSLGTQTYICNVNHKPSNTKVDKKVEPKSCDKTHTCPPCPAPEAAGGPSVFLFPPKPKD<br>TLMISRTPEVTCVVVDVSHEDPEVKFNWYVDGVEVHNAKTKPREEQYASTYRVVSVLTVLHQD<br>WLNGKEYKCKVSNKALPAPIEKTISKAKGQPREPQVYTLPPSREEMTKNQVSLTCLVKGFYPSDI<br>AVEWESNGQPENNYKTTPPVLDSDGSFFLYSKLTVDKSRWQQGNVFSCSVMHEALHNHYTQKS<br>LSLSPGK<br><br>IgG1 Fc L234A/L235A/N297A/T366W in knob-containing long chain of MBS305-H1, MBS305-H2,<br>MBS305-M and MBS305-L<br>SEQ ID NO: 17, X1 = A, X2 = A, X3 = A, X4 = W, X5 = L, X6 = Y<br>ASTKGPSVFPLAPSSKSTSGGTAALGCLVKDYFPEPVTVSWNSGALTSGVHTFPAVLQSSGLYSLS<br>SVVTVPSSSLGTQTYICNVNHKPSNTKVDKKVEPKSCDKTHTCPPCPAPEAAGGPSVFLFPPKPKD<br>TLMISRTPEVTCVVVDVSHEDPEVKFNWYVDGVEVHNAKTKPREEQYASTYRVVSVLTVLHQD<br>WLNGKEYKCKVSNKALPAPIEKTISKAKGQPREPQVYTLPPSREEMTKNQVSLWCLVKGFYPSD<br>IAVEWESNGQPENNYKTTPPVLDSDGSFFLYSKLTVDKSRWQQGNVFSCSVMHEALHNHYTQKS<br>LSLSPGK |

| Description/sequences/SEQ ID NO |
|---|
| IgG1 Fc of hole-containing long chain of MBS305-H1, MBS305-H2, MBS305-M and MBS305-L<br>SEQ ID NO: 17, X1 = A, X2 = A, X3 = A, X4 = S, X5 = A, X6 = V<br>ASTKGPSVFPLAPSSKSTSGGTAALGCLVKDYFPEPVTVSWNSGALTSGVHTFPAVLQSSGLYSLS<br>SVVTVPSSSLGTQTYICNVNHKPSNTKVDKKVEPKSCDKTHTCPPCPAPEAAGGPSVFLFPPKPKD<br>TLMISRTPEVTCVVVDVSHEDPEVKFNWYVDGVEVHNAKTKPREEQYASTYRVVSVLTVLHQD<br>WLNGKEYKCKVSNKALPAPIEKTISKAKGQPREPQVYTLPPSREEMTKNQVSLSCAVKGFYPSDI<br>AVEWESNGQPENNYKTTPPVLDSDGSFFLVSKLTVDKSRWQQGNVFSCSVMHEALHNHYTQKS<br>LSLSPGK |
| kappa light chain constant region<br>RTVAAPSVFIFPPSDEQLKSGTASVVCLLNNFYPREAKVQWKVDNALQSGNSQESVTEQDSKDST<br>YSLSSTLTLSKADYEKHKVYACEVTHQGLSSPVTKSFNRGEC (SEQ ID NO: 18) |
| linker<br>GGGGSGGGGSGGGGSGGGGS (SEQ ID NO: 19)<br>GGGGSGGGGSGGGGS (SEQ ID NO: 20) |
| knob-containing long chain of MBS305-H2 (anti-BCMA scFv-linker-anti-CD3 D1E9's HV-HC)<br>QVQLVQSGAEVKKPGASVKVSCKASGYTFTNHIIHWVRQAPGQGLEWMGYINPYPGYHGYND<br>KFSGRATMTSDTSTSTVYMELSSLRSEDTAVYYCARDGYYRDQDVLDYWGQGTLVTVSSGGGG<br>SGGGGSGGGGSGGGGSDIQMTQSPSSLSASVGDRVTITCKASQDISQYLNWYQQKPGKAPKLLIY<br>YTSGLHPGVPSRFSGSGSGTDFTFTISSLEPEDEATYYCQQGYALPWTFGQGTKLTAKRGGGGSG<br>GGGSGGGGSEVQLVESGGGLVQPGRSLRLSCAASGFTFDDFAMHWVRQAPGKGLEWVSGITWN<br>SGSVGYADSVKGRFTISRDNAKKSLYLQMNSLRAEDTALYYCAKDRSGYGHYYYGMDVWGQG<br>TTVTVASASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPEAAGGPSVFL<br>FPPKPKDTLMISRTPEVTCVVVDVSHEDPEVKFNWYVDGVEVHNAKTKPREEQYASTYRVVSVL<br>TVLHQDWLNGKEYKCKVSNKALPAPIEKTISKAKGQPREPQVYTLPPSREEMTKNQVSLWCLVK<br>GFYPSDIAVEWESNGQPENNYKTTPPVLDSDGSFFLYSKLTVDKSRWQQGNVFSCSVMHEALHN<br>HYTQKSLSLSPGK (SEQ ID NO: 34) |
| short chain of MBS305-H2 pairing with the knob-containing long chain (anti-CD3 D1E9's LV-LC)<br>EIVMTQSPATLSVSPGERATLSCRASTSVSHNVAWYQQKPGQAPRLLIYGASTKVTGIPARFSGSG<br>SGTEFTLTISSLQSEDFAVYYCQHYINWPLTFGGGTKVEIKRTVAAPSVFIFPPSDEQLKSGTASVVC<br>LLNNFYPREAKVQWKVDNALQSGNSQESVTEQDSKDSTYSLSSTLTLSKADYEKHKVYACEVTH<br>QGLSSPVTKSFNRGEC (SEQ ID NO: 35) |
| Knob-containing long chain of MBS305-H1 (anti-BCMA scFv-linker-anti-CD3 7-1-A12's HV-HC)<br>QVQLVQSGAEVKKPGASVKVSCKASGYTFTNHIIHWVRQAPGQGLEWMGYINPYPGYHGYND<br>KFSGRATMTSDTSTSTVYMELSSLRSEDTAVYYCARDGYYRDQDVLDYWGQGTLVTVSSGGG<br>GSGGGGSGGGGSGGGGSDIQMTQSPSSLSASVGDRVTITCKASQDISQYLNWYQQKPGKAPKLL<br>IYYTSGLHPGVPSRFSGSGSGTDFTFTISSLEPEDEATYYCQQGYALPWTFGQGTKLTAKRGGGG<br>SGGGGSGGGGSEVQLVESGGGLVQPGRSLRLSCAASGFTFX1X2YX3MHWVRQAPGKGLEWVS<br>GISWNX4GX5JGYADSVKGRFTISRDNAKKSLYLQMNSLRAEDTALYYCAKDX6SGYGHYYX7<br>GMDVWGQGTTVTVASASTKGPSVFPLAPSSKSTSGGTAALGCLVKDYFPEPVTVSWNSGALTSG<br>VHTFPAVLQSSGLYSLSSVVTVPSSSLGTQTYICNVNHKPSNTKVDKKVEPKSCDKTHTCPPCPA<br>PEAAGGPSVFLFPPKPKDTLMISRTPEVTCVVVDVSHEDPEVKFNWYVDGVEVHNAKTKPREEQ<br>YASTYRVVSVLTVLHQDWLNGKEYKCKVSNKALPAPIEKTISKAKGQPREPQVYTLPPSREEMT<br>KNQVSLWCLVKGFYPSDIAVEWESNGQPENNYKTTPPVLDSDGSFFLYSKLTVDKSRWQQGNV<br>FSCSVMHEALHNHYTQKSLSLSPGK (SEQ ID NO: 36) X1 = S, X2 = D, X3 = T, X4 = T, X5 = T, J = I, X6 = N, X7 = F<br>QVQLVQSGAEVKKPGASVKVSCKASGYTFTNHIIHWVRQAPGQGLEWMGYINPYPGYHGYND<br>KFSGRATMTSDTSTSTVYMELSSLRSEDTAVYYCARDGYYRDQDVLDYWGQGTLVTVSSGGG<br>GSGGGGSGGGGSGGGGSDIQMTQSPSSLSASVGDRVTITCKASQDISQYLNWYQQKPGKAPKLL<br>IYYTSGLHPGVPSRFSGSGSGTDFTFTISSLEPEDEATYYCQQGYALPWTFGQGTKLTAKRGGGG<br>SGGGGSGGGGSEVQLVESGGGLVQPGRSLRLSCAASGFTFSDYTMHWVRQAPGKGLEWVSGIS<br>WNTGTIGYADSVKGRFTISRDNAKKSLYLQMNSLRAEDTALYYCAKDNSGYGHYYFGMDVWG<br>QGTTVTVASASTKGPSVFPLAPSSKSTSGGTAALGCLVKDYFPEPVTVSWNSGALTSGVHTFPAV<br>LQSSGLYSLSSVVTVPSSSLGTQTYICNVNHKPSNTKVDKKVEPKSCDKTHTCPPCPAPEAAGGP<br>SVFLFPPKPKDTLMISRTPEVTCVVVDVSHEDPEVKFNWYVDGVEVHNAKTKPREEQYASTYRV<br>VSVLTVLHQDWLNGKEYKCKVSNKALPAPIEKTISKAKGQPREPQVYTLPPSREEMTKNQVSLW<br>CLVKGFYPSDIAVEWESNGQPENNYKTTPPVLDSDGSFFLYSKLTVDKSRWQQGNVFSCSVMHE<br>ALHNHYTQKSLSLSPGK<br>Obtained by linking, from N-terminus to C-terminus, SEQ ID NO: 7, SEQ ID NO: 19, SEQ ID NO: 8 (X1 = E, X2 = L, X3 = T, X4 = A, X5 = R), SEQ ID NO: 20, SEQ ID NO: 32(X1 = S,X2 = D,X3 = T,X4 = T, X5 = T, J = I, X6 = N, X7 = F), and SEQ ID NO: 17(X1 = A,X2 = A,X3 = A, X4 = W,X5 = L, X6 = Y) |
| short chain of MBS305-H1 pairing with the knob-containing long chain (anti-CD3 7-1-A12's LV-LC)<br>EIVMTQSPATLSVSPGERATLSCRASX1SVSX2NX3AWYQQKPGQAPRLLIYGASTX4X5TGIPARF<br>SGSGSGTEFTLTISSLQSEDFAVYYCQX6YX7NWPLX8FGGGTKVEIKRTVAAPSVFIFPPSDEQLK<br>SGTASVVCLLNNFYPREAKVQWKVDNALQSGNSQESVTEQDSKDSTYSLSSTLTLSKADYEKHK<br>VYACEVTHQGLSSPVTKSFNRGEC (SEQ ID NO: 37) X1 = Q, X2 = R, X3 = V, X4 = R, X5 = Q, X6 = S, X7 = I, X8 = Q<br>EIVMTQSPATLSVSPGERATLSCRASQSVSRNVAWYQQKPGQAPRLLIYGASTRQTGIPARFSGS<br>GSGTEFTLTISSLQSEDFAVYYCQSYINWPLQFGGGTKVEIKRTVAAPSVFIFPPSDEQLKSGTASV |

| Description/sequences/SEQ ID NO |
|---|
| VCLLNNFYPREAKVQWKVDNALQSGNSQESVTEQDSKDSTYSLSSTLTLSKADYEKHKVYACE<br>VTHQGLSSPVTKSFNRGEC<br>Obtained by linking, from N-terminus to C-terminus, SEQ ID NO: 33 (X1 = Q, X2 = R, X3 = V, X4 = R,<br>X5 = Q, X6 = S, X7 = I, X8 = Q) and SEQ ID NO: 18 |
| knob-containing long chain of MBS305-M (anti-BCMA scFv-linker-anti-CD3 D8E5's HV-HC)<br>SEQ ID NO: 36, X1 = D, X2 = S, X3 = S, X4 = S, X5 = S, J = L, X6 = R, X7 = Y<br>QVQLVQSGAEVKKPGASVKVSCKASGYTFTNHIIHWVRQAPGQGLEWMGYINPYPGYHGYND<br>KFSGRATMTSDTSTSTVYMELSSLRSEDTAVYYCARDGYYRDQDVLDYWGQGTLVTVSSGGG<br>GSGGGGSGGGGSGGGGSDIQMTQSPSSLSASVGDRVTITCKASQDISQYLNWYQQKPGKAPKLL<br>IYYTSGLHPGVPSRFSGSGSGTDFTFTISSLEPEDEATYYCQQGYALPWTFGQGTKLTAKRGGGG<br>SGGGGSGGGGSEVQLVESGGGLVQPGRSLRLSCAASGFTFDSYSMHWVRQAPGKGLEWVSGIS<br>WNSGSLGYADSVKGRFTISRDNAKKSLYLQMNSLRAEDTALYYCAKDRSGYGHYYYGMDVW<br>GQGTTVTVASASTKGPSVFPLAPSSKSTSGGTAALGCLVKDYFPEPVTVSWNSGALTSGVHTFPA<br>VLQSSGLYSLSSVVTVPSSSLGTQTYICNVNHKPSNTKVDKKVEPKSCDKTHTCPPCPAPEAAGG<br>PSVFLFPPKPKDTLMISRTPEVTCVVVDVSHEDPEVKFNWYVDGVEVHNAKTKPREEQYASTYR<br>VVSVLTVLHQDWLNGKEYKCKVSNKALPAPIEKTISKAKGQPREPQVYTLPPSREEMTKNQVSL<br>WCLVKGFYPSDIAVEWESNGQPENNYKTTPPVLDSDGSFFLYSKLTVDKSRWQQGNVFSCSVM<br>HEALHNHYTQKSLSLSPGK<br>Obtained by linking, from N-terminus to C-terminus, SEQ ID NO: 7, SEQ ID NO: 19, SEQ ID NO: 8<br>(X1 = E, X2 = L, X3 = T, X4 = A, X5 = R), SEQ ID NO: 20, SEQ ID NO: 32 (X1 = D, X2 = S, X3 = S, X4 = S,<br>X5 = S, J = L, X6 = R, X7 = Y), and SEQ ID NO: 17(X1 = A, X2 = A, X3 = A, X4 = W, X5 = L, X6 = Y) |
| short chain of MBS305-M pairing with knob-containing long chain (anti-CD3 D8E5's LV-LC)<br>SEQ ID NO: 37, X1 = R, X2 = L, X3 = V, X4 = K, X5 = Y, X6 = Q, X7 = I, X8 = T<br>EIVMTQSPATLSVSPGERATLSCRASRSVSLNVAWYQQKPGQAPRLLIYGASTKYTGIPARFSGS<br>GSGTEFTLTISSLQSEDFAVYYCQQYINWPLTFGGGTKVEIKRTVAAPSVFIFPPSDEQLKSGTASV<br>VCLLNNFYPREAKVQWKVDNALQSGNSQESVTEQDSKDSTYSLSSTLTLSKADYEKHKVYACE<br>VTHQGLSSPVTKSFNRGEC<br>Obtained by linking, from N-terminus to C-terminus, SEQ ID NO: 33 (X1 = R, X2 = L, X3 = V, X4 = K,<br>X5 = Y, X6 = Q, X7 = I, X8 = T) and SEQ ID NO: 18 |
| knob-containing long chain of MBS305-L (anti-BCMA scFv-linker-anti-CD3 D12A4's HV-HC)<br>SEQ ID NO: 36, X1 = G, X2 = D, X3 = A, X4 = H, X5 = H, J = I, X6 = N, X7 = Y<br>QVQLVQSGAEVKKPGASVKVSCKASGYTFTNHIIHWVRQAPGQGLEWMGYINPYPGYHGYND<br>KFSGRATMTSDTSTSTVYMELSSLRSEDTAVYYCARDGYYRDQDVLDYWGQGTLVTVSSGGG<br>GSGGGGSGGGGSGGGGSDIQMTQSPSSLSASVGDRVTITCKASQDISQYLNWYQQKPGKAPKLL<br>IYYTSGLHPGVPSRFSGSGSGTDFTFTISSLEPEDEATYYCQQGYALPWTFGQGTKLTAKRGGGG<br>SGGGGSGGGGSEVQLVESGGGLVQPGRSLRLSCAASGFTFGDYAMHWVRQAPGKGLEWVSGIS<br>WNHGHIGYADSVKGRFTISRDNAKKSLYLQMNSLRAEDTALYYCAKDNSGYGHYYYGMDVW<br>GQGTTVTVASASTKGPSVFPLAPSSKSTSGGTAALGCLVKDYFPEPVTVSWNSGALTSGVHTFPA<br>VLQSSGLYSLSSVVTVPSSSLGTQTYICNVNHKPSNTKVDKKVEPKSCDKTHTCPPCPAPEAAGG<br>PSVFLFPPKPKDTLMISRTPEVTCVVVDVSHEDPEVKFNWYVDGVEVHNAKTKPREEQYASTYR<br>VVSVLTVLHQDWLNGKEYKCKVSNKALPAPIEKTISKAKGQPREPQVYTLPPSREEMTKNQVSL<br>WCLVKGFYPSDIAVEWESNGQPENNYKTTPPVLDSDGSFFLYSKLTVDKSRWQQGNVFSCSVM<br>HEALHNHYTQKSLSLSPGK<br>Obtained by linking, from N-terminus to C-terminus, SEQ ID NO: 7, SEQ ID NO: 19, SEQ ID NO: 8<br>(X1 = E, X2 = L, X3 = T, X4 = A, X5 = R), SEQ ID NO: 20, SEQ ID NO: 32 (X1 = G, X2 = D, X3 = A, X4 = H,<br>X5 = H, J = I, X6 = N, X7 = Y), and SEQ ID NO: 17(X1 = A, X2 = A, X3 = A, X4 = W, X5 = L, X6 = Y) |
| short chain of MBS305-L pairing with knob-containing long chain (anti-CD3 D12A4's LV-LC)<br>SEQ ID NO: 37, X1 = R, X2 = R, X3 = L, X4 = K, X5 = P, X6 = H, X7 = T, X8 = R<br>EIVMTQSPATLSVSPGERATLSCRASRSVSRNLAWYQQKPGQAPRLLIYGASTKPTGIPARFSGS<br>SGTEFTLTISSLQSEDFAVYYCQHYTNWPLRFGGGTKVEIKRTVAAPSVFIFPPSDEQLKSGTASV<br>VCLLNNFYPREAKVQWKVDNALQSGNSQESVTEQDSKDSTYSLSSTLTLSKADYEKHKVYACE<br>VTHQGLSSPVTKSFNRGEC<br>Obtained by linking, from N-terminus to C-terminus, SEQ ID NO: 33 (X1 = R, X2 = R, X3 = L, X4 = K,<br>X5 = P, X6 = H, X7 = T, X8 = R) and SEQ ID NO: 18 |
| hole-containing long chain of MBS305-H1, MBS305-H2, MBS305-M, and MBS305-L (anti-BCMA HV-HC)<br>QVQLVQSGAEVKKPGASVKVSCKASGYTFTNHIIHWVRQAPGQGLEWMGYINPYPGYHGYND<br>KFSGRATMTSDTSTSTVYMELSSLRSEDTAVYYCARDGYYRDQDVLDYWGQGTLVTVSSASTK<br>GPSVFPLAPSSKSTSGGTAALGCLVKDYFPEPVTVSWNSGALTSGVHTFPAVLQSSGLYSLSSVVT<br>VPSSSLGTQTYICNVNHKPSNTKVDKKVEPKSCDKTHTCPPCPAPEAAGGPSVFLFPPKPKDTLMI<br>SRTPEVTCVVVDVSHEDPEVKFNWYVDGVEVHNAKTKPREEQYASTYRVVSVLTVLHQDWLNG<br>KEYKCKVSNKALPAPIEKTISKAKGQPREPQVYTLPPSREEMTKNQVSLSCAVKGFYPSDIAVEW<br>ESNGQPENNYKTTPPVLDSDGSFFLVSKLTVDKSRWQQGNVFSCSVMHEALHNHYTQKSLSLSP<br>GK (SEQ ID NO: 38) |
| short chain of MBS305-H1, MBS305-H2, MBS305-M and MBS305-L pairing with hole-containing long chain (anti-BCMA LV-LC)<br>DIQMTQSPSSLSASVGDRVTITCKASQDISQYLNWYQQKPGKAPKLLIYYTSGLHPGVPSRFSGSG<br>SGTDFTFTISSLEPEDIATYYCQQGYALPWTFGQGTKVEIKRTVAAPSVFIFPPSDEQLKSGTASVV<br>CLLNNFYPREAKVQWKVDNALQSGNSQESVTEQDSKDSTYSLSSTLTLSKADYEKHKVYACEVT<br>HQGLSSPVTKSFNRGEC (SEQ ID NO: 39) |

```
              Description/sequences/SEQ ID NO human BCMA
MLQMAGQCSQNEYFDSLLHACIPCQLRCSSNTPPLTCQRYCNASVTNSVKGTNAILWTCLGLSLII
SLAVFVLMFLLRKINSEPLKDEFKNTGSGLLGMANIDLEKSRTGDEIILPRGLEYTVEECTCEDCIK
SKPKVDSDHCFPLPAMEEGATILVTTKTNDYCKSLPAALSATEIEKSISAR (SEQ ID NO: 21)

monkey BCMA
MLQMARQCSQNEYFDSLLHDCKPCQLRCSSTPPLTCQRYCNASMTNSVKGMNAILWTCLGLSLII
SLAVFVLTFLLRKMSSEPLKDEFKNTGSGLLGMANIDLEKGRTGDEIVLPRGLEYTVEECTCEDCI
KNKPKVDSDHCFPLPAMEEGATILVTTKTNDYCNSLSAALSVTEIEKSISAR (SEQ ID NO: 22)

mouse BCMA
MAQQCFHSEYFDSLLHACKPCHLRCSNPPATCQPYCDPSVTSSVKGTYTVLWIFLGLTLVLSLALF
TISFLLRKMNPEALKDEPQSPGQLDGSAQLDKADTELTRIRAGDDRIFPRSLEYTVEECTCEDCVK
SKPKGDSDHFFPLPAMEEGATILVTTKTGDYGKSSVPTALQSVMGMEKPTHTR (SEQ ID NO: 23)

human BAFFR
MRRGPRSLRGRDAPAPTPCVPAECFDLLVRHCVACGLLRTPRPKPAGASSPAPRTALQPQESVGAG
AGEAALPLPGLLFGAPALLGLALVLALVLVGLVSWRRRQRRLRGASSAEAPDGDKDAPEPLDKVI
ILSPGISDATAPAWPPPGEDPGTTPPGHSVPVPATELGSTELVTTKTAGPEQQ (SEQ ID NO: 24)

human TACI
MSGLGRSRRGGRSRVDQEERFPQGLWTGVAMRSCPEEQYWDPLLGTCMSCKTICNHQSQRTCA
AFCRSLSCRKEQGKFYDHLLRDCISCASICGQHPKQCAYFCENKLRSPVNLPPELRRQRSGEVEN
NSDNSGRYQGLEHRGSEASPALPGLKLSADQVALVYSTLGLCLCAVLCCFLVAVACFLKKRGDPC
SCQPRSRPRQSPAKSSQDHAMEAGSPVSTSPEPVETCSFCFPECRAPTQESAVTPGTPDPTCAGRW
GCHTRTTVLQPCPHIPDSGLGIVCVPAQEGGPGA (SEQ ID NO: 25)
```

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

```
                          SEQUENCE LISTING

Sequence total quantity: 42
SEQ ID NO: 1           moltype = AA  length = 5
FEATURE                Location/Qualifiers
source                 1..5
                       mol_type = protein
                       organism = synthetic construct
SEQUENCE: 1
NHIIH                                                                5

SEQ ID NO: 2           moltype = AA  length = 17
FEATURE                Location/Qualifiers
source                 1..17
                       mol_type = protein
                       organism = synthetic construct
SEQUENCE: 2
YINPYPGYHG YNDKFSG                                                  17

SEQ ID NO: 3           moltype = AA  length = 12
FEATURE                Location/Qualifiers
source                 1..12
                       mol_type = protein
                       organism = synthetic construct
SEQUENCE: 3
DGYYRDQDVL DY                                                       12

SEQ ID NO: 4           moltype = AA  length = 11
FEATURE                Location/Qualifiers
source                 1..11
                       mol_type = protein
                       organism = synthetic construct
SEQUENCE: 4
KASQDISQYL N                                                        11

SEQ ID NO: 5           moltype = AA  length = 7
FEATURE                Location/Qualifiers
source                 1..7
                       mol_type = protein
                       organism = synthetic construct
SEQUENCE: 5
YTSGLHP                                                              7
```

```
SEQ ID NO: 6              moltype = AA   length = 9
FEATURE                   Location/Qualifiers
source                    1..9
                          mol_type = protein
                          organism = synthetic construct
SEQUENCE: 6
QQGYALPWT                                                                  9

SEQ ID NO: 7              moltype = AA   length = 121
FEATURE                   Location/Qualifiers
source                    1..121
                          mol_type = protein
                          organism = synthetic construct
SEQUENCE: 7
QVQLVQSGAE VKKPGASVKV SCKASGYTFT NHIIHWVRQA PGQGLEWMGY INPYPGYHGY          60
NDKFSGRATM TSDTSTSTVY MELSSLRSED TAVYYCARDG YYRDQDVLDY WGQGTLVTVS         120
S                                                                        121

SEQ ID NO: 8              moltype = AA   length = 107
FEATURE                   Location/Qualifiers
source                    1..107
                          mol_type = protein
                          organism = synthetic construct
SEQUENCE: 8
DIQMTQSPSS LSASVGDRVT ITCKASQDIS QYLNWYQQKP GKAPKLLIYY TSGLHPGVPS          60
RFSGSGSGTD FTFTISSLEP EDIATYYCQQ GYALPWTFGQ GTKVEIK                       107

SEQ ID NO: 9              moltype = AA   length = 5
FEATURE                   Location/Qualifiers
source                    1..5
                          mol_type = protein
                          organism = synthetic construct
SEQUENCE: 9
DFAMH                                                                      5

SEQ ID NO: 10             moltype = AA   length = 17
FEATURE                   Location/Qualifiers
source                    1..17
                          mol_type = protein
                          organism = synthetic construct
SEQUENCE: 10
GITWNSGSVG YADSVKG                                                        17

SEQ ID NO: 11             moltype = AA   length = 14
FEATURE                   Location/Qualifiers
source                    1..14
                          mol_type = protein
                          organism = synthetic construct
SEQUENCE: 11
DRSGYGHYYY GMDV                                                           14

SEQ ID NO: 12             moltype = AA   length = 11
FEATURE                   Location/Qualifiers
source                    1..11
                          mol_type = protein
                          organism = synthetic construct
SEQUENCE: 12
RASTSVSHNV A                                                              11

SEQ ID NO: 13             moltype = AA   length = 7
FEATURE                   Location/Qualifiers
source                    1..7
                          mol_type = protein
                          organism = synthetic construct
SEQUENCE: 13
GASTKVT                                                                    7

SEQ ID NO: 14             moltype = AA   length = 9
FEATURE                   Location/Qualifiers
source                    1..9
                          mol_type = protein
                          organism = synthetic construct
SEQUENCE: 14
QHYINWPLT                                                                  9

SEQ ID NO: 15             moltype = AA   length = 123
FEATURE                   Location/Qualifiers
source                    1..123
```

-continued

```
                        mol_type = protein
                        organism = synthetic construct
SEQUENCE: 15
EVQLVESGGG LVQPGRSLRL SCAASGFTFD DFAMHWVRQA PGKGLEWVSG ITWNSGSVGY    60
ADSVKGRFTI SRDNAKKSLY LQMNSLRAED TALYYCAKDR SGYGHYYYGM DVWGQGTTVT   120
VAS                                                                 123

SEQ ID NO: 16           moltype = AA   length = 107
FEATURE                 Location/Qualifiers
source                  1..107
                        mol_type = protein
                        organism = synthetic construct
SEQUENCE: 16
EIVMTQSPAT LSVSPGERAT LSCRASTSVS HNVAWYQQKP GQAPRLLIYG ASTKVTGIPA    60
RFSGSGSGTE FTLTISSLQS EDFAVYYCQH YINWPLTFGG GTKVEIK                 107

SEQ ID NO: 17           moltype = AA   length = 330
FEATURE                 Location/Qualifiers
source                  1..330
                        mol_type = protein
                        organism = synthetic construct
VARIANT                 117
                        note = L or A
VARIANT                 118
                        note = L or A
VARIANT                 180
                        note = N or A
VARIANT                 249
                        note = T, W or S
VARIANT                 251
                        note = L or A
VARIANT                 290
                        note = Y or V
SEQUENCE: 17
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEXXGG   120
PSVFLFPPKP KDTLMISRTP EVTCVVVDVS HEDPEVKFNW YVDGVEVHNA KTKPREEQYX   180
STYRVVSVLT VLHQDWLNGK EYKCKVSNKA LPAPIEKTIS KAKGQPREPQ VYTLPPSREE   240
MTKNQVSLXC XVKGFYPSDI AVEWESNGQP ENNYKTTPPV LDSDGSFFLX SKLTVDKSRW   300
QQGNVFSCSV MHEALHNHYT QKSLSLSPGK                                    330

SEQ ID NO: 18           moltype = AA   length = 107
FEATURE                 Location/Qualifiers
source                  1..107
                        mol_type = protein
                        organism = synthetic construct
SEQUENCE: 18
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 19           moltype = AA   length = 20
FEATURE                 Location/Qualifiers
source                  1..20
                        mol_type = protein
                        organism = synthetic construct
SEQUENCE: 19
GGGGSGGGGS GGGGSGGGGS                                                20

SEQ ID NO: 20           moltype = AA   length = 15
FEATURE                 Location/Qualifiers
source                  1..15
                        mol_type = protein
                        organism = synthetic construct
SEQUENCE: 20
GGGGSGGGGS GGGGS                                                     15

SEQ ID NO: 21           moltype = AA   length = 184
FEATURE                 Location/Qualifiers
source                  1..184
                        mol_type = protein
                        organism = Homo sapiens
SEQUENCE: 21
MLQMAGQCSQ NEYFDSLLHA CIPCQLRCSS NTPPLTCQRY CNASVTNSVK GTNAILWTCL    60
GLSLIISLAV FVLMFLLRKI NSEPLKDEFK NTGSGLLGMA NIDLEKSRTG DEIILPRGLE   120
YTVEECTCED CIKSKPKVDS DHCFPLPAME EGATILVTTK TNDYCKSLPA ALSATEIEKS   180
ISAR                                                                184

SEQ ID NO: 22           moltype = AA   length = 183
FEATURE                 Location/Qualifiers
```

```
source                  1..183
                        mol_type = protein
                        organism = Macaca nemestrina
SEQUENCE: 22
MLQMARQCSQ NEYFDSLLHD CKPCQLRCSS TPPLTCQRYC NASMTNSVKG MNAILWTCLG    60
LSLIISLAVF VLTFLLRKMS SEPLKDEFKN TGSGLLGMAN IDLEKGRTGD EIVLPRGLEY   120
TVEECTCEDC IKNKPKVDSD HCFPLPAMEE GATILVTTKT NDYCNSLSAA LSVTEIEKSI   180
SAR                                                                 183

SEQ ID NO: 23           moltype = AA  length = 185
FEATURE                 Location/Qualifiers
source                  1..185
                        mol_type = protein
                        organism = Mus musculus
SEQUENCE: 23
MAQQCFHSEY FDSLLHACKP CHLRCSNPPA TCQPYCDPSV TSSVKGTYTV LWIFLGLTLV    60
LSLALFTISF LLRKMNPEAL KDEPQSPGQL DGSAQLDKAD TELTRIRAGD DRIFPRSLEY   120
TVEECTCEDC VKSKPKGDSD HFFPLPAMEE GATILVTTKT GDYGKSSVPT ALQSVMGMEK   180
PTHTR                                                               185

SEQ ID NO: 24           moltype = AA  length = 184
FEATURE                 Location/Qualifiers
source                  1..184
                        mol_type = protein
                        organism = Homo sapiens
SEQUENCE: 24
MRRGPRSLRG RDAPAPTPCV PAECFDLLVR HCVACGLLRT PRPKPAGASS PAPRTALQPQ    60
ESVGAGAGEA ALPLPGLLFG APALLGLALV LALVLVGLVS WRRRQRRLRG ASSAEAPDGD   120
KDAPEPLDKV IILSPGISDA TAPAWPPPGE DPGTTPPGHS VPVPATELGS TELVTTKTAG   180
PEQQ                                                                184

SEQ ID NO: 25           moltype = AA  length = 293
FEATURE                 Location/Qualifiers
source                  1..293
                        mol_type = protein
                        organism = Homo sapiens
SEQUENCE: 25
MSGLGRSRRG GRSRVDQEER FPQGLWTGVA MRSCPEEQYW DPLLGTCMSC KTICNHQSQR    60
TCAAFCRSLS CRKEQGKFYD HLLRDCISCA SICGQHPKQC AYFCENKLRS PVNLPPELRR   120
QRSGEVENNS DNSGRYQGLE HRGSEASPAL PGLKLSADQV ALVYSTLGLC LCAVLCCFLV   180
AVACFLKKRG DPCSCQPRSR PRQSPAKSSQ DHAMEAGSPV STSPEPVETC SFCFPECRAP   240
TQESAVTPGT PDPTCAGRWG CHTRTTVLQP CPHIPDSGLG IVCVPAQEGG PGA          293

SEQ ID NO: 26           moltype = AA  length = 5
FEATURE                 Location/Qualifiers
source                  1..5
                        mol_type = protein
                        organism = synthetic construct
SEQUENCE: 26
DYTMH                                                               5

SEQ ID NO: 27           moltype = AA  length = 17
FEATURE                 Location/Qualifiers
source                  1..17
                        mol_type = protein
                        organism = synthetic construct
VARIANT                 6
                        note = T, S or H
VARIANT                 8
                        note = T, S or H
SEQUENCE: 27
GISWNXGXJG YADSVKG                                                  17

SEQ ID NO: 28           moltype = AA  length = 14
FEATURE                 Location/Qualifiers
source                  1..14
                        mol_type = protein
                        organism = synthetic construct
VARIANT                 2
                        note = N or R
VARIANT                 10
                        note = F or Y
SEQUENCE: 28
DXSGYGHYYX GMDV                                                     14

SEQ ID NO: 29           moltype = AA  length = 11
FEATURE                 Location/Qualifiers
source                  1..11
                        mol_type = protein
```

```
                        organism = synthetic construct
VARIANT                 4
                        note = Q or R
VARIANT                 8
                        note = R or L
VARIANT                 10
                        note = V or L
SEQUENCE: 29
RASXSVSXNX A                                                                    11

SEQ ID NO: 30           moltype = AA  length = 7
FEATURE                 Location/Qualifiers
source                  1..7
                        mol_type = protein
                        organism = synthetic construct
VARIANT                 5
                        note = R or K
VARIANT                 6
                        note = Q, Y or P
SEQUENCE: 30
GASTXXT                                                                         7

SEQ ID NO: 31           moltype = AA  length = 9
FEATURE                 Location/Qualifiers
source                  1..9
                        mol_type = protein
                        organism = synthetic construct
VARIANT                 2
                        note = S, Q or H
VARIANT                 4
                        note = I or T
VARIANT                 9
                        note = Q, T or R
SEQUENCE: 31
QXYXNWPLX                                                                       9

SEQ ID NO: 32           moltype = AA  length = 123
FEATURE                 Location/Qualifiers
source                  1..123
                        mol_type = protein
                        organism = synthetic construct
VARIANT                 30
                        note = S, D or G
VARIANT                 31
                        note = D or S
VARIANT                 33
                        note = T, S or A
VARIANT                 55
                        note = T, S or H
VARIANT                 57
                        note = T, S or H
VARIANT                 100
                        note = N or R
VARIANT                 108
                        note = F or Y
SEQUENCE: 32
EVQLVESGGG LVQPGRSLRL SCAASGFTFX XYXMHWVRQA PGKGLEWVSG ISWNXGXJGY               60
ADSVKGRFTI SRDNAKKSLY LQMNSLRAED TALYYCAKDX SGYGHYYXGM DVWGQGTTVT              120
VAS                                                                            123

SEQ ID NO: 33           moltype = AA  length = 107
FEATURE                 Location/Qualifiers
source                  1..107
                        mol_type = protein
                        organism = synthetic construct
VARIANT                 27
                        note = Q or R
VARIANT                 31
                        note = R or L
VARIANT                 33
                        note = V or L
VARIANT                 54
                        note = R or K
VARIANT                 55
                        note = Q, Y or P
VARIANT                 90
                        note = S, Q or H
VARIANT                 92
                        note = I or T
```

| VARIANT | 97 |
| --- | --- |
| | note = Q, T or R |

SEQUENCE: 33

```
EIVMTQSPAT LSVSPGERAT LSCRASXSVS XNXAWYQQKP GQAPRLLIYG ASTXXTGIPA   60
RFSGSGSGTE FTLTISSLQS EDFAVYYCQX YXNWPLXFGG GTKVEIK                107
```

| SEQ ID NO: 34 | moltype = AA   length = 717 |
| --- | --- |
| FEATURE | Location/Qualifiers |
| source | 1..717 |
| | mol_type = protein |
| | organism = synthetic construct |

SEQUENCE: 34

```
QVQLVQSGAE VKKPGASVKV SCKASGYTFT NHIIHWVRQA PGQGLEWMGY INPYPGYHGY   60
NDKFSGRATM TSDTSTSTVY MELSSLRSED TAVYYCARDG YYRDQDVLDY WGQGTLVTVS  120
SGGGGSGGGG SGGGGSGGGG SDIQMTQSPS SLSASVGDRV TITCKASQDI SQYLNWYQQK  180
PGKAPKLLIY YTSGLHPGVP SRFSGSGSGT DFTFTISSLE PEDEATYYCQ QGYALPWTFG  240
QGTKLTAKRG GGGSGGGGSG GGGSEVQLVE SGGGLVQPGR SLRLSCAASG FTFDDFAMHW  300
VRQAPGKGLE WVSGITWNSG SVGYADSVKG RFTISRDNAK KSLYLQMNSL RAEDTALYYC  360
AKDRSGYGHY YYGMDVWGQG TTVTVASAST KGPSVFPLAP SSKSTSGGTA ALGCLVKDYF  420
PEPVTVSWNS GALTSGVHTF PAVLQSSGLY SLSSVVTVPS SSLGTQTYIC NVNHKPSNTK  480
VDKKVEPKSC DKTHTCPPCP APEAAGGPSV FLFPPKPKDT LMISRTPEVT CVVVDVSHED  540
PEVKFNWYVD GVEVHNAKTK PREEQYASTY RVVSVLTVLH QDWLNGKEYK CKVSNKALPA  600
PIEKTISKAK GQPREPQVYT LPPSREEMTK NQVSLWCLVK GFYPSDIAVE WESNGQPENN  660
YKTTPPVLDS DGSFFLYSKL TVDKSRWQQG NVFSCSVMHE ALHNHYTQKS LSLSPGK     717
```

| SEQ ID NO: 35 | moltype = AA   length = 214 |
| --- | --- |
| FEATURE | Location/Qualifiers |
| source | 1..214 |
| | mol_type = protein |
| | organism = synthetic construct |

SEQUENCE: 35

```
EIVMTQSPAT LSVSPGERAT LSCRASTSVS HNVAWYQQKP GQAPRLLIYG ASTKVTGIPA   60
RFSGSGSGTE FTLTISSLQS EDFAVYYCQH YINWPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214
```

| SEQ ID NO: 36 | moltype = AA   length = 717 |
| --- | --- |
| FEATURE | Location/Qualifiers |
| source | 1..717 |
| | mol_type = protein |
| | organism = synthetic construct |
| VARIANT | 294 |
| | note = S, D or G |
| VARIANT | 295 |
| | note = D or S |
| VARIANT | 297 |
| | note = T, S or A |
| VARIANT | 319 |
| | note = T, S or H |
| VARIANT | 321 |
| | note = T, S or H |
| VARIANT | 364 |
| | note = N or R |
| VARIANT | 372 |
| | note = F or Y |

SEQUENCE: 36

```
QVQLVQSGAE VKKPGASVKV SCKASGYTFT NHIIHWVRQA PGQGLEWMGY INPYPGYHGY   60
NDKFSGRATM TSDTSTSTVY MELSSLRSED TAVYYCARDG YYRDQDVLDY WGQGTLVTVS  120
SGGGGSGGGG SGGGGSGGGG SDIQMTQSPS SLSASVGDRV TITCKASQDI SQYLNWYQQK  180
PGKAPKLLIY YTSGLHPGVP SRFSGSGSGT DFTFTISSLE PEDEATYYCQ QGYALPWTFG  240
QGTKLTAKRG GGGSGGGGSG GGGSEVQLVE SGGGLVQPGR SLRLSCAASG FTFXXYXMHW  300
VRQAPGKGLE WVSGISWNXG XJGYADSVKG RFTISRDNAK KSLYLQMNSL RAEDTALYYC  360
AKDRSGYGHY YXGMDVWGQG TTVTVASAST KGPSVFPLAP SSKSTSGGTA ALGCLVKDYF  420
PEPVTVSWNS GALTSGVHTF PAVLQSSGLY SLSSVVTVPS SSLGTQTYIC NVNHKPSNTK  480
VDKKVEPKSC DKTHTCPPCP APEAAGGPSV FLFPPKPKDT LMISRTPEVT CVVVDVSHED  540
PEVKFNWYVD GVEVHNAKTK PREEQYASTY RVVSVLTVLH QDWLNGKEYK CKVSNKALPA  600
PIEKTISKAK GQPREPQVYT LPPSREEMTK NQVSLWCLVK GFYPSDIAVE WESNGQPENN  660
YKTTPPVLDS DGSFFLYSKL TVDKSRWQQG NVFSCSVMHE ALHNHYTQKS LSLSPGK     717
```

| SEQ ID NO: 37 | moltype = AA   length = 214 |
| --- | --- |
| FEATURE | Location/Qualifiers |
| source | 1..214 |
| | mol_type = protein |
| | organism = synthetic construct |
| VARIANT | 27 |
| | note = Q or R |
| VARIANT | 31 |
| | note = R or L |
| VARIANT | 33 |

```
                        note = V or L
VARIANT                 54
                        note = R or K
VARIANT                 55
                        note = Q, Y or P
VARIANT                 90
                        note = S, Q or H
VARIANT                 92
                        note = I or T
VARIANT                 97
                        note = Q, T or R
SEQUENCE: 37
EIVMTQSPAT LSVSPGERAT LSCRASXSVS XNXAWYQQKP GQAPRLLIYG ASTXXTGIPA    60
RFSGSGSGTE FTLTISSLQS EDFAVYYCQX YXNWPLXFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 38           moltype = AA   length = 451
FEATURE                 Location/Qualifiers
source                  1..451
                        mol_type = protein
                        organism = synthetic construct
SEQUENCE: 38
QVQLVQSGAE VKKPGASVKV SCKASGYTFT NHIIHWVRQA PGQGLEWMGY INPYPGYHGY    60
NDKFSGRATM TSDTSTSTVY MELSSLRSED TAVYYCARDG YYRDQDVLDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAAG   240
GPSVFLFPPK PKDTLMISRT PEVTCVVVDV SHEDPEVKFN WYVDGVEVHN AKTKPREEQY   300
ASTYRVVSVL TVLHQDWLNG KEYKCKVSNK ALPAPIEKTI SKAKGQPREP QVYTLPPSRE   360
EMTKNQVSLS CAVKGFYPSD IAVEWESNGQ PENNYKTTPP VLDSDGSFFL VSKLTVDKSR   420
WQQGNVFSCS VMHEALHNHY TQKSLSLSPG K                                  451

SEQ ID NO: 39           moltype = AA   length = 214
FEATURE                 Location/Qualifiers
source                  1..214
                        mol_type = protein
                        organism = synthetic construct
SEQUENCE: 39
DIQMTQSPSS LSASVGDRVT ITCKASQDIS QYLNWYQQKP GKAPKLLIYY TSGLHPGVPS    60
RFSGSGSGTD FTFTISSLEP EDIATYYCQQ GYALPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 40           moltype = AA   length = 108
FEATURE                 Location/Qualifiers
source                  1..108
                        mol_type = protein
                        organism = synthetic construct
SEQUENCE: 40
DIQMTQSPSS LSASVGDRVT ITCKASQDIS QYLNWYQQKP GKAPKLLIYY TSGLHPGVPS    60
RFSGSGSGTD FTFTISSLEP EDEATYYCQQ GYALPWTFGQ GTKLTAKR                108

SEQ ID NO: 41           moltype = AA   length = 5
FEATURE                 Location/Qualifiers
source                  1..5
                        mol_type = protein
                        organism = synthetic construct
SEQUENCE: 41
SYSMH                                                                 5

SEQ ID NO: 42           moltype = AA   length = 5
FEATURE                 Location/Qualifiers
source                  1..5
                        mol_type = protein
                        organism = synthetic construct
SEQUENCE: 42
DYAMH                                                                 5
```

We claim:

1. An isolated monoclonal anti-BCMA antibody or an antigen binding fragment thereof, comprising a heavy chain variable region that comprises a VH-CDR1, a VH-CDR2 and a VH-CDR3, and a light chain variable region that comprises a VL-CDR1, a VL-CDR2 and a VL-CDR3, wherein the VH-CDR1, the VH-CDR2, the VH-CDR3, the VL-CDR1, the VL-CDR2 and the VL-CDR3 comprise the amino acid sequences of SEQ ID NOs: 1, 2, 3, 4, 5, and 6, respectively.

2. The anti-BCMA antibody or the antigen binding fragment thereof according to claim 1, wherein the heavy chain variable region comprises an amino acid sequence having at least 85%, 86%, 87%, 88%, 89%, 90%, 91%, 92%, 93%, 94%, 95%, 96%, 97%, 98%, 99% or 100% sequence identity to SEQ ID NO: 7.

3. The anti-BCMA antibody or the antigen binding fragment thereof according to claim 1, wherein the light chain variable region comprises an amino acid sequence having at least 85%, 86%, 87%, 88%, 89%, 90%, 91%, 92%, 93%, 94%, 95%, 96%, 97%, 98%, 99% or 100% sequence identity to SEQ ID NOs: 8 or 40.

4. The anti-BCMA antibody or the antigen binding fragment thereof according to claim 2, wherein the heavy chain variable region and the light chain variable region comprise amino acid sequences having at least 85%, 86%, 87%, 88%, 89%, 90%, 91%, 92%, 93%, 94%, 95%, 96%, 97%, 98%, 99% or 100% sequence identity to (1) SEQ ID NOs: 7 and 8, respectively; (2) SEQ ID NOs: 7 and 40, respectively.

5. The anti-BCMA antibody or the antigen binding fragment thereof according to claim 1, further comprising a heavy chain constant region linked to the heavy chain variable region comprising the amino acid sequence of SEQ ID NO: 17 (X1=L, X2=L, X3=N, X4=T, X5=L, X6=Y), and a light chain constant region linked to the light chain variable region comprising the amino acid sequence of SEQ ID NO: 18.

6. A bispecific molecule, comprising:
   i) a CD3 binding domain, comprising an anti-CD3 antibody or an antigen binding fragment thereof, wherein the anti-CD3 antibody or the antigen binding fragment thereof comprises a heavy chain variable region that comprises a VH-CDR1, a VH-CDR2 and a VH-CDR3, and a light chain variable region that comprises a VL-CDR1, a VL-CDR2 and a VL-CDR3, wherein the VH-CDR1, the VH-CDR2, the VH-CDR3, the VL-CDR1, the VL-CDR2 and the VL-CDR3 comprise the amino acid sequences of
      (1) SEQ ID NOs: 9, 10, 11, 12, 13 and 14, respectively;
      (2) SEQ ID NOs: 26, 27 (X1=T, X2=T, J=I), 28 (X1=N, X2=F), 29 (X1=Q, X2=R, X3=V), 30 (X1=R, X2=Q) and 31 (X1=S, X2=I, X3=Q), respectively;
      (3) SEQ ID NOs: 41, 27 (X1=S, X2=S, J=L), 28 (X1=R, X2=Y), 29 (X1=R, X2=L, X3=V), 30 (X1=K, X2=Y), and 31 (X1=Q, X2=I, X3=T), respectively; or
      (4) SEQ ID NOs: 42, 27 (X1=H, X2=H, J-I), 28 (X1=N, X2=Y), 29 (X1=R, X2=R, X3=L), 30 (X1=K, X2=P), and 31 (X1=H, X2-T, X3=R), respectively; and
   ii) a BCMA binding domain, comprising the anti-BCMA antibody or the antigen binding fragment thereof according to claim 1.

7. The bispecific molecule according to claim 6, comprising one CD3 binding domain, and two BCMA binding domains.

8. The bispecific molecule according to claim 7, comprising:
   i) a first polypeptide, comprising the anti-BCMA heavy chain variable region, and a heavy chain constant region;
   ii) a second polypeptide, comprising the anti-BCMA light chain variable region,
   iii) a third polypeptide, comprising the anti-BCMA heavy chain variable region, the anti-BCMA light chain variable region, the anti-CD3 heavy chain variable region, and a heavy chain constant region; and
   iv) a fourth polypeptide, comprising the anti-CD3 light chain variable region, wherein the anti-BCMA heavy chain variable region in the first polypeptide and the anti-BCMA light chain variable region in the second polypeptide associate to form the BCMA binding domain, the anti-BCMA heavy chain variable region and the anti-BCMA light chain variable region in the third polypeptide associate to form the BCMA binding domain, the anti-CD3 heavy chain variable region in the third polypeptide and the anti-CD3 light chain variable region in the fourth polypeptide associate to form the CD3 binding domain, and the heavy chain constant region in the first polypeptide and the heavy chain constant region in the third polypeptide are associated together.

9. The bispecific molecule according to claim 8, wherein anti-CD3 heavy chain variable region and the anti-CD3 light chain variable region comprise amino acid sequences having at least 85%, 86%, 87%, 88%, 89%, 90%, 91%, 92%, 93%, 94%, 95%, 96%, 97%, 98%, 99% or 100% sequence identity to
   (1) SEQ ID NOs: 15 and 16, respectively;
   (2) SEQ ID NOs: 32 (X1=S, X2=D, X3=T, X4=T, X5=T, J=I, X6=N, X7=F) and 33 (X1=Q, X2=R, X3=V, X4=R, X5=Q, X6=S, X7=I, X8-Q), respectively;
   (3) SEQ ID NOs: 32 (X1=D, X2=S, X3=S, X4=S, X5=S, J=L, X6=R, X7=Y) and 33 (X1=R, X2=L, X3=V, X4=K, X5=Y, X6=Q, X7=I, X8=T), respectively; or
   (4) SEQ ID NOs: 32 (X1=G, X2=D, X3=A, X4=H, X5=H, J=I, X6=N, X7=Y) and 33 (X1=R, X2=R, X3=L, X4=K, X5=P, X6-H, X7=T, X8=R) respectively.

10. The bispecific molecule according to claim 8, wherein the heavy chain constant region in the first polypeptide comprises the amino acid sequence of SEQ ID NO: 17 (X1=A, X2=A, X3=A, X4=S, X5=A, X6=V), and the heavy chain constant region in the third polypeptide comprises the amino acid sequence of SEQ ID NO: 17 (X1=A, X2=A, X3=A, X4=W, X5=L, X6=Y).

11. The bispecific molecule according to claim 8, wherein the first polypeptide comprises, from N-terminus to C-terminus, the anti-BCMA heavy chain variable region and the heavy chain constant region, and the third polypeptide comprises, from N-terminus to C-terminus, the anti-BCMA heavy chain variable region, the anti-BCMA light chain variable region, the anti-CD3 heavy chain variable region, and the heavy chain constant region.

12. The bispecific molecule according to claim 11, wherein in the third polypeptide, the anti-BCMA heavy chain variable region is linked via a linker of SEQ ID NO: 19 to the anti-BCMA light chain variable region, and the anti-BCMA light chain is linked via a linker of SEQ ID NO: 20 to the anti-CD3 heavy chain variable region.

13. The bispecific molecule according to claim 8, wherein the first, the second, the third and the fourth polypeptides comprise amino acid sequences having at least 85%, 86%, 87%, 88%, 89%, 90%, 91%, 92%, 93%, 94%, 95%, 96%, 97%, 98%, 99% or 100% sequence identity to
  (1) SEQ ID NOs: 38, 39, 34 and 35, respectively;
  (2) SEQ ID NOs: 38, 39, 36 (X1=S, X2-D, X3-T, X4=T, X5=T, J=I, X6=N, X7=F), and 37 (X1=Q, X2=R, X3=V, X4=R, X5=Q, X6=S, X7=I, X8=Q), respectively;
  (3) SEQ ID NOs: 38, 39, 36 (X1=D, X2=S, X3=S, X4=S, X5=S, J=L, X6=R, X7=Y), and 37 (X1=R, X2=L, X3=V, X4-K, X5=Y, X6-Q, X7=I, X8=T), respectively; or
  (4) SEQ ID NOs: 38, 39, 36 (X1=G, X2=D, X3=A, X4=H, X5=H, J=I, X6=N, X7=Y), and 37 (X1=R, X2=R, X3=L, X4=K, X5=P, X6=H, X7=T, X8=R), respectively.

14. A nucleic acid molecule, encoding the anti-BCMA antibody or antigen binding fragment thereof according to claim 1.

15. A nucleic acid molecule, encoding the bispecific molecule according to claim 6.

16. A pharmaceutical composition comprising the anti-BCMA antibody or antigen binding fragment thereof according to claim 1, and a pharmaceutically acceptable carrier.

17. A pharmaceutical composition comprising the bispecific molecule according to claim 6, and a pharmaceutically acceptable carrier.

18. A method for treating or alleviating a BCMA associated disease in a subject in need thereof, comprising administering to the subject a therapeutically effective amount of the pharmaceutical composition according to claim 16, wherein the BCMA associated disease is multiple myeloma, plasmacytoma, plasma cell leukemia, macroglobulinemia, solitary plasmacytoma, or extramedullary plasmacytoma.

19. A method for treating or alleviating a BCMA associated disease in a subject in need thereof, comprising administering to the subject a therapeutically effective amount of the pharmaceutical composition according to claim 17.

20. The method according to claim 19, wherein the BCMA associated disease is multiple myeloma, plasma cell leukemia, Waldenstrom macroglobulinemia, amyloidosis, extramedullary plasmacytoma, heavy chain disease, or monoclonal gammopathy of undetermined significance.

* * * * *